US005597725A

United States Patent [19]
Suzuki

[11] Patent Number: 5,597,725
[45] Date of Patent: Jan. 28, 1997

[54] CADHERIN-SPECIFIC ANTIBODIES AND HYBRIDOMA CELL LINES

[75] Inventor: Shintaro Suzuki, Torrance, Calif.

[73] Assignee: Doheny Eye Institute, Los Angeles, Calif.

[21] Appl. No.: 188,228

[22] Filed: Jan. 26, 1994

Related U.S. Application Data

[63] Continuation-in-part of Ser. No. 49,460, Apr. 19, 1993, abandoned, which is a continuation-in-part of Ser. No. 872,643, Apr. 17, 1992, abandoned.

[51] Int. Cl.$^6$ .............. C12N 5/12; A61K 51/10; C07K 16/00; C07K 16/28
[52] U.S. Cl. .............. 435/328; 435/70.21; 435/172.2; 435/331; 435/336; 435/332; 530/387.3; 530/388.1; 530/388.22; 530/389.1; 530/389.2
[58] Field of Search .............. 530/388.1, 388.22, 530/389.1, 389.2, 387.3; 435/70.21, 172.2, 240.27

[56] References Cited

FOREIGN PATENT DOCUMENTS

WO91/04745  4/1991  WIPO.
WO92/08731  5/1992  WIPO.

OTHER PUBLICATIONS

Staskus et al. [Virology 181:228–240 (1991)].
Suzuki et al. [Cell Regulation 2:261–270 (1991)].
Lerner [Nature 299:592–596 (1982)].
Geiger et al. [J. Cell Science 97:607–614 (1990)].
Ausubel et al., Eds., *Current Protocols in Molecular Biology*, Sections 6.1.1 to 6.1.4 and 6.2.1 to 6.2.3, John Wiley & Sons, New York (1987).
Behrens et al., "Dissecting Tumor Cell Invasion: Epithelial Cells Acquire Invasive Properties after the Loss of Uvomorulin–Mediated Cell–Cell Adhesion", *J. Cell Biol.*, 108:2435–2447 (Jun. 1989).
Blaschuk et al., "Identification of a Cadherin Cell Adhesion Recognition Sequence", *Devel. Biol.*, 139:227–229 (1990).
Civitelli et al., "Connexin43 Mediates Direct Intercellular Communication in Human Osteoblastic Cell Networks", *J. Clin Invest.*, 91:1888–1896 (1993).
Collins et al., "Cloning and Sequence Analysis of Desmosomal Glycoproteins 2 and 3 (Desmocollins): Cadherin–like Desmosomal Adhesion Molecules with Heterogenous Cytoplasmic Domains", *J. Cell Biol.*, 113(2):381–391 (Apr. 1991).
Detrick et al., "The Effects of N–Cadherin Misexpression on Morphogenesis in Xenopus Embryos", *Neuron*, 4:493–506 (Apr. 1990).
Donalies et al., "Expression of M–cadherin, A Member of the Cadherin Multigene Family, Correlates with Differentiation of Skeletal Muscle Cells", *Proc. Natl. Acad. Sci. USA*, 88:8024–8028 (1991).
Franke et al., "Immunolocalization of Plakoglobin in Endothelial Junctions: Identification as a Special Type of *Zonulae adhaerentes*", *Biol. of the Cell*, 59:205–218 (1987).

Franke et al., "Molecular Cloning and Amino Acid Sequence of Human Plakoglobin, the Common Junctional Plaque Protein", *Proc. Natl. Acad. Sci. USA*, 86:4027–4031 (1989).
Frixen et al., "E–Cadherin–Mediated Cell—Cell Adhesion Prevents Invasiveness of Human Carcinoma Cells", *J. Cell Biol.*, 113(1):173–185 (Apr. 1991).
Fugimori et al., "Disruption of Epithelial Cell—Cell Adhesion by Exogenous Expression of a Mutated Nonfunctional N–Cadherin", *Molecular Biology of the Cell*, 4:37–47 (1993).
Furie et al., "Migration of Neutrophils Across Endothelial Monolayers is Stimulated by Treatment of the Monolayers with Interleukin–1 or Tumor Necrosis Factor–$\alpha$", *J. Immunol.*, 143:3309–3317 (1989).
Furie et al., "E–Selectin (Endothelial–Leukocyte Adhesion Molecule–1) is Not Required for the Migration of Neutrophils Across IL–1 Stimulated Endothelium In Vitro", *J. Immunol.*, 148:2395–2484 (1992).
Furie et al., "Monoclonal Antibodies to Leukocyte Integrins CD11a/CD18 and CD11b/CD18 or Intercellular Adhesion Molecule–1 Inhibit Chemoattractant–Stimulated Neutrophil Transendothelial Migration In Vitro", *Blood*, 78:2089–2097 (1991).
Gallin et al., "Sequence Analysis of a cDNA Encoding the Liver Cell Adhesion Molecule, L–CAM", *Proc. Natl. Acad. Sci. USA*, 84:2808–2812 (1987).
Geiger et al., "Broad Spectrum Pan–Cadherin Antibodies, Reactive with the C–Terminal 24 Amino Acid Residues of N–Cadherin", *J. Cell Science*, 97:607–614 (1990).
Hatta et al., "Cloning and Expression of cDNA Encoding a Neural Calcium–Dependent Cell Adhesion Molecule: Its Identity in the Cadherin Gene Family", *J. Cell. Biol.*, 106:873–881 (1988).
Heimark et al., "Identification of a $Ca^{2+}$–Dependent Cell—Cell Adhesion Molecule in Endothelial Cells", *J. Cell Biol.*, 110:1745–1756 (1990).
Herrenkenecht et al., "The Uvomorulin–Anchorage Protein $\alpha$ Catenin is a Vinculin Homologue", *Proc. Natl. Acad. Sci. USA*, 88:9156–9160 (1991).
Inuzuka et al., "R–Cadherin: A Novel $Ca^{2+}$–Dependent Cell—Cell Adhesion Molecule Expressed in the Retina", *Neuron*, 7:69–79 (1991).
Johnson et al., "P–and E–Cadherin Are in Separate Complexes in Cells Expressing Both Cadherins", *Exp. Cell. Reg.* 207:252–260 (1993).
Kintner et al., "Regulation of Embryonic Cell Adhesion by the Cadherin Cytoplasmic Domain", *Cell*, 69:229–236 (1992).

(List continued on next page.)

*Primary Examiner*—Donald E. Adams
*Attorney, Agent, or Firm*—Marshall, O'Toole, Gerstein, Murray & Borun

[57] ABSTRACT

DNA sequences encoding novel cadherins, desginated cadherins-4 through -12, are disclosed along with methods and materials for the recombinant production of the same. Antibody substances specific for the novel cadherins and cadherin peptides are disclosed as useful for modulating the natural binding and/or regulatory activities of the cadherins.

6 Claims, 1 Drawing Sheet

OTHER PUBLICATIONS

Klambt et al., "The Drosophila Melanogaster 1(2)gl Gene Encodes a Protein Homologous to the Cadherin Cell–Adhesion Molecule Family", *Devel. Biol.*, 133:425–436 (1989).

Koch et al., "Identification of Desmoglein, a Constitutive Desmosonal Glycoprotein, as a Member of the Cadherin Family of Cell Adhesion Molecules", *Eur. J. Cell. Biol.*, 53:1–12 (1990).

Liaw et al., "Identification and Cloning of Two Species of Cadherins in Bovine Endothelial Cells", *EMBO J.*, 9:2701–2708 (1990).

Mahoney et al., "The Fat Tumor Suppressor Gene in Drosophila Encodes a Novel Member of the Cadherin Gene Superfamily", *Cell*, 67:853–868 (1991).

Maniatis et al., Eds., *Molecular Cloning: A Laboratory Manual*, "Guanidinium/Cesium Chloride Method", p. 196, Cold Spring Laboratory, Cold Spring Harbor, New York (1982).

Matsunaga et al., "Guidance of Optic Nerve Fibres by N–Cadherin Adhesion Molecules", *Nature*, 334:62–64 (1988).

McCrea et al., "A Homolog of the *armadillo* Protein in *Drosophila* (Plakoglobin) Associated with E–Cadherin", *Science*, 254:1359–1361 (1991).

Nagafuchi et al., "Transformation of Cell Adhesion Properties by Exogenously Introduced E–Cadherin cDNA", *Nature*, 329:341–343 (1987).

Nagafuchi et al., "The 102 kd Cadherin–Associated Protein: Similarity to Vinculin and Posttranscriptional Regulation of Expression", *Cell*, 65:849–857 (1991).

Napolitano et al., "Molecular Cloning and Characterization of B–Cadherin, a Novel Chick Cadherin", *J. Cell Biol.*, 113:893–905 (1991).

Nelson et al., "Identification of a Membrane–Cytoskeletal Complex Containing the Cell Adhesion Molecule Uvomorulin (E–Cadherin) Ankyrin, and Fodrin in Madin–Darby Canine Kidney Epithelial Cells", *J. Cell Biol.*, 110:349–357 (1990).

Nose et al., "Isolation of Placental Cadherin cDNA:Identification of a Novel Gene Family of Cell—Cell Adhesion Molecules", *EMBO J.* 6:3655–3661 (1987).

Ozawa et al., "The Cytoplasmic Domain of the Cell Adhesion Molecule Uvomorulin Associates with Three Independent Proteins Structurally Related in Different Species", *EMBO J.*, 8:1711–1717 (1989).

Peifer et al., "The Vertebrate Adhesive Junction Proteins β–catenin and Plakoglobin and the *Drosophila* Segment Polarity Gene *armadillo* Form a Multigene Family with Similar Properties", *J. Cell Biol.*, 118:681–691 (1992).

Ranscht et al., "T–Cadherin, a Novel Cadherin Cell Adhesion Molecule in the Nervous System Lacks the Conserved Cytoplasmic Region", *Neuron*, 7:391–402 (1991).

Ringwald et al., "The Structure of Cell Adhesion Molecule Uvomorulin. Insights into the Molecular Mechanism of $Ca^{2+}$–Dependent Cell Adhesion", *EMBO J.*, 6:3647–3653 (1987).

Sacristan et al., "Evidence for the Coexistance of Two T–cadherin Forms in the Developing Chicken Nervous System", *J. Cell Biol.*, 111, Abstract 158a (1990).

Saiki et al., "Primer–Directed Enzymatic Amplification of DNA with a Thermostable DNA Polymerase", *Science*, 239:487–491 (1988).

Seldin et al., "Genetic Analysis of Autoimmune *gld* Mice", *J. Exp. Med.*, 167:688–693 (1988).

Shimoyama et al., "Cadherin Dysfunction in a Human Cancer Cell Line:Possible Involvement of Loss of α–Catenin Expression in Reduced Cell—Cell Adhesiveness[1]", *Cancer Res.*, 52:5770–5774 (1992).

Suzuki et al., "Evidence for Cadherin Superfamily", *J. Cell Biol.*, 115:Abstract 72a (1991).

Suzuki et al., "Evidence for Cadherin Superfamily", *Cell. Struc. Funct.*, 16:605 (1991).

Takeichi, "Cadherins:A Molecular Family Important in Selective Cell—Cell Adhesion", *Annu. Rev. Biochem.*, 59:237–252 (1990).

Takeichi, "Cadherin Cell Adhesion Receptors as a Morphogenetic Regulator", *Science*, 251:1451–1455 (1991).

Tanihara et al., "Molecular Cloning of Novel Cadherins from Neural Retina", *Invest. Opthalmol. Vis. Sci.*, 32:1013 (1991).

Thomas, "Hybridization of Denatured RNA and Small DNA Fragments Transferred to Nitrocellulose", *Proc. Natl. Acad. Sci. USA*, 77:5201–5202 (1980).

Vleminckx et al., "Genetic Manipulation of E–Cadherin Expression by Epithelial Tumor Cells Reveals an Invasion Suppressor Role", *Cell*, 66:107–119 (Jul. 1991).

Yoshida–Noro et al., "Molecular Nature of the Calcium–Dependent Cell—Cell Adhesion System in Mouse Teratocarcinoma and Embryonic Cells Studied with a Monoclonal Antibody", *Devel. Biol.*, 101:19–27 (1984).

SEQUENCE LISTING ( 1 ) GENERAL INFORMATION:

( i i i ) NUMBER OF SEQUENCES: 62

( 2 ) INFORMATION FOR SEQ ID NO:1:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Thr Ala Pro Pro Tyr Asp
1               5

( 2 ) INFORMATION FOR SEQ ID NO:2:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

GAATTCACNG CNCCNCCNTA YGA          2 3

( 2 ) INFORMATION FOR SEQ ID NO:3:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

Phe Lys Lys Leu Ala Asp
1               5

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

GAATTCTCNG CNARYTTYTT RAA      23

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2
        ( D ) OTHER INFORMATION: /note= "The amino acid at this
            position is a proline or a glycine."

( i x ) FEATURE:
        ( A ) NAME/KEY: Modified-site
        ( B ) LOCATION: 3
        ( D ) OTHER INFORMATION: /note= "The amino acid at this
            position is a leucine, an isoleucine or a valine."

( i x ) FEATURE:
        ( A ) NAME/KEY: Modified-site
        ( B ) LOCATION: 5
        ( D ) OTHER INFORMATION: /note= "The amino acid at this
            position is a phenylalanine or a tyrosine."

( x i ) SEQUENCE DESCRIPTION: SEQ ID NO:5:

Lys Xaa Xaa Asp Xaa Glu
1              5

( 2 ) INFORMATION FOR SEQ ID NO:6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

GAATTCAARS SNNTNGAYTW YGA      23

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "The amino acid at this
            position is an asparagine or an aspartic acid."

( i x ) FEATURE:
   ( A ) NAME/KEY: Modified-site
   ( B ) LOCATION: 3
   ( D ) OTHER INFORMATION: /note= "The amino acid at this position is an alanine or a proline."

( x i ) SEQUENCE DESCRIPTION: SEQ ID NO:7:

Xaa Glu Xaa Pro Xaa Phe
1               5

( 2 ) INFORMATION FOR SEQ ID NO:8:

( i ) SEQUENCE CHARACTERISTICS:
      ( A ) LENGTH: 23 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:8:

GAATTCRAAN NNNGGNGSYT CRT                                              23

( 2 ) INFORMATION FOR SEQ ID NO:9:

( i ) SEQUENCE CHARACTERISTICS:
      ( A ) LENGTH: 117 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:9:

TCCCTGCTGG TCTTCGACTA CGAAGGCAGC GGTTCTACTG CAGGCTCTGT CAGCTCCCTG      60

AACTCCTCCA GCTCCGGGGA TCAAGATTAC GACTACTTGA ATGACTGGGG GCCCCGG        117

( 2 ) INFORMATION FOR SEQ ID NO:10:

( i ) SEQUENCE CHARACTERISTICS:
      ( A ) LENGTH: 39 amino acids
      ( B ) TYPE: amino acid
      ( D ) TOPOLOGY: linear ( i i ) MOLECULE TYPE: protein ( x i ) SEQUENCE DESCRIPTION: SEQ ID NO:10:

Ser Leu Leu Val Phe Asp Tyr Glu Gly Ser Gly Ser Thr Ala Gly Ser
1               5                   10                  15

Val Ser Ser Leu Asn Ser Ser Ser Ser Gly Asp Gln Asp Tyr Asp Tyr
                20                  25                  30

Leu Asn Asp Trp Gly Pro Arg
            35

( 2 ) INFORMATION FOR SEQ ID NO:11:

( i ) SEQUENCE CHARACTERISTICS:
      ( A ) LENGTH: 120 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:11:

ACACTGCACA TCTACGGCTA CGAGGGCACA GAGTCCATCG CAGAGTCCCT CAGCTCCCTG      60

AGCACCAATT CCTCCGACTC TGACATCGAC TATGACTTCC TCAATGACTG GGGACCCAGG    120

( 2 ) INFORMATION FOR SEQ ID NO:12:

( i ) SEQUENCE CHARACTERISTICS:
    ( A ) LENGTH: 40 amino acids
    ( B ) TYPE: amino acid
    ( D ) TOPOLOGY: linear ( i i ) MOLECULE TYPE: protein ( x i ) SEQUENCE DESCRIPTION: SEQ ID NO:12:

Thr Leu His Ile Tyr Gly Tyr Glu Gly Thr Glu Ser Ile Ala Glu Ser
1               5                   10                  15

Leu Ser Ser Leu Ser Thr Asn Ser Ser Asp Ser Asp Ile Asp Tyr Asp
            20                  25                  30

Phe Leu Asn Asp Trp Gly Pro Arg
            35              40

( 2 ) INFORMATION FOR SEQ ID NO:13:

( i ) SEQUENCE CHARACTERISTICS:
    ( A ) LENGTH: 120 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

TCCTTGGCCA CCTATGCCTA CGAAGGAACT GGCTCGGTGG CCGACTCCCT GAGCTCACTA      60

GAATCAGTGA CCACAGATGG AGACCAAGAT TATGACTATT TGAGTGACTG GGGCCCTCGA     120

( 2 ) INFORMATION FOR SEQ ID NO:14:

( i ) SEQUENCE CHARACTERISTICS:
    ( A ) LENGTH: 40 amino acids
    ( B ) TYPE: amino acid
    ( D ) TOPOLOGY: linear ( i i ) MOLECULE TYPE: protein ( x i ) SEQUENCE DESCRIPTION: SEQ ID NO:14:

Ser Leu Ala Thr Tyr Ala Tyr Glu Gly Thr Gly Ser Val Ala Asp Ser
1               5                   10                  15

Leu Ser Ser Leu Glu Ser Val Thr Thr Asp Gly Asp Gln Asp Tyr Asp
            20                  25                  30

Tyr Leu Ser Asp Trp Gly Pro Arg
            35              40

( 2 ) INFORMATION FOR SEQ ID NO:15:

( i ) SEQUENCE CHARACTERISTICS:
    ( A ) LENGTH: 120 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

TCGCTTCAGA CTTATGCATT TGAAGGAAAT GGCTCAGTAG CTGAATCTCT CAGTTCTTTA      60

GATTCTAACA GCTCGAACTC TGATCAGAAT TATGACTACC TTAGTGACTG GGGTCCTCTC    120

( 2 ) INFORMATION FOR SEQ ID NO:16:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Ser Leu Gln Thr Tyr Ala Phe Glu Gly Asn Gly Ser Val Ala Glu Ser
1               5                   10                  15

Leu Ser Ser Leu Asp Ser Asn Ser Asn Ser Asp Gln Asn Tyr Asp
            20                  25                  30

Tyr Leu Ser Asp Trp Gly Pro Arg
            35                  40
```

( 2 ) INFORMATION FOR SEQ ID NO:17:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:17:

```
TCCATTCAGA TTTATGGCTA TGAAGGCCGA GGGTCTGTGG CTGGCTCTCT CAGCTCGTTG      60

GAGTCCACCA CATCAGACTC AGACCAGAAT TTTGACTACC TCAGTGACTG GGGTCCCCGC     120
```

( 2 ) INFORMATION FOR SEQ ID NO:18:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Ser Ile Gln Ile Tyr Gly Tyr Glu Gly Arg Gly Ser Val Ala Gly Ser
1               5                   10                  15

Leu Ser Ser Leu Glu Ser Thr Thr Ser Asp Ser Asp Gln Asn Phe Asp
            20                  25                  30

Tyr Leu Ser Asp Trp Gly Pro Arg
            35                  40
```

( 2 ) INFORMATION FOR SEQ ID NO:19:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

```
TCCTTGGCCA CTTACGCCTA TGAAGGGAAT GATTCTGTAG CCAATTCTCT CAGCTCCTTA      60

GAATCTCTCA CAGCTGATTG TACCCAGGAT TATGACTACC TTAGTGACTG GGGGCCACGC     120
```

( 2 ) INFORMATION FOR SEQ ID NO:20:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Ser Leu Ala Thr Tyr Ala Tyr Glu Gly Asn Asp Ser Val Ala Asn Ser
1               5                   10                  15
Leu Ser Ser Leu Glu Ser Leu Thr Ala Asp Cys Asn Gln Asp Tyr Asp
            20                  25                  30
Tyr Leu Ser Asp Trp Gly Pro Arg
            35                  40
```

( 2 ) INFORMATION FOR SEQ ID NO:21:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
TCGCTGGCTA CCTATGCCTA TGAAGGAAAC GACTCTGTTG CTGAATCTCT GAGCTCCTTA        60

GAATCAGGTA CCACTGAAGG AGACCAAAAC TACGATTACC TTCGAGAATG GGGGCCTCGG       120
```

( 2 ) INFORMATION FOR SEQ ID NO:22:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Ser Leu Ala Thr Tyr Ala Tyr Glu Gly Asn Asp Ser Val Ala Glu Ser
1               5                   10                  15
Leu Ser Ser Leu Glu Ser Gly Thr Thr Glu Gly Asp Gln Asn Tyr Asp
            20                  25                  30
Tyr Leu Arg Glu Trp Gly Pro Arg
            35                  40
```

( 2 ) INFORMATION FOR SEQ ID NO:23:

( i ) SEQUENCE CHARACTERISTICS:
        ( A ) LENGTH: 120 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
TCCATCCAAA TCTATGGTTA TGAGGGCAGG GGTTCCGTGG CTGGGTCCCT GAGCTCCTTG        60

GAGTCTGCCA CCACAGATTC GGACCTGGAC TACGACTATC TACAGAACTG GGGACCTCGG       120
```

( 2 ) INFORMATION FOR SEQ ID NO:24:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Ser Ile Gln Ile Tyr Gly Tyr Glu Gly Arg Gly Ser Val Ala Gly Ser
1               5                   10                  15

Leu Ser Ser Leu Glu Ser Ala Thr Thr Asp Ser Asp Leu Asp Tyr Asp
            20              25                  30

Tyr Leu Gln Asn Trp Gly Pro Arg
        35              40
```

( 2 ) INFORMATION FOR SEQ ID NO:25:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:25:

```
AAGCGGTTTG ATTACGAGAT CTCTGCCTTT CACACCCTGC TGATCAAAGT GGAGAATGAG     60
GACCCATTGG TACCCGACGT CTCCTATGGC CCAGCTCCA  CGGCCACTGT CCACATCACG    120
GTCTTGGATG TCAACGAGGG ACCAGTCTTC                                     150
```

( 2 ) INFORMATION FOR SEQ ID NO:26:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Lys Arg Phe Asp Tyr Glu Ile Ser Ala Phe His Thr Leu Leu Ile Lys
1               5                   10                  15

Val Glu Asn Glu Asp Pro Leu Val Pro Asp Val Ser Tyr Gly Pro Ser
            20              25                  30

Ser Thr Ala Thr Val His Ile Thr Val Leu Asp Val Asn Glu Gly Pro
            35              40                  45

Val Phe
    50
```

( 2 ) INFORMATION FOR SEQ ID NO:27:

( i ) SEQUENCE CHARACTERISTICS:
        ( A ) LENGTH: 150 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

```
AAGGGTATGG ATTATGAGCT GAACCGTGCC TCCATGCTGA CCATAATGGT GTCCAACCAG     60
GCGCCCCTGG CCAGCGGGAT CCAGATGTCC TTCCAGTCCA CAGTGGGGGT AACCATCTCT    120
GTCACCGATG TCAACGAAGC CCCCTACTTC                                     150
```

( 2 ) INFORMATION FOR SEQ ID NO:28:

( i ) SEQUENCE CHARACTERISTICS:
        ( A ) LENGTH: 50 amino acids
        ( B ) TYPE: amino acid
        ( D ) TOPOLOGY: linear (i i) MOLECULE TYPE: protein (x i) SEQUENCE DESCRIPTION: SEQ ID NO:28:

| Lys | Gly | Met | Asp | Tyr | Glu | Leu | Asn | Arg | Ala | Ser | Met | Leu | Thr | Ile | Met |
| 1 | | | | 5 | | | | | 10 | | | | | 15 | |

| Val | Ser | Asn | Gln | Ala | Pro | Leu | Ala | Ser | Gly | Ile | Gln | Met | Ser | Phe | Gln |
| | | | 20 | | | | | 25 | | | | | 30 | | |

| Ser | Thr | Val | Gly | Val | Thr | Ile | Ser | Val | Thr | Asp | Val | Asn | Glu | Ala | Pro |
| | | 35 | | | | | 40 | | | | | 45 | | | |

| Tyr | Phe |
| | 50 |

(2) INFORMATION FOR SEQ ID NO:29:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:29:

```
AAACGACTGG ATTTTGAACT CATCCAGCAG TACACGTTCC ACATCGAGGC CACAGACCCC    60
ACTATCAGAC TCGGATACCT GAGCAGCACT GCGGGCAAAA ACAAAGCCAA GATCATCATC   120
AATGTCCTAG ATGTGGATGA GCCCCCTGTT TTC                                153
```

(2) INFORMATION FOR SEQ ID NO:30:

(i) SEQUENCE CHARACTERISTICS:
        (A) LENGTH: 51 amino acids
        (B) TYPE: amino acid
        (D) TOPOLOGY: linear (i i) MOLECULE TYPE: protein (x i) SEQUENCE DESCRIPTION: SEQ ID NO:30:

| Lys | Arg | Leu | Asp | Phe | Glu | Leu | Ile | Gln | Gln | Tyr | Thr | Phe | His | Ile | Glu |
| 1 | | | | 5 | | | | | 10 | | | | | 15 | |

| Ala | Thr | Asp | Pro | Thr | Ile | Arg | Leu | Gly | Tyr | Leu | Ser | Ser | Thr | Ala | Gly |
| | | | 20 | | | | | 25 | | | | | 30 | | |

| Lys | Asn | Lys | Ala | Lys | Ile | Ile | Ile | Asn | Val | Leu | Asp | Val | Asp | Glu | Pro |
| | | 35 | | | | | 40 | | | | | 45 | | | |

| Pro | Val | Phe |
| | | 50 |

(2) INFORMATION FOR SEQ ID NO:31:

(i) SEQUENCE CHARACTERISTICS:
        (A) LENGTH: 153 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:31:

```
AAGGGTTTGG ATTTTGAAAA GAAGAAAGTG TATACCCTTA AAGTGGAAGC CTCCAATCCT    60
TATGTTGAGC CACGATTTCT CTACTTGGGG CCTTTCAAAG ATTCAGCCAC GGTTAGAATT   120
GTGGTGGAGG ATGTAGATGA ACCTCCTGCC TTC                                153
```

(2) INFORMATION FOR SEQ ID NO:32:

( i ) SEQUENCE CHARACTERISTICS:
    ( A ) LENGTH: 51 amino acids
    ( B ) TYPE: amino acid
    ( D ) TOPOLOGY: linear ( i i ) MOLECULE TYPE: protein ( x i ) SEQUENCE DESCRIPTION: SEQ ID NO:32:

```
Lys Gly Leu Asp Phe Glu Lys Lys Lys Val Tyr Thr Leu Lys Val Glu
1               5                   10                  15

Ala Ser Asn Pro Tyr Val Glu Pro Arg Phe Leu Tyr Leu Gly Pro Phe
            20                  25                  30

Lys Asp Ser Ala Thr Val Arg Ile Val Val Glu Asp Val Asp Glu Pro
            35                  40                  45

Pro Ala Phe
        50
```

( 2 ) INFORMATION FOR SEQ ID NO:33:

( i ) SEQUENCE CHARACTERISTICS:
        ( A ) LENGTH: 153 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

```
AAGCCTCTGG ACTTTGAGAC CAAAAAATCC TATACTCTGA AGGTGGAGGC AGCCAATATC      60
CACATCGACC CACGTTTCAG TGGCAGGGGA CCCTTTAAAG ATACAGCAAC AGTCAAAATT     120
GTTGTAGAGG ATGCTGATGA GCCTCCGGTC TTC                                  153
```

( 2 ) INFORMATION FOR SEQ ID NO:34:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Asp Ala Leu Asp Phe Glu Thr Lys Lys Ser Tyr Thr Leu Lys Val Glu
1               5                   10                  15

Ala Ala Asn Ile His Ile Asp Pro Arg Phe Ser Gly Arg Gly Pro Phe
            20                  25                  30

Lys Asp Thr Ala Thr Val Lys Ile Val Val Glu Asp Ala Asp Glu Pro
            35                  40                  45

Pro Val Phe
        50
```

( 2 ) INFORMATION FOR SEQ ID NO:35:

( i ) SEQUENCE CHARACTERISTICS:
        ( A ) LENGTH: 152 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

```
AAGGGGGTGG ACTATGAAGC CAAAACAAGT TATACCCTGC GCATAGAAGC TGCAAATCGA      60
```

GATGCTGATC CCCGGTTTCT GAGCTTGGGT CCATTCAGTG ACACAACAAC AGTTAAGATA    120

ATTGTGGAAG ACGTGGATGA ACCCCCGTACT C    152

( 2 ) INFORMATION FOR SEQ ID NO:36:

( i ) SEQUENCE CHARACTERISTICS:
       ( A ) LENGTH: 51 amino acids
       ( B ) TYPE: amino acid
       ( D ) TOPOLOGY: linear ( i i ) MOLECULE TYPE: protein ( x i ) SEQUENCE DESCRIPTION: SEQ ID NO:36:

| Lys | Gly | Val | Asp | Tyr | Glu | Ala | Lys | Thr | Ser | Tyr | Thr | Leu | Arg | Ile | Glu |
|---|---|---|---|---|---|---|---|---|---|---|---|---|---|---|---|
| 1 |  |  |  | 5 |  |  |  |  | 10 |  |  |  |  | 15 |  |

| Ala | Ala | Asn | Arg | Asp | Ala | Asp | Pro | Arg | Phe | Leu | Ser | Leu | Gly | Pro | Phe |
|---|---|---|---|---|---|---|---|---|---|---|---|---|---|---|---|
|  |  |  | 20 |  |  |  |  | 25 |  |  |  |  | 30 |  |  |

| Ser | Asp | Thr | Thr | Thr | Val | Lys | Ile | Ile | Val | Glu | Asp | Val | Asp | Glu | Pro |
|---|---|---|---|---|---|---|---|---|---|---|---|---|---|---|---|
|  |  | 35 |  |  |  |  | 40 |  |  |  |  | 45 |  |  |  |

Pro Tyr Ser
    50

( 2 ) INFORMATION FOR SEQ ID NO:37:

( i ) SEQUENCE CHARACTERISTICS:
       ( A ) LENGTH: 153 base pairs
       ( B ) TYPE: nucleic acid
       ( C ) STRANDEDNESS: single
       ( D ) TOPOLOGY: linear ( i i ) MOLECULE TYPE: cDNA ( x i ) SEQUENCE DESCRIPTION: SEQ ID NO:37:

AAGCCACTTG ACTATGAGAA CCGAAGACTA TATACACTGA AGGTGGAGGC AGAAAATACC    60

CATGTGGATC CACGTTTTTA CTATTTAGGG CCATTCAAAG ATACAACAAT TGTAAAAATC    120

TCCATAGAAG ACGTGGATGA GCCACCCCCC TTT    153

( 2 ) INFORMATION FOR SEQ ID NO:38:

( i ) SEQUENCE CHARACTERISTICS:
       ( A ) LENGTH: 51 amino acids
       ( B ) TYPE: amino acid
       ( D ) TOPOLOGY: linear ( i i ) MOLECULE TYPE: protein ( x i ) SEQUENCE DESCRIPTION: SEQ ID NO:38:

| Lys | Pro | Leu | Asp | Tyr | Glu | Asn | Arg | Arg | Leu | Tyr | Thr | Leu | Lys | Val | Glu |
|---|---|---|---|---|---|---|---|---|---|---|---|---|---|---|---|
| 1 |  |  |  | 5 |  |  |  |  | 10 |  |  |  |  | 15 |  |

| Ala | Glu | Asn | Thr | His | Val | Asp | Pro | Arg | Phe | Tyr | Tyr | Leu | Gly | Pro | Phe |
|---|---|---|---|---|---|---|---|---|---|---|---|---|---|---|---|
|  |  |  | 20 |  |  |  |  | 25 |  |  |  |  | 30 |  |  |

| Lys | Asp | Thr | Thr | Ile | Val | Lys | Ile | Ser | Ile | Glu | Asp | Val | Asp | Glu | Pro |
|---|---|---|---|---|---|---|---|---|---|---|---|---|---|---|---|
|  |  | 35 |  |  |  |  | 40 |  |  |  |  | 45 |  |  |  |

Pro Pro Phe
    50

( 2 ) INFORMATION FOR SEQ ID NO:39:

( i ) SEQUENCE CHARACTERISTICS:
       ( A ) LENGTH: 153 base pairs
       ( B ) TYPE: nucleic acid
       ( C ) STRANDEDNESS: single
       ( D ) TOPOLOGY: linear (i i) MOLECULE TYPE: cDNA (x i) SEQUENCE DESCRIPTION: SEQ ID NO:39:

```
AGGGGTGTGG ATTATGAAAC CAAAAGAGCA TATAGCTTGA AGGTAGAGGC GGCCAATGTA        60
CACATTGATC CGAAGTTCAT CAGCAATGGA CCTTTCAAGG ACACAGTGAC TGTCAAGATT       120
GCAGTAGAAG ATGCCAATGA GCCCCCTCCC TTC                                    153
```

(2) INFORMATION FOR SEQ ID NO:40:

(i) SEQUENCE CHARACTERISTICS:
    (A) LENGTH: 51 amino acids
    (B) TYPE: amino acid
    (D) TOPOLOGY: linear (i i) MOLECULE TYPE: protein (x i) SEQUENCE DESCRIPTION: SEQ ID NO:40:

```
Arg Gly Val Asp Tyr Glu Thr Lys Arg Ala Tyr Ser Leu Lys Val Glu
 1               5                  10                      15

Ala Ala Asn Val His Ile Asp Pro Lys Phe Ile Ser Asn Gly Pro Phe
                20                  25                  30

Lys Asp Thr Val Thr Val Lys Ile Ala Val Glu Asp Ala Asn Glu Pro
            35                  40                  45

Pro Pro Phe
    50
```

(2) INFORMATION FOR SEQ ID NO:41:

(i) SEQUENCE CHARACTERISTICS:
    (A) LENGTH: 3136 base pairs
    (B) TYPE: nucleic acid
    (C) STRANDEDNESS: single
    (D) TOPOLOGY: linear (i i) MOLECULE TYPE: cDNA (x i) SEQUENCE DESCRIPTION: SEQ ID NO:41:

```
GGCACGAGCG CAAGCCGGGG AGCGCTCGGC CCAGAATTAG TGGATGGATT TGGAATCTCC        60
CTGCCTCCTC CAAGCTCCGC CACTGCCACT TTAGGCAGAG ACCTGAGCGT CAACACGCGA       120
GCCGTACTTT TAGGCTGCGG ACACTGAGCC CAGCGCGCCA GCTTCGCATC TCCGCACCAG       180
GCTCCACAGC TCGGAGAGGC ATGAACGCGA TCCGGAGGAG ACTACCCTGC GCGCGGGGAT       240
CCGTGGACAT TAGCCGCTCT CGGGAACTGA CCCCCAGCTC CTTCAGCCAT TTATGAATCC       300
AGAGGCTTGA GATTTTTTTC CGCATCCCGG AGCCCGACCT GAGAAATTTC AATGAAAAGG       360
AAAGTCAATG GATCGTGGTC TTGGAAAAGC TGCTTAGACA TGTCTGTTTC CCGGCTCTCT       420
GAACCCGTGG CAGAGCTGTA AGTAAGCGCT TCACAGTGCG TGATGAATTG GATGGCTTCG       480
GACCCGAGGC AAAAAAAATA ATTGTCTCAT TTTCGTGCTG ATTTGCTTAA CTGGTGGGAC       540
CATGCCAGAA AGGCTAGCTG AGACGCTTTT GGACCTCTGG ACTCCATTAA TAATATTATG       600
GATTACTCTT CCCTCTTTTG TGTACATGGC TCCGATGAAT CAGGCTCACG TTTTAACTAC       660
TGGATCCCCT TTGGAACTAA GCAGGCAGAG TGAAGAAATG CGGATTTTGA ACCGCTCCAA       720
AAGAGGTTGG GTTTGGAATC AAATGTTTGT TCTGGAAGAA TTTTCTGGAC CTGAACCGAT       780
TCTCGTTGGC CGGTTACACA CAGATCTGGA TCCTGGGAGC AAAAAAATCA AGTATATCCT       840
ATCGGGTGAT GGAGCCGGCA CAATCTTTCA AATAAACGAT ATAACTGGAG ACATCCATGC       900
TATCAAAAGA CTTGACCGAG AGGAAAAGGC TGAGTATACG TTAACAGCTC AGGCAGTGGA       960
CTGGGAGACA AACAAACCTC TCGAGCCTCC TTCTGAATTT ATTATTAAGG TTCAAGACAT      1020
```

| | | | | | | |
|---|---|---|---|---|---|---|
| CAACGACAAT | GCCCCCGAGT | TTCTCAATGG | ACCTTACCAT | GCTACTGTTC | CAGAGATGTC | 1080 |
| CATCTTGGGT | ACATCTGTCA | CTAATGTAAC | GGCCACTGAT | GCTGACGATC | CAGTTTATGG | 1140 |
| AAACAGTGCA | AAGTTGGTTT | ACAGTATCTT | GGAGGGACAG | CCGTATTTTT | CCATTGAGCC | 1200 |
| TGAAACAGCT | ATTATAAAAA | CTGCCCTTCC | TAACATGGAC | AGAGAGGCCA | AGGAGGAATA | 1260 |
| CCTGGTTGTA | ATTCAAGCCA | AAGATATGGG | TGGGCATTCC | GGTGGTCTGT | CTGGAACCAC | 1320 |
| GACACTCACA | GTGACGCTTA | CCGATGTGAA | TGACAATCCT | CCAAAATTTG | CTCAAAGTTT | 1380 |
| GTATCACTTC | TCAGTACCAG | AAGATGTGGT | CCTTGGCACT | GCAATAGGAA | GGGTTAAAGC | 1440 |
| CAATGACCAG | GATATTGGTG | AAAATGCACA | ATCTTCCTAT | GACATCATTG | ATGGAGATGG | 1500 |
| GACAGCACTA | TTTGAAATCA | CTTCTGATGC | CCAGGCACAG | GATGGTGTTA | TAAGACTAAG | 1560 |
| AAAGCCTCTG | GACTTTGAGA | CCAAAAAATC | CTATACTCTG | AAGGTGGAGG | CAGCCAATAT | 1620 |
| CCACATCGAC | CCACGTTTCA | GTGGCAGGGG | ACCCTTTAAA | GATACAGCAA | CAGTCAAAAT | 1680 |
| TGTTGTAGAG | GATGCTGATG | AGCCTCCGGT | CTTCTCTTCA | CCGACTTACC | TCCTTGAAGT | 1740 |
| TCATGAAAAT | GCTGCCTTGA | ACTCTGTGAT | TGGCCAAGTG | ACAGCTCGTG | ACCCTGATAT | 1800 |
| CACTTCCAGC | CCAATAAGGT | TTTCCATTGA | CCGCCACACT | GACTTGGAGA | GACAGTTCAA | 1860 |
| CATCAATGCA | GATGATGGGA | AGATAACACT | GGCGACCCCA | CTGGACAGAG | AACTAAGTGT | 1920 |
| GTGGCACAAC | ATCTCCATCA | TTGCTACTGA | GATCAGGAAC | CACAGTCAGA | TATCGCGAGT | 1980 |
| GCCTGTTGCT | ATTAAAGTGC | TGGATGTCAA | TGACAACGCC | CCTGAATTCG | CGTCCGAATA | 2040 |
| TGAGGCATTT | TTATGTGAAA | ATGGAAAACC | CGGCCAAGTC | ATTCAAACAG | TAAGCGCCAT | 2100 |
| GGACAAAGAC | GATCCCAAAA | ATGGACATTT | TTTCTTGTAC | AGTCTTCTTC | CAGAAATGGT | 2160 |
| CAACAACCCA | AATTTCACCA | TCAAGAAAAA | CGAAGATAAT | TCCCTGAGCA | TTCTGGCAAA | 2220 |
| ACATAATGGA | TTCAACCGCC | AGAAGCAAGA | AGTCTACCTT | CTGCCTATCG | TGATCAGTGA | 2280 |
| CAGTGGGAAC | CCCCCTCTGA | GTAGCACCAG | TACCCTGACC | ATCCGCGTCT | GTGGCTGTAG | 2340 |
| CAATGACGGC | GTGGTTCAGT | CGTGCAATGT | CGAAGCTTAT | GTCCTTCCTA | TTGGGCTCAG | 2400 |
| TATGGGCGCG | TTAATTGCTA | TATTAGCCTG | CATCATTTTG | CTGCTCGTCA | TTGTGGTTCT | 2460 |
| GTTCGTTACC | CTGAGGCGGC | ATAAAAATGA | ACCACTAATA | ATCAAAGATG | ATGAAGACGT | 2520 |
| TCGAGAAAAC | ATCATTCGCT | ACGACGACGA | AGGAGGCGGG | GAGGAGGACA | CAGAGGCTTT | 2580 |
| TGACATTGCA | ACTTTGCAAA | ACCCAGATGG | AATTAATGGA | TTTTTACCCC | GTAAGGATAT | 2640 |
| TAAACCAGAT | TTGCAGTTTA | TGCCAAGGCA | AGGGCTTGCT | CCAGTTCCAA | ATGGTGTTGA | 2700 |
| TGTCGATGAA | TTTATAAATG | TAAGGCTTCA | TGAGGCAGAT | AATGACCCCA | CGGCCCCACC | 2760 |
| ATATGACTCC | ATTCAGATTT | ATGGCTATGA | AGGCCGAGGG | TCTGTGGCTG | GCTCTCTCAG | 2820 |
| CTCGTTGGAG | TCCACCACAT | CAGACTCAGA | CCAGAATTTT | GACTACCTCA | GTGACTGGGG | 2880 |
| TCCCCGCTTT | AAGAGACTGG | GCGAACTCTA | CTCTGTTGGT | GAAAGTGACA | AAGAAACTTG | 2940 |
| ACAGTGGATT | ACATAAATAA | TCAATGGAAC | TGAGCATTCT | GTAATATTCT | AGGGTCACTC | 3000 |
| CCCTTAGATG | CAACAAATGT | GGCTATTTGT | TTAGAGGCA | AGTTTAGCAC | CAATCATCTA | 3060 |
| TAAACTCAAC | CACATTTTAA | TGTTGAACCA | AAAAAAATAA | TAAAAAATAA | AAAGTATATG | 3120 |
| TTAGGAGGTG | AAAAAA | | | | | 3136 |

( 2 ) INFORMATION FOR SEQ ID NO:42:

( i ) SEQUENCE CHARACTERISTICS:
        ( A ) LENGTH: 799 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Met Pro Glu Arg Leu Ala Glu Thr Leu Leu Asp Leu Trp Thr Pro Leu
 1               5                  10                  15
Ile Ile Leu Trp Ile Thr Leu Pro Ser Phe Val Tyr Met Ala Pro Met
            20                  25                  30
Asn Gln Ala His Val Leu Thr Thr Gly Ser Pro Leu Glu Leu Ser Arg
        35                  40                  45
Gln Ser Glu Glu Met Arg Ile Leu Asn Arg Ser Lys Arg Gly Trp Val
    50                  55                  60
Trp Asn Gln Met Phe Val Leu Glu Glu Phe Ser Gly Pro Glu Pro Ile
65                  70                  75                  80
Leu Val Gly Arg Leu His Thr Asp Leu Asp Pro Gly Ser Lys Lys Ile
                85                  90                  95
Lys Tyr Ile Leu Ser Gly Asp Gly Ala Gly Thr Ile Phe Gln Ile Asn
            100                 105                 110
Asp Ile Thr Gly Asp Ile His Ala Ile Lys Arg Leu Asp Arg Glu Glu
        115                 120                 125
Lys Ala Glu Tyr Thr Leu Thr Ala Gln Ala Val Asp Trp Glu Thr Asn
    130                 135                 140
Lys Pro Leu Glu Pro Pro Ser Glu Phe Ile Ile Lys Val Gln Asp Ile
145                 150                 155                 160
Asn Asp Asn Ala Pro Glu Phe Leu Asn Gly Pro Tyr His Ala Thr Val
                165                 170                 175
Pro Glu Met Ser Ile Leu Gly Thr Ser Val Thr Asn Val Thr Ala Thr
            180                 185                 190
Asp Ala Asp Asp Pro Val Tyr Gly Asn Ser Ala Lys Leu Val Tyr Ser
        195                 200                 205
Ile Leu Glu Gly Gln Pro Tyr Phe Ser Ile Glu Pro Glu Thr Ala Ile
    210                 215                 220
Ile Lys Thr Ala Leu Pro Asn Met Asp Arg Glu Ala Lys Glu Glu Tyr
225                 230                 235                 240
Leu Val Val Ile Gln Ala Lys Asp Met Gly Gly His Ser Gly Gly Leu
                245                 250                 255
Ser Gly Thr Thr Thr Leu Thr Val Thr Leu Thr Asp Val Asn Asp Asn
            260                 265                 270
Pro Pro Lys Phe Ala Gln Ser Leu Tyr His Phe Ser Val Pro Glu Asp
        275                 280                 285
Val Val Leu Gly Thr Ala Ile Gly Arg Val Lys Ala Asn Asp Gln Asp
    290                 295                 300
Ile Gly Glu Asn Ala Gln Ser Ser Tyr Asp Ile Ile Asp Gly Asp Gly
305                 310                 315                 320
Thr Ala Leu Phe Glu Ile Thr Ser Asp Ala Gln Ala Gln Asp Gly Val
                325                 330                 335
Ile Arg Leu Arg Lys Pro Leu Asp Phe Glu Thr Lys Lys Ser Tyr Thr
            340                 345                 350
Leu Lys Val Glu Ala Ala Asn Ile His Ile Asp Pro Arg Phe Ser Gly
        355                 360                 365
Arg Gly Pro Phe Lys Asp Thr Ala Thr Val Lys Ile Val Val Glu Asp
    370                 375                 380
Ala Asp Glu Pro Pro Val Phe Ser Ser Pro Thr Tyr Leu Leu Glu Val
385                 390                 395                 400
```

| | | | | | | | | | | | | | | |
|---|---|---|---|---|---|---|---|---|---|---|---|---|---|---|
|His|Glu|Asn|Ala|Ala|Leu|Asn|Ser|Val|Ile|Gly|Gln|Val|Thr|Ala|Arg|
| | | | |405| | | | |410| | | |415| | |
|Asp|Pro|Asp|Ile|Thr|Ser|Ser|Pro|Ile|Arg|Phe|Ser|Ile|Asp|Arg|His|
| | | |420| | | |425| | | |430| | | | |
|Thr|Asp|Leu|Glu|Arg|Gln|Phe|Asn|Ile|Asn|Ala|Asp|Asp|Gly|Lys|Ile|
| | |435| | | |440| | | |445| | | | | |
|Thr|Leu|Ala|Thr|Pro|Leu|Asp|Arg|Glu|Leu|Ser|Val|Trp|His|Asn|Ile|
| |450| | | |455| | | |460| | | | | | |
|Ser|Ile|Ile|Ala|Thr|Glu|Ile|Arg|Asn|His|Ser|Gln|Ile|Ser|Arg|Val|
|465| | | |470| | | |475| | | |480| | | |

His Glu Asn Ala Ala Leu Asn Ser Val Ile Gly Gln Val Thr Ala Arg
                405                 410                 415
Asp Pro Asp Ile Thr Ser Ser Pro Ile Arg Phe Ser Ile Asp Arg His
            420             425             430
Thr Asp Leu Glu Arg Gln Phe Asn Ile Asn Ala Asp Asp Gly Lys Ile
        435             440             445
Thr Leu Ala Thr Pro Leu Asp Arg Glu Leu Ser Val Trp His Asn Ile
    450             455             460
Ser Ile Ile Ala Thr Glu Ile Arg Asn His Ser Gln Ile Ser Arg Val
465             470             475             480
Pro Val Ala Ile Lys Val Leu Asp Val Asn Asp Asn Ala Pro Glu Phe
            485             490             495
Ala Ser Glu Tyr Glu Ala Phe Leu Cys Glu Asn Gly Lys Pro Gly Gln
        500             505             510
Val Ile Gln Thr Val Ser Ala Met Asp Lys Asp Asp Pro Lys Asn Gly
        515             520             525
His Phe Phe Leu Tyr Ser Leu Leu Pro Glu Met Val Asn Asn Pro Asn
    530             535             540
Phe Thr Ile Lys Lys Asn Glu Asp Asn Ser Leu Ser Ile Leu Ala Lys
545             550             555             560
His Asn Gly Phe Asn Arg Gln Lys Gln Glu Val Tyr Leu Leu Pro Ile
            565             570             575
Val Ile Ser Asp Ser Gly Asn Pro Pro Leu Ser Ser Thr Ser Thr Leu
        580             585             590
Thr Ile Arg Val Cys Gly Cys Ser Asn Asp Gly Val Val Gln Ser Cys
        595             600             605
Asn Val Glu Ala Tyr Val Leu Pro Ile Gly Leu Ser Met Gly Ala Leu
    610             615             620
Ile Ala Ile Leu Ala Cys Ile Ile Leu Leu Leu Val Ile Val Val Leu
625             630             635             640
Phe Val Thr Leu Arg Arg His Lys Asn Glu Pro Leu Ile Ile Lys Asp
            645             650             655
Asp Glu Asp Val Arg Glu Asn Ile Ile Arg Tyr Asp Asp Glu Gly Gly
            660             665             670
Gly Glu Glu Asp Thr Glu Ala Phe Asp Ile Ala Thr Leu Gln Asn Pro
        675             680             685
Asp Gly Ile Asn Gly Phe Leu Pro Arg Lys Asp Ile Lys Pro Asp Leu
    690             695             700
Gln Phe Met Pro Arg Gln Gly Leu Ala Pro Val Pro Asn Gly Val Asp
705             710             715             720
Val Asp Glu Phe Ile Asn Val Arg Leu His Glu Ala Asp Asn Asp Pro
            725             730             735
Thr Ala Pro Pro Tyr Asp Ser Ile Gln Ile Tyr Gly Tyr Glu Gly Arg
            740             745             750
Gly Ser Val Ala Gly Ser Leu Ser Ser Leu Glu Ser Thr Thr Ser Asp
        755             760             765
Ser Asp Gln Asn Phe Asp Tyr Leu Ser Asp Trp Gly Pro Arg Phe Lys
    770             775             780
Arg Leu Gly Glu Leu Tyr Ser Val Gly Glu Ser Asp Lys Glu Thr
785             790             795

( 2 ) INFORMATION FOR SEQ ID NO:43:

( i ) SEQUENCE CHARACTERISTICS:
        ( A ) LENGTH: 3043 base pairs ( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:43:

| | | | | | | |
|---|---|---|---|---|---|---|
| GGCACGAGCG | CAAGCCGGGG | AGCGCTCGGC | CCAGAATTAG | TGGATGGATT | TGGAATCTCC | 60 |
| CTGCCTCCTC | CAAGCTCCGC | CACTGCCACT | TTAGGCAGAG | ACCTGAGCGT | CAACACGCGA | 120 |
| GCCGTACTTT | TAGGCTGCGG | ACACTGAGCC | CAGCGCGCCA | GCTTCGCATC | TCCGCACCAG | 180 |
| GCTCCACAGC | TCGGAGAGGC | ATGAACGCGA | TCCGGAGGAG | ACTACCCTGC | GCGCGGGGAT | 240 |
| CCGTGGACAT | TAGCCGCTCT | CGGGAACTGA | CCCCCAGCTC | CTTCAGCCAT | TTATGAATCC | 300 |
| AGAGGCTTGA | GATTTTTTTC | CGCATCCCGG | AGCCCGACCT | GAGAAATTTC | AATGAAAAGG | 360 |
| AAAGTCAATG | GATCGTGGTC | TTGGAAAAGC | TGCTTAGACA | TGTCTGTTTC | CCGGCTCTCT | 420 |
| GAACCCGTGG | CAGAGCTGTA | AGTAAGCGCT | TCACAGTGCG | TGATGAATTG | GATGGCTTCG | 480 |
| GACCCGAGGC | AAAAAAAATA | ATTGTCTCAT | TTTCGTGCTG | ATTTGCTTAA | CTGGTGGGAC | 540 |
| CATGCCAGAA | AGGCTAGCTG | AGACGCTTTT | GGACCTCTGG | ACTCCATTAA | TAATATTATG | 600 |
| GATTACTCTT | CCCTCTTTTG | TGTACATGGC | TCCGATGAAT | CAGGCTCACG | TTTTAACTAC | 660 |
| TGGATCCCCT | TTGGAACTAA | GCAGGCAGAG | TGAAGAAATG | CGGATTTTGA | ACCGCTCCAA | 720 |
| AAGAGGTTGG | GTTTGGAATC | AAATGTTTGT | TCTGGAAGAA | TTTTCTGGAC | CTGAACCGAT | 780 |
| TCTCGTTGGC | CGGTTACACA | CAGATCTGGA | TCCTGGGAGC | AAAAAAATCA | AGTATATCCT | 840 |
| ATCGGGTGAT | GGAGCCGGCA | CAATCTTTCA | AATAAACGAT | ATAACTGGAG | ACATCCATGC | 900 |
| TATCAAAAGA | CTTGACCGAG | AGGAAAGGC | TGAGTATACG | TTAACAGCTC | AGGCAGTGGA | 960 |
| CTGGGAGACA | AACAAACCTC | TCGAGCCTCC | TTCTGAATTT | ATTATTAAGG | TTCAAGACAT | 1020 |
| CAACGACAAT | GCCCCCGAGT | TTCTCAATGG | ACCTTACCAT | GCTACTGTTC | AGAGATGTC | 1080 |
| CATCTTGGGT | ACATCTGTCA | CTAATGTAAC | GGCCACTGAT | GCTGACGATC | CAGTTTATGG | 1140 |
| AAACAGTGCA | AAGTTGGTTT | ACAGTATCTT | GGAGGGACAG | CCGTATTTTT | CCATTGAGCC | 1200 |
| TGAAACAGCT | ATTATAAAAA | CTGCCCTTCC | TAACATGGAC | AGAGAGGCCA | AGGAGGAATA | 1260 |
| CCTGGTTGTA | ATTCAAGCCA | AGATATGGG | TGGGCATTCC | GGTGGTCTGT | CTGGAACCAC | 1320 |
| GACACTCACA | GTGACGCTTA | CCGATGTGAA | TGACAATCCT | CCAAAATTTG | CTCAAAGTTT | 1380 |
| GTATCACTTC | TCAGTACCAG | AAGATGTGGT | CCTTGGCACT | GCAATAGGAA | GGGTTAAAGC | 1440 |
| CAATGACCAG | GATATTGGTG | AAAATGCACA | ATCTTCCTAT | GACATCATTG | ATGGAGATGG | 1500 |
| GACAGCACTA | TTTGAAATCA | CTTCTGATGC | CCAGGCACAG | GATGGTGTTA | TAAGACTAAG | 1560 |
| AAAGCCTCTG | GACTTTGAGA | CCAAAAAATC | CTATACTCTG | AAGGTGGAGG | CAGCCAATAT | 1620 |
| CCACATCGAC | CCACGTTTCA | GTGGCAGGGG | ACCCTTTAAA | GATACAGCAA | CAGTCAAAAT | 1680 |
| TGTTGTAGAG | GATGCTGATG | AGCCTCCGGT | CTTCTCTTCA | CCGACTTACC | TCCTTGAAGT | 1740 |
| TCATGAAAAT | GCTGCCTTGA | ACTCTGTGAT | TGGCCAAGTG | ACAGCTCGTG | ACCCTGATAT | 1800 |
| CACTTCCAGC | CCAATAAGGT | TTTCCATTGA | CCGCCACACT | GACTTGGAGA | GACAGTTCAA | 1860 |
| CATCAATGCA | GATGATGGGA | AGATAACACT | GGCGACCCCA | CTGGACAGAG | AACTAAGTGT | 1920 |
| GTGGCACAAC | ATCTCCATCA | TTGCTACTGA | GATCAGGAAC | CACAGTCAGA | TATCGCGAGT | 1980 |
| GCCTGTTGCT | ATTAAAGTGC | TGGATGTCAA | TGACAACGCC | CTGAATTCG | CGTCCGAATA | 2040 |
| TGAGGCATTT | TTATGTGAAA | ATGGAAAACC | CGGCCAAGTA | AATATCTCCA | TGTTGTTAAT | 2100 |
| ACTGAATATG | TTTGTATACA | ACTGTTTCCT | AGTTAATTAA | CCTGCATTAC | TTCCTGATTT | 2160 |

-continued

| | | | | | |
|---|---|---|---|---|---|
| TGCATTGGTT | GGATTTACAA | AGTCACAGGC | AGGAAACTCC | TCCAAGCGGT | AACAGAAGGG | 2220
| AATATTTGTC | TTTCTCAGAT | GTTAATTCTC | TTCTAACTTA | GGAACCAATT | GGCTCAGAAA | 2280
| GTGTGATGAT | CTGCTCTGCT | CTGACCCCAG | CCAAATCACT | GTCTTAAAAT | ACATCACATA | 2340
| TGGGTGATGG | CTGGGGACAG | TCTTACAGTG | CAGAAGGTTG | AAATCGCCAT | CAATTGGCAA | 2400
| GAATCTAAAG | AATAGCTCAT | GGAAGCATG | CATTTTTGTT | TTATGTTGAA | AAGAAGATTA | 2460
| ATGCACAAAT | GTGGAATGCA | AAAAAACACA | GTAGTTTATA | GAAAGCTCTA | TGTAGTGGTA | 2520
| CTTATGTCTG | TACACATATT | TGCAAGTTTA | GTAAACATAA | TGTAGACATC | AAATTGTTAG | 2580
| ATATGCCCCT | AAGGCATTTC | AATATGTAGA | GGTAAGACTC | CTAAGGCATA | GATGGGGATA | 2640
| ATGAAGACAA | AAATAAAGGG | CAGAAAAATG | TATAAAATAG | AACAGACAGA | AATACACTAA | 2700
| AGATCTAAAG | ATAGAAGCAG | GAAAGAGGGG | AGGGAGGGAG | GGAGACAGGG | CTGGAAGAAG | 2760
| ATAGGGTGGG | AGGGAGGGAA | GGAGAGTCAA | GGCTCAGGGT | GTGGGGGGGA | AGGTAAAATG | 2820
| CAAAACAAAA | TCTACAGAAA | CCACTATACT | CTGAATGTCA | AAATGCAACT | AACCTATGTA | 2880
| AAATCACCCA | ACCACATGTG | TAATAGATTT | ATTTTAACGA | GGTGCCGGAG | TACTGTATGT | 2940
| TTAAGAAATT | TATCATTTTT | CAACTTCCTA | ATTTATTTCT | GGATGGTGAC | ATTTTAATTT | 3000
| AAATAAACAG | CAGCTGACAG | CATGAAAAAA | AAAAAAAAAA | AAA | | 3043

( 2 ) INFORMATION FOR SEQ ID NO:44:

( i ) SEQUENCE CHARACTERISTICS:
        ( A ) LENGTH: 532 amino acids
        ( B ) TYPE: amino acid
        ( D ) TOPOLOGY: linear ( i i ) MOLECULE TYPE: protein ( x i ) SEQUENCE DESCRIPTION: SEQ ID NO:44:

```
Met Pro Glu Arg Leu Ala Glu Thr Leu Leu Asp Leu Trp Thr Pro Leu
 1               5                  10                  15

Ile Ile Leu Trp Ile Thr Leu Pro Ser Phe Val Tyr Met Ala Pro Met
            20                  25                  30

Asn Gln Ala His Val Leu Thr Thr Gly Ser Pro Leu Glu Leu Ser Arg
        35                  40                  45

Gln Ser Glu Glu Met Arg Ile Leu Asn Arg Ser Lys Arg Gly Trp Val
    50                  55                  60

Trp Asn Gln Met Phe Val Leu Glu Glu Phe Ser Gly Pro Glu Pro Ile
65                  70                  75                  80

Leu Val Gly Arg Leu His Thr Asp Leu Asp Pro Gly Ser Lys Lys Ile
                85                  90                  95

Lys Tyr Ile Leu Ser Gly Asp Gly Ala Gly Thr Ile Phe Gln Ile Asn
            100                 105                 110

Asp Ile Thr Gly Asp Ile His Ala Ile Lys Arg Leu Asp Arg Glu Glu
        115                 120                 125

Lys Ala Glu Tyr Thr Leu Thr Ala Gln Ala Val Asp Trp Glu Thr Asn
    130                 135                 140

Lys Pro Leu Glu Pro Pro Ser Glu Phe Ile Ile Lys Val Gln Asp Ile
145                 150                 155                 160

Asn Asp Asn Ala Pro Glu Phe Leu Asn Gly Pro Tyr His Ala Thr Val
                165                 170                 175

Pro Glu Met Ser Ile Leu Gly Thr Ser Val Thr Asn Val Thr Ala Thr
            180                 185                 190

Asp Ala Asp Asp Pro Val Tyr Gly Asn Ser Ala Lys Leu Val Tyr Ser
        195                 200                 205
```

```
Ile  Leu  Glu  Gly  Gln  Pro  Tyr  Phe  Ser  Ile  Glu  Pro  Glu  Thr  Ala  Ile
     210                      215                      220

Ile  Lys  Thr  Ala  Leu  Pro  Asn  Met  Asp  Arg  Glu  Ala  Lys  Glu  Glu  Tyr
225                      230                      235                      240

Leu  Val  Val  Ile  Gln  Ala  Lys  Asp  Met  Gly  Gly  His  Ser  Gly  Gly  Leu
                    245                      250                      255

Ser  Gly  Thr  Thr  Thr  Leu  Thr  Val  Thr  Leu  Thr  Asp  Val  Asn  Asp  Asn
               260                      265                      270

Pro  Pro  Lys  Phe  Ala  Gln  Ser  Leu  Tyr  His  Phe  Ser  Val  Pro  Glu  Asp
          275                      280                      285

Val  Val  Leu  Gly  Thr  Ala  Ile  Gly  Arg  Val  Lys  Ala  Asn  Asp  Gln  Asp
     290                      295                      300

Ile  Gly  Glu  Asn  Ala  Gln  Ser  Ser  Tyr  Asp  Ile  Ile  Asp  Gly  Asp  Gly
305                      310                      315                      320

Thr  Ala  Leu  Phe  Glu  Ile  Thr  Ser  Asp  Ala  Gln  Ala  Gln  Asp  Gly  Val
                    325                      330                      335

Ile  Arg  Leu  Arg  Lys  Pro  Leu  Asp  Phe  Glu  Thr  Lys  Lys  Ser  Tyr  Thr
               340                      345                      350

Leu  Lys  Val  Glu  Ala  Ala  Asn  Ile  His  Ile  Asp  Pro  Arg  Phe  Ser  Gly
          355                      360                      365

Arg  Gly  Pro  Phe  Lys  Asp  Thr  Ala  Thr  Val  Lys  Ile  Val  Val  Glu  Asp
     370                      375                      380

Ala  Asp  Glu  Pro  Pro  Val  Phe  Ser  Ser  Pro  Thr  Tyr  Leu  Leu  Glu  Val
385                      390                      395                      400

His  Glu  Asn  Ala  Ala  Leu  Asn  Ser  Val  Ile  Gly  Gln  Val  Thr  Ala  Arg
                    405                      410                      415

Asp  Pro  Asp  Ile  Thr  Ser  Ser  Pro  Ile  Arg  Phe  Ser  Ile  Asp  Arg  His
               420                      425                      430

Thr  Asp  Leu  Glu  Arg  Gln  Phe  Asn  Ile  Asn  Ala  Asp  Asp  Gly  Lys  Ile
          435                      440                      445

Thr  Leu  Ala  Thr  Pro  Leu  Asp  Arg  Glu  Leu  Ser  Val  Trp  His  Asn  Ile
     450                      455                      460

Ser  Ile  Ile  Ala  Thr  Glu  Ile  Arg  Asn  His  Ser  Gln  Ile  Ser  Arg  Val
465                      470                      475                      480

Pro  Val  Ala  Ile  Lys  Val  Leu  Asp  Val  Asn  Asp  Asn  Ala  Pro  Glu  Phe
                    485                      490                      495

Ala  Ser  Glu  Tyr  Glu  Ala  Phe  Leu  Cys  Glu  Asn  Gly  Lys  Pro  Gly  Gln
               500                      505                      510

Val  Asn  Ile  Ser  Met  Leu  Leu  Ile  Leu  Asn  Met  Phe  Val  Tyr  Asn  Cys
          515                      520                      525

Phe  Leu  Val  Asn
     530
```

( 2 ) INFORMATION FOR SEQ ID NO:45:

( i ) SEQUENCE CHARACTERISTICS:
        ( A ) LENGTH: 2490 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:45:

```
GGCACGAGGG  CCAGTTGAGC  CAGAGTCAGA  ATTTGTGATC  AAAATTCACG  ATATCAACGA      60

CAATGAGCCT  ACATTCCCAG  AAGAAATTTA  TACAGCCAGC  GTTCCTGAAA  TGTCTGTTGT     120
```

| | | | | | |
|---|---|---|---|---|---|
| AGGTACTTCT | GTGGTGCAAG | TCACAGCTAC | AGATGCCGAT | GACCCTTCAT | ATGGAAACAG | 180
| CGCCAGAGTC | ATTTACAGCA | TACTTCAAGG | GCAGCCTTAT | TTCTCTGTGG | AACCAGAAAC | 240
| AGGTATCATA | AGGACAGCTC | TACCAAACAT | GAACAGAGAG | AACAAGGAAC | AGTACCAGGT | 300
| GGTTATTCAA | GCCAAGGACA | TGGGCGGTCA | GATGGGGGGT | CTGTCTGGAA | CCACCACAGT | 360
| GAACATCACT | CTCACAGATG | TCAACGACAA | TCCTCCTCGC | TTCCCCAAA | ACACCATCCA | 420
| TCTGCGAGTT | CTTGAATCCT | CTCCAGTTGG | CACAGCTGTG | GGAAGTGTAA | AAGCCACCGA | 480
| TGCTGACACG | GGGAAAAATG | CCGAAGTGGA | TTACCGCATT | ATTGATGGAG | ATGGCACAGA | 540
| TATGTTTGAC | ATTATAACTG | AGAAGGACAC | ACAGGAAGGC | ATCATCACTG | TGAAAAAGCC | 600
| ACTTGACTAT | GAGAACCGAA | GACTATATAC | TCTGAAGGTG | GAGGCAGAAA | ATACCCATGT | 660
| GGATCCACGT | TTTTACTATT | TAGGGCCATT | CAAAGATACA | ACAATTGTAA | AAATCTCCAT | 720
| AGAAGACGTG | GATGAGCCTC | CAGTTTTCAG | TCGATCCTCC | TATCTGTTTG | AGGTTCATGA | 780
| GGATATTGAA | GTGGGCACAA | TCATCGGTAC | TGTAATGGCA | AGAGACCCAG | ATTCTACTTC | 840
| CAGTCCCATC | AGATTTACTT | TAGATCGCCA | TACTGATCTT | GACAGGATCT | TAACATTCA | 900
| TTCTGGAAAC | GGATCACTTT | ATACATCAAA | GCCACTTGAT | CGTGAACTAT | CTCAATGGCA | 960
| CAACCTTACC | GTCATAGCTG | CCGAGATCAA | TAATCCTAAA | GAAACAACTC | GTGTGTCTGT | 1020
| TTTTGTGAGG | ATTTTGGATG | TTAATGACAA | CGCTCCACAA | TTTGCTGTGT | TTTATGACAC | 1080
| ATTTGTATGT | GAAAATGCCA | GACCAGGACA | GCTGATACAG | ACAATAAGTG | CAGTTGACAA | 1140
| AGATGACCCC | TTAGGTGGAC | AGAAGTTCTT | CTTCAGTTTG | GCTGCTGTGA | ATCCTAACTT | 1200
| CACAGTGCAA | GACAATGAAG | ACAACACTGC | CAGAATTTTA | ACCAGAAAGA | ATGGCTTCAA | 1260
| CCGTCATGAA | ATAAGCACCT | ACCTACTGCC | GGTAGTGATA | TCTGATAATG | ACTACCCCAT | 1320
| TCAGAGCAGC | ACTGGCACCC | TGACGATCCG | TGTTTGCGCC | TGTGACAGCC | AGGGCAACAT | 1380
| GCAGTCCTGC | AGTGCCGAAG | CCCTGCTCCT | TCCTGCTGGC | CTCAGCACTG | GCGCCTTGAT | 1440
| CGCCATTCTT | CTCTGCATCA | TCATTCTGCT | GGTTATAGTA | GTCCTCTTTG | CAGCCCTGAA | 1500
| AAGGCAACGG | AAGAAAGAGC | CTCTGATTTT | ATCCAAAGAA | GACATCAGAG | ACAACATTGT | 1560
| GAGCTATAAC | GACGAAGGTG | GCGGAGAGGA | GGACACCCAA | CCCTTTGATA | TTGGAACCCT | 1620
| GAGGAATCCT | GCAGCTATCG | AGGAGAAAAA | GCTGCGGCGA | GATATCATTC | CTGAAACGTT | 1680
| ATTTATACCG | CGGCGGACTC | CTACGGCCCC | GGATAACACG | GATGTCCGGG | ATTTCATTAA | 1740
| TGAGCGCCTC | AAAGAGCACG | ACTTGGACCC | CACTGCGCCT | CCCTACGACT | CGCTGGCTAC | 1800
| CTATGCCTAT | GAAGGAAACG | ACTCTGTTGC | TGAATCTCTG | AGCTCCTTAG | AATCAGGTAC | 1860
| CACTGAAGGA | GACCAAAACT | ACGATTACCT | TCGAGAATGG | GGGCCTCGGT | TTAATAAACT | 1920
| AGCAGAAATG | TACGGTGGTG | GTGAGAGCGA | CAAAGACGCT | TAGCCTGGCC | CCTGAGCTCT | 1980
| GTTCAACGAG | ATACGTAACT | TTGCAGACAT | TGTCTCCACT | TCACAATATT | TGATATTCAG | 2040
| GAGAAAAAAT | TCCTGCCACT | CAGCACAAGT | TTCCCACCTA | TTTCTTAATT | TGTTCATTAA | 2100
| TTATATTAAT | TCCTTCCTGT | AGAATGTCTC | ATGGGATATA | TACGACATTT | TATTTAATCA | 2160
| CTTCCAAGAG | CCAAAGCTAT | GGAAATTCAA | TGTTGCCCAT | CTTAGTAAAT | AAAAGAAACC | 2220
| CGAGCAGGAT | AGTTCTCCCT | TAAGCAACCT | CACGAACAAG | TCGCTTCTGT | TAGATACACG | 2280
| TCTTGCCCTT | GCAAATGAAG | CTTTGAAAAG | ACGAAGAAAA | CATTTAAGAT | GTATCCTGTT | 2340
| CTGTACATTA | AGTTTAAAAA | AAAAAGTCCA | TGTGGTGTTA | GTAGGTGTGA | TATGCAGCCT | 2400
| GGTATACGAG | CATTCGTGCA | ATTTCATTTC | ATCAAATTCT | ATCTGCTAAT | GTTTTATATT | 2460
| TATATTTTTG | TATTTATTTT | TTAAAAAAAA | | | | 2490

( 2 ) INFORMATION FOR SEQ ID NO:46:

( i ) SEQUENCE CHARACTERISTICS:
        ( A ) LENGTH: 653 amino acids
        ( B ) TYPE: amino acid
        ( D ) TOPOLOGY: linear ( i i ) MOLECULE TYPE: protein ( x i ) SEQUENCE DESCRIPTION: SEQ ID NO:46:

```
Ala Arg Gly Pro Val Glu Pro Glu Ser Glu Phe Val Ile Lys Ile His
 1               5                  10                      15

Asp Ile Asn Asp Asn Glu Pro Thr Phe Pro Glu Glu Ile Tyr Thr Ala
             20                  25                  30

Ser Val Pro Glu Met Ser Val Val Gly Thr Ser Val Val Gln Val Thr
         35                  40                  45

Ala Thr Asp Ala Asp Pro Ser Tyr Gly Asn Ser Ala Arg Val Ile
     50                  55                  60

Tyr Ser Ile Leu Gln Gly Gln Pro Tyr Phe Ser Val Glu Pro Glu Thr
 65                  70                  75                  80

Gly Ile Ile Arg Thr Ala Leu Pro Asn Met Asn Arg Glu Asn Lys Glu
                 85                  90                  95

Gln Tyr Gln Val Val Ile Gln Ala Lys Asp Met Gly Gly Gln Met Gly
            100                 105                 110

Gly Leu Ser Gly Thr Thr Thr Val Asn Ile Thr Leu Thr Asp Val Asn
            115                 120                 125

Asp Asn Pro Pro Arg Phe Pro Gln Asn Thr Ile His Leu Arg Val Leu
        130                 135                 140

Glu Ser Ser Pro Val Gly Thr Ala Val Gly Ser Val Lys Ala Thr Asp
145                 150                 155                 160

Ala Asp Thr Gly Lys Asn Ala Glu Val Asp Tyr Arg Ile Ile Asp Gly
                165                 170                 175

Asp Gly Thr Asp Met Phe Asp Ile Ile Thr Glu Lys Asp Thr Gln Glu
            180                 185                 190

Gly Ile Ile Thr Val Lys Lys Pro Leu Asp Tyr Glu Asn Arg Arg Leu
            195                 200                 205

Tyr Thr Leu Lys Val Glu Ala Glu Asn Thr His Val Asp Pro Arg Phe
210                 215                 220

Tyr Tyr Leu Gly Pro Phe Lys Asp Thr Thr Ile Val Lys Ile Ser Ile
225                 230                 235                 240

Glu Asp Val Asp Glu Pro Pro Val Phe Ser Arg Ser Ser Tyr Leu Phe
            245                 250                 255

Glu Val His Glu Asp Ile Glu Val Gly Thr Ile Ile Gly Thr Val Met
            260                 265                 270

Ala Arg Asp Pro Asp Ser Thr Ser Ser Pro Ile Arg Phe Thr Leu Asp
        275                 280                 285

Arg His Thr Asp Leu Asp Arg Ile Phe Asn Ile His Ser Gly Asn Gly
    290                 295                 300

Ser Leu Tyr Thr Ser Lys Pro Leu Asp Arg Glu Leu Ser Gln Trp His
305                 310                 315                 320

Asn Leu Thr Val Ile Ala Ala Glu Ile Asn Asn Pro Lys Glu Thr Thr
                325                 330                 335

Arg Val Ser Val Phe Val Arg Ile Leu Asp Val Asn Asp Asn Ala Pro
            340                 345                 350

Gln Phe Ala Val Phe Tyr Asp Thr Phe Val Cys Glu Asn Ala Arg Pro
```

|     |     |     |     | 355 |     |     |     |     | 360 |     |     |     |     | 365 |
| --- | --- | --- | --- | --- | --- | --- | --- | --- | --- | --- | --- | --- | --- | --- |
| Gly | Gln | Leu | Ile | Gln | Thr | Ile | Ser | Ala | Val | Asp | Lys | Asp | Asp | Pro | Leu |
|     |     | 370 |     |     |     | 375 |     |     |     | 380 |     |     |     |     |     |
| Gly | Gly | Gln | Lys | Phe | Phe | Phe | Ser | Leu | Ala | Ala | Val | Asn | Pro | Asn | Phe |
| 385 |     |     |     |     | 390 |     |     |     |     | 395 |     |     |     |     | 400 |
| Thr | Val | Gln | Asp | Asn | Glu | Asp | Asn | Thr | Ala | Arg | Ile | Leu | Thr | Arg | Lys |
|     |     |     |     | 405 |     |     |     |     | 410 |     |     |     |     | 415 |     |
| Asn | Gly | Phe | Asn | Arg | His | Glu | Ile | Ser | Thr | Tyr | Leu | Leu | Pro | Val | Val |
|     |     |     | 420 |     |     |     | 425 |     |     |     |     |     | 430 |     |     |
| Ile | Ser | Asp | Asn | Asp | Tyr | Pro | Ile | Gln | Ser | Ser | Thr | Gly | Thr | Leu | Thr |
|     |     | 435 |     |     |     |     | 440 |     |     |     |     | 445 |     |     |     |
| Ile | Arg | Val | Cys | Ala | Cys | Asp | Ser | Gln | Gly | Asn | Met | Gln | Ser | Cys | Ser |
|     | 450 |     |     |     |     | 455 |     |     |     |     | 460 |     |     |     |     |
| Ala | Glu | Ala | Leu | Leu | Leu | Pro | Ala | Gly | Leu | Ser | Thr | Gly | Ala | Leu | Ile |
| 465 |     |     |     |     | 470 |     |     |     |     | 475 |     |     |     |     | 480 |
| Ala | Ile | Leu | Leu | Cys | Ile | Ile | Ile | Leu | Leu | Val | Ile | Val | Val | Leu | Phe |
|     |     |     |     | 485 |     |     |     |     | 490 |     |     |     |     | 495 |     |
| Ala | Ala | Leu | Lys | Arg | Gln | Arg | Lys | Lys | Glu | Pro | Leu | Ile | Leu | Ser | Lys |
|     |     |     | 500 |     |     |     |     | 505 |     |     |     |     | 510 |     |     |
| Glu | Asp | Ile | Arg | Asp | Asn | Ile | Val | Ser | Tyr | Asn | Asp | Glu | Gly | Gly | Gly |
|     |     | 515 |     |     |     |     | 520 |     |     |     |     | 525 |     |     |     |
| Glu | Glu | Asp | Thr | Gln | Pro | Phe | Asp | Ile | Gly | Thr | Leu | Arg | Asn | Pro | Ala |
|     | 530 |     |     |     |     | 535 |     |     |     |     | 540 |     |     |     |     |
| Ala | Ile | Glu | Glu | Lys | Lys | Leu | Arg | Arg | Asp | Ile | Ile | Pro | Glu | Thr | Leu |
| 545 |     |     |     |     | 550 |     |     |     |     | 555 |     |     |     |     | 560 |
| Phe | Ile | Pro | Arg | Arg | Thr | Pro | Thr | Ala | Pro | Asp | Asn | Thr | Asp | Val | Arg |
|     |     |     |     | 565 |     |     |     |     | 570 |     |     |     |     | 575 |     |
| Asp | Phe | Ile | Asn | Glu | Arg | Leu | Lys | Glu | His | Asp | Leu | Asp | Pro | Thr | Ala |
|     |     |     | 580 |     |     |     |     | 585 |     |     |     |     | 590 |     |     |
| Pro | Pro | Tyr | Asp | Ser | Leu | Ala | Thr | Tyr | Ala | Tyr | Glu | Gly | Asn | Asp | Ser |
|     |     | 595 |     |     |     |     | 600 |     |     |     |     | 605 |     |     |     |
| Val | Ala | Glu | Ser | Leu | Ser | Ser | Leu | Glu | Ser | Gly | Thr | Thr | Glu | Gly | Asp |
|     | 610 |     |     |     |     | 615 |     |     |     |     | 620 |     |     |     |     |
| Gln | Asn | Tyr | Asp | Tyr | Leu | Arg | Glu | Trp | Gly | Pro | Arg | Phe | Asn | Lys | Leu |
| 625 |     |     |     |     | 630 |     |     |     |     | 635 |     |     |     |     | 640 |
| Ala | Glu | Met | Tyr | Gly | Gly | Gly | Glu | Ser | Asp | Lys | Asp | Ala |     |     |     |
|     |     |     |     | 645 |     |     |     |     | 650 |     |     |     |     |     |     |

( 2 ) INFORMATION FOR SEQ ID NO:47:

( i ) SEQUENCE CHARACTERISTICS:
        ( A ) LENGTH: 3048 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:47:

```
CGCCGGCGGG GAAGATGACC GCGGGCGCCG GCGTGCTCCT TCTGCTGCTC TCGCTCTCCG        60

GCGCGCTCCG GGCCCATAAT GAGGATCTTA CAACTAGAGA GACCTGCAAG GCTGGGTTCT       120

CTGAAGATGA TTACACGGCA TTAATCTCCC AAAATATTCT AGAAGGGGAA AAGCTACTTC       180

AAGTCAAGTT CAGCAGCTGT GTGGGGACCA AGGGGACACA ATATGAGACC AACAGCATGG       240

ACTTCAAAGT TGGGGCAGAT GGGACAGTCT TCGCCACCCG GGAGCTGCAG GTCCCCTCCG       300

AGCAGGTGGC GTTCACGGTG ACTGCATGGG ACAGCCAGAC AGCAGAGAAA TGGGACGCCG       360
```

```
TGGTGCGGTT GCTGGTGGCC CAGACCTCGT CCCCGCACTC TGGACACAAG CCGCAGAAAG      420
GAAAGAAGGT CGTGGCTCTG GACCCCTCTC CGCCTCCGAA GGACACCCTG CTGCCGTGGC      480
CCCAGCACCA GAACGCCAAC GGGCTGAGGC GGCGCAAACG GGACTGGGTC ATCCCACCCA      540
TCAACGTGCC CGAGAACTCG CGCGGGCCCT TCCCGCAGCA GCTCGTGAGG ATCCGGTCCG      600
ACAAAGACAA TGACATCCCC ATCCGGTACA GCATCACGGG AGTGGGTGCC GACCAGCCCC      660
CCATGGAGGT CTTCAGCATT AACTCCATGT CCGGCCGGAT GTACGTCACA AGGCCCATGG      720
ACCGGGAGGA GCACGCCTCT TACCACCTCC GAGCCCACGC TGTGGACATG AATGGCAACA      780
AGGTGGAGAA CCCCATCGAC CTGTACATCT ACGTCATCGA CATGAATGAC AACCACCCTG      840
AGTTCATCAA CCAGGTCTAC AACTGCTCCG TGGACGAGGG CTCCAAGCCA GGCACCTACG      900
TGATGACCAT CACGGCCAAC GATGCTGACG ACAGCACCAC GGCCAACGGG ATGGTGCGGT      960
ACCGGATCGT GACCCAGACC CCACAGAGCC CGTCCCAGAA TATGTTCACC ATCAACAGCG     1020
AGACTGGAGA TATCGTCACA GTGGCGGCTG GCTGGGACCG AGAGAAAGTT CAGCAGTACA     1080
CAGTCATCGT TCAGGCCACA GATATGGAAG GAAATCTCAA CTATGGCCTC TCAAACACAG     1140
CCACAGCCAT CATCACGGTG ACAGATGTGA ATGACAACCC GTCAGAATTT ACCGCCAGCA     1200
CGTTTGCAGG GGAGGTCCCC GAAAACAGCG TGGAGACCGT GGTCGCAAAC CTCACGGTGA     1260
TGGACCGAGA TCAGCCCCAC TCTCCAAACT GGAATGCCGT TTACCGCATC ATCAGTGGGG     1320
ATCCATCCGG GCACTTCAGC GTCCGCACAG ACCCCGTAAC CAACGAGGGC ATGGTCACCG     1380
TGGTGAAGGC AGTCGACTAC GAGCTCAACA GAGCTTTCAT GCTGACAGTG ATGGTGTCCA     1440
ACCAGGCGCC CCTGGCCAGC GGAATCCAGA TGTCCTTCCA GTCCACGGCA GGGGTGACCA     1500
TCTCCATCAT GGACATCAAC GAGGCTCCCT ACTTCCCCTC AAACCACAAG CTGATCCGCC     1560
TGGAGGAGGG CGTGCCCCCC GGCACCGTGC TGACCACGTT TTCAGCTGTG ACCCTGACC      1620
GGTTCATGCA GCAGGCTGTG AGATACTCAA AGCTGTCAGA CCCAGCGAGC TGGCTGCACA     1680
TCAATGCCAC CAACGGCCAG ATCACCACGG TGGCAGTGCT GGACCGTGAG TCCCTCTACA     1740
CCAAAAACAA CGTCTACGAG GCCACCTTCC TGGCAGCTGA CAATGGGATA CCCCCGGCCA     1800
GCGGCACCGG GACCCTCCAG ATCTATCTCA TTGACATCAA CGACAACGCC CCTGAGCTGC     1860
TGCCCAAGGA GGCGCAGATC TGCGAGAGGC CCAACCTGAA CGCCATCAAC ATCACGGCGG     1920
CCGACGCTGA CGTGCACCCC AACATCGGCC CCTACGTCTT CGAGCTGCCC TTTGTCCCGG     1980
CGGCCGTGCG GAAGAACTGG ACCATCACCC GCCTGAACGG TGACTATGCC CAACTCAGCT     2040
TGCGCATCCT GTACCTGGAG GCCGGGATGT ATGACGTCCC CATCATCGTC ACAGACTCTG     2100
GAAACCCTCC CCTGTCCAAC ACGTCCATCA TCAAAGTCAA GGTGTGCCCA TGTGATGACA     2160
ACGGGGACTG CACCACCATT GGCGCAGTGG CAGCGGCTGG TCTGGGCACC GGTGCCATCG     2220
TGGCCATCCT CATCTGCATC CTCATCCTGC TGACCATGGT CCTGCTGTTT GTCATGTGGA     2280
TGAAGCGGCG AGAGAAGGAG CGCCACACGA AGCAGCTGCT CATTGACCCC GAGGACGACG     2340
TCCGCGAAAA GATCCTCAAG TATGACGAGG AAGGCGGTGG CGAGGAGGAC CAGGACTACG     2400
ACCTCAGCCA GCTGCAGCAG CCGGAAGCCA TGGGCACGT GCCAAGCAAA GCCCCTGGCG      2460
TGCGTCGCGT GGATGAGCGG CCGGTGGGCC CTGAGCCCCA GTACCCGATC AGGCCCATGG     2520
TGCCGCACCC AGGCGACATC GGTGACTTCA TCAATGAGGG ACTCCGCGCT GCTGACAACG     2580
ACCCCACGGC ACCCCCCTAT GACTCCCTGC TGGTCTTCGA CTACGAGGGG AGCGGCTCCA     2640
CCGCAGGCTC CGTCAGCTCC CTGAACTCAT CCAGTTCCGG GGACCAAGAC TACGATTACC     2700
TCAACGACTG GGGCCCCAGA TTCAAGAAGC TGGCGGACAT GTATGGAGGT GGTGAAGAGG     2760
```

```
ATTGACTGAC CTCGCATCTT CGGACCGAAG TGAGAGCCGT GCTCGGACGC CGGAGGAGCA   2820

GGACTGAGCA GAGGCGGCCG GTCTTCCCGA CTCCCTGCGG CTGTGTCCTT AGTGCTGTTA   2880

GGAGGCCCCC CAATCCCCAC GTTGAGCTGT CTAGCATGAG CACCCACCCC CACAGCGCCC   2940

TGCACCCGGC CGCTGCCCAG CACCGCGCTG GCTGGCACTG AAGGACAGCA AGAGGCACTC   3000

TGTCTTCACT TGAATTTCCT AGAACAGAAG CACTGTTTTT AAAAAAAG              3048
```

( 2 ) INFORMATION FOR SEQ ID NO:48:

( i ) SEQUENCE CHARACTERISTICS:
        ( A ) LENGTH: 916 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

```
Met Thr Ala Gly Ala Gly Val Leu Leu Leu Leu Ser Leu Ser Gly
 1           5                  10                 15

Ala Leu Arg Ala His Asn Glu Asp Leu Thr Thr Arg Glu Thr Cys Lys
            20                  25                 30

Ala Gly Phe Ser Glu Asp Asp Tyr Thr Ala Leu Ile Ser Gln Asn Ile
            35                  40                 45

Leu Glu Gly Glu Lys Leu Leu Gln Val Lys Phe Ser Ser Cys Val Gly
 50                  55                  60

Thr Lys Gly Thr Gln Tyr Glu Thr Asn Ser Met Asp Phe Leu Val Gly
 65                  70                  75                 80

Ala Asp Gly Thr Val Phe Ala Thr Arg Glu Leu Gln Val Pro Ser Glu
                    85                  90                 95

Gln Val Ala Phe Thr Val Thr Ala Trp Asp Ser Gln Thr Ala Glu Lys
                   100                 105                110

Trp Asp Ala Val Val Arg Leu Leu Val Ala Gln Thr Ser Ser Pro His
            115                 120                125

Ser Gly His Lys Pro Gln Lys Gly Lys Lys Val Val Ala Leu Asp Pro
    130                 135                 140

Ser Pro Pro Lys Asp Thr Leu Leu Pro Trp Pro Gln His Gln Asn
145                 150                 155                160

Ala Asn Gly Leu Arg Arg Arg Lys Arg Asp Trp Val Ile Pro Pro Ile
                    165                 170                175

Asn Val Pro Glu Asn Ser Arg Gly Pro Phe Pro Gln Gln Leu Val Arg
            180                 185                 190

Ile Arg Ser Asp Lys Asp Asn Asp Ile Pro Ile Arg Tyr Ser Ile Thr
    195                 200                 205

Gly Val Gly Ala Asp Gln Pro Pro Met Glu Val Phe Ser Ile Asn Ser
    210                 215                 220

Met Ser Gly Arg Met Tyr Val Thr Arg Pro Met Asp Arg Glu Glu His
225                 230                 235                240

Ala Ser Tyr His Leu Arg Ala His Ala Val Asp Met Asn Gly Asn Lys
                    245                 250                255

Val Glu Asn Pro Ile Asp Leu Tyr Ile Tyr Val Ile Asp Met Asn Asp
            260                 265                 270

Asn His Pro Glu Phe Ile Asn Gln Val Tyr Asn Cys Ser Val Asp Glu
    275                 280                 285

Gly Ser Lys Pro Gly Thr Tyr Val Met Thr Ile Thr Ala Asn Asp Ala
    290                 295                 300
```

```
Asp  Asp  Ser  Thr  Thr  Ala  Asn  Gly  Met  Val  Arg  Tyr  Arg  Ile  Val  Thr
305                      310                 315                      320

Gln  Thr  Pro  Gln  Ser  Pro  Ser  Gln  Asn  Met  Phe  Thr  Ile  Asn  Ser  Glu
                    325                 330                      335

Thr  Gly  Asp  Ile  Val  Thr  Val  Ala  Ala  Gly  Trp  Asp  Arg  Glu  Lys  Val
               340                 345                      350

Gln  Gln  Tyr  Thr  Val  Ile  Val  Gln  Ala  Thr  Asp  Met  Glu  Gly  Asn  Leu
          355                 360                      365

Asn  Tyr  Gly  Leu  Ser  Asn  Thr  Ala  Thr  Ala  Ile  Ile  Thr  Val  Thr  Asp
     370                 375                      380

Val  Asn  Asp  Asn  Pro  Ser  Glu  Phe  Thr  Ala  Ser  Thr  Phe  Ala  Gly  Glu
385                      390                 395                           400

Val  Pro  Glu  Asn  Ser  Val  Glu  Thr  Val  Val  Ala  Asn  Leu  Thr  Val  Met
               405                 410                      415

Asp  Arg  Asp  Gln  Pro  His  Ser  Pro  Asn  Trp  Asn  Ala  Val  Tyr  Arg  Ile
               420                 425                      430

Ile  Ser  Gly  Asp  Pro  Ser  Gly  His  Phe  Ser  Val  Arg  Thr  Asp  Pro  Val
          435                 440                      445

Thr  Asn  Glu  Gly  Met  Val  Thr  Val  Val  Lys  Ala  Val  Asp  Tyr  Glu  Leu
     450                 455                      460

Asn  Arg  Ala  Phe  Met  Leu  Thr  Val  Met  Val  Ser  Asn  Gln  Ala  Pro  Leu
465                      470                 475                           480

Ala  Ser  Gly  Ile  Gln  Met  Ser  Phe  Gln  Ser  Thr  Ala  Gly  Val  Thr  Ile
               485                 490                      495

Ser  Ile  Met  Asp  Ile  Asn  Glu  Ala  Pro  Tyr  Phe  Pro  Ser  Asn  His  Lys
               500                 505                      510

Leu  Ile  Arg  Leu  Glu  Glu  Gly  Val  Pro  Gly  Thr  Val  Leu  Thr  Thr
          515                 520                      525

Phe  Ser  Ala  Val  Asp  Pro  Asp  Arg  Phe  Met  Gln  Gln  Ala  Val  Arg  Tyr
     530                 535                      540

Ser  Lys  Leu  Ser  Asp  Pro  Ala  Ser  Trp  Leu  His  Ile  Asn  Ala  Thr  Asn
545                      550                 555                           560

Gly  Gln  Ile  Thr  Thr  Val  Ala  Val  Leu  Asp  Arg  Glu  Ser  Leu  Tyr  Thr
               565                 570                      575

Lys  Asn  Asn  Val  Tyr  Glu  Ala  Thr  Phe  Leu  Ala  Ala  Asp  Asn  Gly  Ile
               580                 585                      590

Pro  Pro  Ala  Ser  Gly  Thr  Gly  Thr  Leu  Gln  Ile  Tyr  Leu  Ile  Asp  Ile
          595                 600                      605

Asn  Asp  Asn  Ala  Pro  Glu  Leu  Leu  Pro  Lys  Glu  Ala  Gln  Ile  Cys  Glu
     610                 615                      620

Arg  Pro  Asn  Leu  Asn  Ala  Ile  Asn  Ile  Thr  Ala  Ala  Asp  Ala  Asp  Val
625                      630                 635                           640

His  Pro  Asn  Ile  Gly  Pro  Tyr  Val  Phe  Glu  Leu  Pro  Phe  Val  Pro  Ala
               645                 650                      655

Ala  Val  Arg  Lys  Asn  Trp  Thr  Ile  Thr  Arg  Leu  Asn  Gly  Asp  Tyr  Ala
               660                 665                      670

Gln  Leu  Ser  Leu  Arg  Ile  Leu  Tyr  Leu  Glu  Ala  Gly  Met  Tyr  Asp  Val
          675                 680                      685

Pro  Ile  Ile  Val  Thr  Asp  Ser  Gly  Asn  Pro  Pro  Leu  Ser  Asn  Thr  Ser
     690                 695                      700

Ile  Ile  Lys  Val  Lys  Val  Cys  Pro  Cys  Asp  Asp  Asn  Gly  Asp  Cys  Thr
705                      710                 715                           720

Thr  Ile  Gly  Ala  Val  Ala  Ala  Ala  Gly  Leu  Gly  Thr  Gly  Ala  Ile  Val
               725                 730                      735
```

| | | | | | | | | | | | | | |
|---|---|---|---|---|---|---|---|---|---|---|---|---|---|
| Ala | Ile | Leu | Ile 740 | Cys | Ile | Leu | Ile | Leu 745 | Leu | Thr | Met | Val | Leu 750 | Leu | Phe |
| Val | Met | Trp 755 | Met | Lys | Arg | Arg | Glu 760 | Lys | Glu | Arg | His | Thr 765 | Lys | Gln | Leu |
| Leu | Ile 770 | Asp | Pro | Glu | Asp | Asp 775 | Val | Arg | Glu | Lys | Ile 780 | Leu | Lys | Tyr | Asp |
| Glu 785 | Glu | Gly | Gly | Gly | Glu 790 | Glu | Asp | Gln | Asp | Tyr 795 | Asp | Leu | Ser | Gln | Leu 800 |
| Gln | Gln | Pro | Glu | Ala 805 | Met | Gly | His | Val | Pro 810 | Ser | Lys | Ala | Pro | Gly 815 | Val |
| Arg | Arg | Val | Asp 820 | Glu | Arg | Pro | Val | Gly 825 | Pro | Glu | Pro | Gln | Tyr 830 | Pro | Ile |
| Arg | Pro | Met 835 | Val | Pro | His | Pro | Gly 840 | Asp | Ile | Gly | Asp | Phe 845 | Ile | Asn | Glu |
| Gly | Leu 850 | Arg | Ala | Ala | Asp | Asn 855 | Asp | Pro | Thr | Ala | Pro 860 | Pro | Tyr | Asp | Ser |
| Leu 865 | Leu | Val | Phe | Asp | Tyr 870 | Glu | Gly | Ser | Gly | Ser 875 | Thr | Ala | Gly | Ser | Val 880 |
| Ser | Ser | Leu | Asn | Ser 885 | Ser | Ser | Ser | Gly | Asp 890 | Gln | Asp | Tyr | Asp 895 | Tyr | Leu |
| Asn | Asp | Trp | Gly 900 | Pro | Arg | Phe | Lys | Lys 905 | Leu | Ala | Asp | Met | Tyr 910 | Gly | Gly |
| Gly | Glu | Glu 915 | Asp |

(2) INFORMATION FOR SEQ ID NO:49:

(i) SEQUENCE CHARACTERISTICS:
    (A) LENGTH: 3164 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO:49:

```
CTCCACTCAC GCTCAGCCCT GGACGGACAG GCAGTCCAAC GGAACAGAAA CATCCCTCAG      60
CCCACAGGCA CGATCTGTTC CTCCTGGGAA GATGCAGAGG CTATGATGCT CCTCGCCACA     120
TCGGGCGCCT GCCTGGGCCT GCTGGCAGTG GCAGCAGTGG CAGCAGCAGG TGCTAACCCT     180
GCCCAACGGG ACACCCACAG CCTGCTGCCC ACCCACCGGC GCCAAAAGAG AGATTGGATT     240
TGGAACCAGA TGCACATTGA TGAAGAGAAA AACACCTCAC TTCCCCATCA TGTAGGCAAG     300
ATCAAGTCAA GCGTGAGTCG CAAGAATGCC AAGTACCTGC TCAAAGGAGA ATATGTGGGC     360
AAGGTCTTCC GGGTCGATGC AGAGACAGGA GACGTGTTCG CCATTGAGAG GCTGGACCGG     420
GAGAATATCT CAGAGTACCA CCTCACTGCT GTCATTGTGG ACAAGGACAC TGGCGAAAAC     480
CTGGAGACTC CTTCCAGCTT CACCATCAAA GTTCATGACG TGAACGACAA CTGGCCTGTG     540
TTCACGCATC GGTTGTTCAA TGCGTCCGTG CCTGAGTCGT CGGCTGTGGG GACCTCAGTC     600
ATCTCTGTGA CAGCAGTGGA TGCAGACGAC CCCACTGTGG GAGACCACGC CTCTGTCATG     660
TACCAAATCC TGAAGGGGAA AGAGTATTTT GCCATCGATA ATTCTGGACG TATTATCACA     720
ATAACGAAAA GCTTGGACCG AGAGAAGCAG GCCAGGTATG AGATCGTGGT GGAAGCGCGA     780
GATGCCCAGG GCCTCCGGGG GGACTCGGGC ACGGCCACCG TGCTGGTCAC TCTGCAAGAC     840
ATCAATGACA ACTTCCCCTT CTTCACCCAG ACCAAGTACA CATTTGTCGT GCCTGAAGAC     900
```

-continued

| | | | | | | |
|---|---|---|---|---|---|---|
| ACCCGTGTGG | GCACCTCTGT | GGGCTCTCTG | TTTGTTGAGG | ACCCAGATGA | GCCCCAGAAC | 960 |
| CGGATGACCA | AGTACAGCAT | CTTGCGGGGC | GACTACCAGG | ACGCTTTCAC | CATTGAGACA | 1020 |
| AACCCCGCCC | ACAACGAGGG | CATCATCAAG | CCCATGAAGC | CTCTGGATTA | TGAATACATC | 1080 |
| CAGCAATACA | GCTTCATAGT | CGAGGCCACA | GACCCCACCA | TCGACCTCCG | ATACATGAGC | 1140 |
| CCTCCCGCGG | GAAACAGAGC | CCAGGTCATT | ATCAACATCA | CAGATGTGGA | CGAGCCCCCC | 1200 |
| ATTTTCCAGC | AGCCTTTCTA | CCACTTCCAG | CTGAAGGAAA | ACCAGAAGAA | GCCTCTGATT | 1260 |
| GGCACAGTGC | TGGCCATGGA | CCCTGATGCG | GCTAGGCATA | GCATTGGATA | CTCCATCCGC | 1320 |
| AGGACCAGTG | ACAAGGGCCA | GTTCTTCCGA | GTCACAAAAA | AGGGGACAT | TTACAATGAG | 1380 |
| AAAGAACTGG | ACAGAGAAGT | CTACCCCTGG | TATAACCTGA | CTGTGGAGGC | CAAAGAACTG | 1440 |
| GATTCCACTG | GAACCCCCAC | AGGAAAAGAA | TCCATTGTGC | AAGTCCACAT | TGAAGTTTTG | 1500 |
| GATGAGAATG | ACAATGCCCC | GGAGTTTGCC | AAGCCCTACC | AGCCCAAAGT | GTGTGAGAAC | 1560 |
| GCTGTCCATG | GCCAGCTGGT | CCTGCAGATC | TCCGCAATAG | ACAAGGACAT | AACACCACGA | 1620 |
| AACGTGAAGT | TCAAATTCAT | CTTGAATACT | GAGAACAACT | TTACCCTCAC | GGATAATCAC | 1680 |
| GATAACACGG | CCAACATCAC | AGTCAAGTAT | GGGCAGTTTG | ACCGGGAGCA | TACCAAGGTC | 1740 |
| CACTTCCTAC | CCGTGGTCAT | CTCAGACAAT | GGGATGCCAA | GTCGCACGGG | CACCAGCACG | 1800 |
| CTGACCGTGG | CCGTGTGCAA | GTGCAACGAG | CAGGGCGAGT | TCACCTTCTG | CGAGGATATG | 1860 |
| GCCGCCCAGG | TGGGCGTGAG | CATCCAGGCA | GTGGTAGCCA | TCTTACTCTG | CATCCTCACC | 1920 |
| ATCACAGTGA | TCACCCTGCT | CATCTTCCTG | CGGCGGCGGC | TCCGGAAGCA | GGCCCGCGCG | 1980 |
| CACGGCAAGA | GCGTGCCGGA | GATCCACGAG | CAGCTGGTCA | CCTACGACGA | GGAGGGCGGC | 2040 |
| GGCGAGATGG | ACACCACCAG | CTACGATGTG | TCGGTGCTCA | ACTCGGTGCG | CCGCGGCGGG | 2100 |
| GCCAAGCCCC | GCGGCCCCGC | GCTGGACGCC | CGGCCTTCCC | TCTATGCGCA | GGTGCAGAAG | 2160 |
| CCACCGAGGC | ACGCGCCTGG | GGCACACGGA | GGGCCCGGGG | AGATGGCAGC | CATGATCGAG | 2220 |
| GTGAAGAAGG | ACGAGGCGGA | CCACGACGGC | GACGGCCCCC | CCTACGACAC | GCTGCACATC | 2280 |
| TACGGCTACG | AGGGCTCCGA | GTCCATAGCC | GAGTCCCTCA | GCTCCCTGGG | CACCGACTCA | 2340 |
| TCCGACTCTG | ACGTGGATTA | CGACTTCCTT | AACGACTGGG | GACCCAGGTT | TAAGATGCTG | 2400 |
| GCTGAGCTGT | ACGGCTCGGA | CCCCCGGGAG | GAGCTGCTGT | ATTAGGCGGC | CGAGGTCACT | 2460 |
| CTGGGCCTGG | GGACCCAAAC | CCCCTGCAGC | CCAGGCCAGT | CAGACTCCAG | GCACCACAGC | 2520 |
| CTCCAAAAAT | GGCAGTGACT | CCCCAGCCCA | GCACCCCTTC | CTCGTGGGTC | CAGAGACCT | 2580 |
| CATCAGCCTT | GGGATAGCAA | ACTCCAGGTT | CCTGAAATAT | CCAGGAATAT | ATGTCAGTGA | 2640 |
| TGACTATTCT | CAAATGCTGG | CAAATCCAGG | CTGGTGTTCT | GTCTGGGCTC | AGACATCCAC | 2700 |
| ATAACCCTGT | CACCCACAGA | CCGCCGTCTA | ACTCAAAGAC | TTCCTCTGGC | TCCCCAAGGC | 2760 |
| TGCAAAGCAA | AACAGACTGT | GTTTAACTGC | TGCAGGGTCT | TTTTCTAGGG | TCCCTGAACG | 2820 |
| CCCTGGTAAG | GCTGGTGAGG | TCCTGGTGCC | TATCTGCCTG | GAGGCAAAGG | CCTGGACAGC | 2880 |
| TTGACTTGTG | GGGCAGGATT | CTCTGCAGCC | CATTCCCAAG | GGAGACTGAC | CATCATGCCC | 2940 |
| TCTCTCGGGA | GCCCTAGCCC | TGCTCCAACT | CCATACTCCA | CTCCAAGTGC | CCCACCACTC | 3000 |
| CCCAACCCCT | CTCCAGGCCT | GTCAAGAGGG | AGGAAGGGGC | CCCATGGCAG | CTCCTGACCT | 3060 |
| TGGGTCCTGA | AGTGACCTCA | CTGGCCTGCC | ATGCCAGTAA | CTGTGCTGTA | CTGAGCACTG | 3120 |
| AACCACATTC | AGGGAAATGG | CTTATTAAAC | TTTGAAGCAA | CTGT | | 3164 |

( 2 ) INFORMATION FOR SEQ ID NO:50:

( i ) SEQUENCE CHARACTERISTICS:

( A ) LENGTH: 780 amino acids
( B ) TYPE: amino acid
( D ) TOPOLOGY: linear ( i i ) MOLECULE TYPE: protein ( x i ) SEQUENCE DESCRIPTION: SEQ ID NO:50:

| Met | Met | Leu | Leu | Ala | Thr | Ser | Gly | Ala | Cys | Leu | Gly | Leu | Leu | Ala | Val |
|---|---|---|---|---|---|---|---|---|---|---|---|---|---|---|---|
| 1 | | | | 5 | | | | | 10 | | | | | 15 | |

| Ala | Ala | Val | Ala | Ala | Ala | Gly | Ala | Asn | Pro | Ala | Gln | Arg | Asp | Thr | His |
|---|---|---|---|---|---|---|---|---|---|---|---|---|---|---|---|
| | | | 20 | | | | | 25 | | | | | 30 | | |

| Ser | Leu | Leu | Pro | Thr | His | Arg | Arg | Gln | Lys | Arg | Asp | Trp | Ile | Trp | Asn |
|---|---|---|---|---|---|---|---|---|---|---|---|---|---|---|---|
| | | 35 | | | | | 40 | | | | | 45 | | | |

| Gln | Met | His | Ile | Asp | Glu | Glu | Lys | Asn | Thr | Ser | Leu | Pro | His | His | Val |
|---|---|---|---|---|---|---|---|---|---|---|---|---|---|---|---|
| | 50 | | | | | 55 | | | | | 60 | | | | |

| Gly | Lys | Ile | Lys | Ser | Ser | Val | Ser | Arg | Lys | Asn | Ala | Lys | Tyr | Leu | Leu |
|---|---|---|---|---|---|---|---|---|---|---|---|---|---|---|---|
| 65 | | | | | 70 | | | | | 75 | | | | | 80 |

| Lys | Gly | Glu | Tyr | Val | Gly | Lys | Val | Phe | Arg | Val | Asp | Ala | Glu | Thr | Gly |
|---|---|---|---|---|---|---|---|---|---|---|---|---|---|---|---|
| | | | | 85 | | | | | 90 | | | | | 95 | |

| Asp | Val | Phe | Ala | Ile | Glu | Arg | Leu | Asp | Arg | Glu | Asn | Ile | Ser | Glu | Tyr |
|---|---|---|---|---|---|---|---|---|---|---|---|---|---|---|---|
| | | | 100 | | | | | 105 | | | | | 110 | | |

| His | Leu | Thr | Ala | Val | Ile | Val | Asp | Lys | Asp | Thr | Gly | Glu | Asn | Leu | Glu |
|---|---|---|---|---|---|---|---|---|---|---|---|---|---|---|---|
| | | 115 | | | | | 120 | | | | | 125 | | | |

| Thr | Pro | Ser | Ser | Phe | Thr | Ile | Lys | Val | His | Asp | Val | Asn | Asp | Asn | Trp |
|---|---|---|---|---|---|---|---|---|---|---|---|---|---|---|---|
| | 130 | | | | 135 | | | | | 140 | | | | | |

| Pro | Val | Phe | Thr | His | Arg | Leu | Phe | Asn | Ala | Ser | Val | Pro | Glu | Ser | Ser |
|---|---|---|---|---|---|---|---|---|---|---|---|---|---|---|---|
| 145 | | | | | 150 | | | | | 155 | | | | | 160 |

| Ala | Val | Gly | Thr | Ser | Val | Ile | Ser | Val | Thr | Ala | Val | Asp | Ala | Asp | Asp |
|---|---|---|---|---|---|---|---|---|---|---|---|---|---|---|---|
| | | | | 165 | | | | | 170 | | | | | 175 | |

| Pro | Thr | Val | Gly | Asp | His | Ala | Ser | Val | Met | Tyr | Gln | Ile | Leu | Lys | Gly |
|---|---|---|---|---|---|---|---|---|---|---|---|---|---|---|---|
| | | | 180 | | | | | 185 | | | | | 190 | | |

| Lys | Glu | Tyr | Phe | Ala | Ile | Asp | Asn | Ser | Gly | Arg | Ile | Ile | Thr | Ile | Thr |
|---|---|---|---|---|---|---|---|---|---|---|---|---|---|---|---|
| | | | 195 | | | | | 200 | | | | | 205 | | |

| Lys | Ser | Leu | Asp | Arg | Glu | Lys | Gln | Ala | Arg | Tyr | Glu | Ile | Val | Val | Glu |
|---|---|---|---|---|---|---|---|---|---|---|---|---|---|---|---|
| | 210 | | | | | 215 | | | | | 220 | | | | |

| Ala | Arg | Asp | Ala | Gln | Gly | Leu | Arg | Gly | Asp | Ser | Gly | Thr | Ala | Thr | Val |
|---|---|---|---|---|---|---|---|---|---|---|---|---|---|---|---|
| 225 | | | | | 230 | | | | | 235 | | | | | 240 |

| Leu | Val | Thr | Leu | Gln | Asp | Ile | Asn | Asp | Asn | Phe | Pro | Phe | Phe | Thr | Gln |
|---|---|---|---|---|---|---|---|---|---|---|---|---|---|---|---|
| | | | | 245 | | | | | 250 | | | | | 255 | |

| Thr | Lys | Tyr | Thr | Phe | Val | Val | Pro | Glu | Asp | Thr | Arg | Val | Gly | Thr | Ser |
|---|---|---|---|---|---|---|---|---|---|---|---|---|---|---|---|
| | | | 260 | | | | | 265 | | | | | 270 | | |

| Val | Gly | Ser | Leu | Phe | Val | Glu | Asp | Pro | Asp | Glu | Pro | Gln | Asn | Arg | Met |
|---|---|---|---|---|---|---|---|---|---|---|---|---|---|---|---|
| | | 275 | | | | | 280 | | | | | 285 | | | |

| Thr | Lys | Tyr | Ser | Ile | Leu | Arg | Gly | Asp | Tyr | Gln | Asp | Ala | Phe | Thr | Ile |
|---|---|---|---|---|---|---|---|---|---|---|---|---|---|---|---|
| | 290 | | | | | 295 | | | | | 300 | | | | |

| Glu | Thr | Asn | Pro | Ala | His | Asn | Glu | Gly | Ile | Ile | Lys | Pro | Met | Lys | Pro |
|---|---|---|---|---|---|---|---|---|---|---|---|---|---|---|---|
| 305 | | | | | 310 | | | | | 315 | | | | | 320 |

| Leu | Asp | Tyr | Glu | Tyr | Ile | Gln | Gln | Tyr | Ser | Phe | Ile | Val | Glu | Ala | Thr |
|---|---|---|---|---|---|---|---|---|---|---|---|---|---|---|---|
| | | | | 325 | | | | | 330 | | | | | 335 | |

| Asp | Pro | Thr | Ile | Asp | Leu | Arg | Tyr | Met | Ser | Pro | Pro | Ala | Gly | Asn | Arg |
|---|---|---|---|---|---|---|---|---|---|---|---|---|---|---|---|
| | | | 340 | | | | | 345 | | | | | 350 | | |

| Ala | Gln | Val | Ile | Ile | Asn | Ile | Thr | Asp | Val | Asp | Glu | Pro | Pro | Ile | Phe |
|---|---|---|---|---|---|---|---|---|---|---|---|---|---|---|---|
| | | 355 | | | | | 360 | | | | | 365 | | | |

| Gln | Gln | Pro | Phe | Tyr | His | Phe | Gln | Leu | Lys | Glu | Asn | Gln | Lys | Lys | Pro |
|---|---|---|---|---|---|---|---|---|---|---|---|---|---|---|---|
| | 370 | | | | | 375 | | | | | 380 | | | | |

```
Leu  Ile  Gly  Thr  Val  Leu  Ala  Met  Asp  Pro  Asp  Ala  Ala  Arg  His  Ser
385                      390                 395                           400

Ile  Gly  Tyr  Ser  Ile  Arg  Arg  Thr  Ser  Asp  Lys  Gly  Gln  Phe  Phe  Arg
               405                      410                           415

Val  Thr  Lys  Lys  Gly  Asp  Ile  Tyr  Asn  Glu  Lys  Glu  Leu  Asp  Arg  Glu
               420                 425                      430

Val  Tyr  Pro  Trp  Tyr  Asn  Leu  Thr  Val  Glu  Ala  Lys  Glu  Leu  Asp  Ser
          435                 440                      445

Thr  Gly  Thr  Pro  Thr  Gly  Lys  Glu  Ser  Ile  Val  Gln  Val  His  Ile  Glu
     450                      455                      460

Val  Leu  Asp  Glu  Asn  Asp  Asn  Ala  Pro  Glu  Phe  Ala  Lys  Pro  Tyr  Gln
465                      470                 475                           480

Pro  Lys  Val  Cys  Glu  Asn  Ala  Val  His  Gly  Gln  Leu  Val  Leu  Gln  Ile
               485                 490                           495

Ser  Ala  Ile  Asp  Lys  Asp  Ile  Thr  Pro  Arg  Asn  Val  Lys  Phe  Lys  Phe
               500                 505                      510

Ile  Leu  Asn  Thr  Glu  Asn  Asn  Phe  Thr  Leu  Thr  Asp  Asn  His  Asp  Asn
          515                 520                      525

Thr  Ala  Asn  Ile  Thr  Val  Lys  Tyr  Gly  Gln  Phe  Asp  Arg  Glu  His  Thr
     530                 535                      540

Lys  Val  His  Phe  Leu  Pro  Val  Val  Ile  Ser  Asp  Asn  Gly  Met  Pro  Ser
545                      550                 555                           560

Arg  Thr  Gly  Thr  Ser  Thr  Leu  Thr  Val  Ala  Val  Cys  Lys  Cys  Asn  Glu
                    565                 570                           575

Gln  Gly  Glu  Phe  Thr  Phe  Cys  Glu  Asp  Met  Ala  Ala  Gln  Val  Gly  Val
               580                 585                           590

Ser  Ile  Gln  Ala  Val  Val  Ala  Ile  Leu  Leu  Cys  Ile  Leu  Thr  Ile  Thr
          595                 600                      605

Val  Ile  Thr  Leu  Leu  Ile  Phe  Leu  Arg  Arg  Arg  Leu  Arg  Leu  Gln  Ala
     610                 615                      620

Arg  Ala  His  Gly  Lys  Ser  Val  Pro  Glu  Ile  His  Glu  Gln  Leu  Val  Thr
625                      630                 635                           640

Tyr  Asp  Glu  Glu  Gly  Gly  Gly  Glu  Met  Asp  Thr  Thr  Ser  Tyr  Asp  Val
               645                 650                           655

Ser  Val  Leu  Asn  Ser  Val  Arg  Arg  Gly  Gly  Ala  Lys  Pro  Pro  Arg  Pro
          660                 665                      670

Ala  Leu  Asp  Ala  Arg  Pro  Ser  Leu  Tyr  Ala  Gln  Val  Gln  Lys  Pro  Pro
     675                 680                      685

Arg  His  Ala  Pro  Gly  Ala  His  Gly  Gly  Pro  Gly  Glu  Met  Ala  Ala  Met
     690                 695                      700

Ile  Glu  Val  Lys  Lys  Asp  Glu  Ala  Asp  His  Asp  Gly  Asp  Gly  Pro  Pro
705                      710                 715                           720

Tyr  Asp  Thr  Leu  His  Ile  Tyr  Gly  Tyr  Glu  Gly  Ser  Glu  Ser  Ile  Ala
               725                      730                      735

Glu  Ser  Leu  Ser  Ser  Leu  Gly  Thr  Asp  Ser  Ser  Asp  Ser  Asp  Val  Asp
               740                 745                      750

Tyr  Asp  Phe  Leu  Asn  Asp  Trp  Gly  Pro  Arg  Phe  Lys  Met  Leu  Ala  Glu
          755                 760                      765

Leu  Tyr  Gly  Ser  Asp  Pro  Arg  Glu  Glu  Leu  Leu  Tyr
770                      775                 780
```

( 2 ) INFORMATION FOR SEQ ID NO:51:

( i ) SEQUENCE CHARACTERISTICS:
        ( A ) LENGTH: 1369 base pairs

-continued (B) TYPE: nucleic acid
(C) STRANDEDNESS: single
(D) TOPOLOGY: linear (i i) MOLECULE TYPE: cDNA (x i) SEQUENCE DESCRIPTION: SEQ ID NO:51:

| | | | | | |
|---|---|---|---|---|---|
| TGTAGATGAG | CCACCTGTCT | TCAGCAAACT | GGCCTACATC | TTACAAATAA | GAGAAGATGC | 60 |
| TCAGATAAAC | ACCACAATAG | GCTCCGTCAC | AGCCCAAGAT | CCAGATGCTG | CCAGGAATCC | 120 |
| TGTCAAGTAC | TCTATAGATC | GACACACAGA | TATGGACAGA | ATATTCAACA | TTGATTCTGG | 180 |
| AAATGGTTCG | ATTTTTACAT | CGAAACTTCT | TGACCGAGAA | ACACTGCTAT | GGCACAACAT | 240 |
| TACAGTGATA | GCAACAGAGA | TCAATAATCC | AAAGCAAAGT | AGTCGAGTAC | CTCTATATAT | 300 |
| TAAAGTTCTA | GATGTCAATG | ACAACGCCCC | AGAATTTGCT | GAGTTCTATG | AAACTTTTGT | 360 |
| CTGTGAAAAA | GCAAAGGCAG | ATCAGTTGAT | TCAGACCTTG | CATGCTGTTA | GCAAGGATGA | 420 |
| CCCTTATAGT | GGGCACCAAT | TTTCGTTTTC | CTTGGCCCCT | GAAGCAGCCA | GTGGCTCAAA | 480 |
| CTTTACCATT | CAAGACAACA | AAGACAACAC | GGCGGGAATC | TTAACTCGGA | AAAATGGCTA | 540 |
| TAATAGACAC | GAGATGAGCA | CCTATCTCTT | GCCTGTGGTC | ATTTCAGACA | ACGACTACCC | 600 |
| AGTTCAAAGC | AGCACTGGGA | CAGTGACTGT | CCGGGTCTGT | GCATGTGACC | ACCACGGGAA | 660 |
| CATGCAATCC | TGCCATGCGG | AGGCGCTCAT | CCACCCCACG | GGACTGAGCA | CGGGGGCTCT | 720 |
| GGTTGCCATC | CTTCTGTGCA | TCGTGATCCT | ACTAGTGACA | GTGGTGCTGT | TTGCAGCTCT | 780 |
| GAGGCGGCAG | CGAAAAAAAG | AGCCTTTGAT | CATTTCCAAA | GAGGACATCA | GAGATAACAT | 840 |
| TGTCAGTTAC | AACGACGAAG | GTGGTGGAGA | GGAGGACACC | CAGGCTTTTG | ATATCGGCAC | 900 |
| CCTGAGGAAT | CCTGAAGCCA | TAGAGGACAA | CAAATTACGA | AGGGACATTG | TGCCCGAAGC | 960 |
| CCTTTTCCTA | CCCCGACGGA | CTCCAACAGC | TCGCGACAAC | ACCGATGTCA | GAGATTTCAT | 1020 |
| TAACCAAAGG | TTAAAGGAAA | ATGACACGGA | CCCCACTGCC | CCGCCATACG | ACTCCCTGGC | 1080 |
| CACTTACGCC | TATGAAGGCA | CTGGCTCCGT | GGCGGATTCC | CTGAGCTCGC | TGGAGTCAGT | 1140 |
| GACCACGGAT | GCAGATCAAG | ACTATGATTA | CCTTTAGTGA | CTGGGACCTC | GATTCAAAAA | 1200 |
| GCTTGCAGAT | ATGTATGGAG | GAGTGGACAG | TGACAAAGAC | TCCTAATCTG | TTGCCTTTTT | 1260 |
| CATTTTCCAA | TACGACACTG | AAATATGTGA | AGTGGCTATT | TCTTTATATT | TATCCACTAC | 1320 |
| TCCGTGAAGG | CTTCTCTGTT | CTACCCGTTC | CAAAAGCCAA | TGGCTGCAG | | 1369 |

(2) INFORMATION FOR SEQ ID NO:52:

(i) SEQUENCE CHARACTERISTICS:
(A) LENGTH: 414 amino acids
(B) TYPE: amino acid
(D) TOPOLOGY: linear (i i) MOLECULE TYPE: protein (x i) SEQUENCE DESCRIPTION: SEQ ID NO:52:

| Val | Asp | Glu | Pro | Pro | Val | Phe | Ser | Lys | Leu | Ala | Tyr | Ile | Leu | Gln | Ile |
|---|---|---|---|---|---|---|---|---|---|---|---|---|---|---|---|
| 1 | | | | 5 | | | | | 10 | | | | | 15 | |
| Arg | Glu | Asp | Ala | Gln | Ile | Asn | Thr | Thr | Ile | Gly | Ser | Val | Thr | Ala | Gln |
| | | | | 20 | | | | | 25 | | | | | 30 | |
| Asp | Pro | Asp | Ala | Ala | Arg | Asn | Pro | Val | Lys | Tyr | Ser | Ile | Lys | Arg | His |
| | | | 35 | | | | | 40 | | | | 45 | | | |
| Thr | Asp | Met | Asp | Arg | Ile | Phe | Asn | Ile | Asp | Ser | Gly | Asn | Gly | Ser | Ile |
| | | 50 | | | | | 55 | | | | | 60 | | | |
| Phe | Thr | Ser | Lys | Leu | Leu | Lys | Arg | Glu | Thr | Leu | Leu | Trp | His | Asn | Ile |
| 65 | | | | | 70 | | | | | 75 | | | | | 80 |

| | | | | | | | | | | | | | | |
|---|---|---|---|---|---|---|---|---|---|---|---|---|---|---|
| Thr | Val | Ile | Ala | Thr 85 | Glu | Ile | Asn | Asn | Pro 90 | Lys | Gln | Ser | Ser 95 | Arg | Val |
| Pro | Leu | Tyr | Ile 100 | Lys | Val | Leu | Asp | Val 105 | Asn | Asp | Asn | Ala | Pro 110 | Glu | Phe |
| Ala | Glu | Phe 115 | Tyr | Glu | Thr | Phe | Val 120 | Cys | Glu | Lys | Ala | Lys 125 | Ala | Asp | Gln |
| Leu | Ile | Gln | Thr | Leu | His | Ala 135 | Val | Asp | Lys | Asp | Pro 140 | Tyr | Ser | Gly |
| His 145 | Gln | Phe | Ser | Phe | Ser 150 | Leu | Ala | Pro | Glu | Ala 155 | Ala | Ser | Gly | Ser | Asn 160 |
| Phe | Thr | Ile | Gln | Asp 165 | Asn | Lys | Asp | Asn | Thr 170 | Ala | Gly | Ile | Leu | Thr 175 | Arg |
| Lys | Asn | Gly | Tyr 180 | Asn | Arg | His | Glu | Met 185 | Ser | Thr | Tyr | Leu | Leu 190 | Pro | Val |
| Val | Ile | Ser 195 | Asp | Asn | Asp | Tyr | Pro 200 | Val | Gln | Ser | Ser | Thr 205 | Gly | Thr | Val |
| Thr | Val 210 | Arg | Val | Cys | Ala | Cys 215 | Asp | His | His | Gly | Asn 220 | Met | Gln | Ser | Cys |
| His 225 | Ala | Glu | Ala | Leu | Ile 230 | His | Pro | Thr | Gly | Leu 235 | Ser | Thr | Gly | Ala | Leu 240 |
| Val | Ala | Ile | Leu | Leu 245 | Cys | Ile | Val | Ile | Leu 250 | Leu | Val | Thr | Val | Val 255 | Leu |
| Phe | Ala | Ala | Leu | Arg 260 | Arg | Gln | Arg | Lys 265 | Lys | Glu | Pro | Leu | Ile 270 | Ile | Ser |
| Lys | Glu | Asp 275 | Ile | Arg | Asp | Asn | Ile 280 | Val | Ser | Tyr | Asn | Asp 285 | Glu | Gly | Gly |
| Gly | Glu 290 | Glu | Asp | Thr | Gln | Ala 295 | Phe | Asp | Ile | Gly | Thr 300 | Leu | Arg | Asn | Pro |
| Glu 305 | Ala | Ile | Glu | Asp | Asn 310 | Lys | Leu | Arg | Arg | Asp 315 | Ile | Val | Pro | Glu | Ala 320 |
| Leu | Phe | Leu | Pro | Arg 325 | Arg | Thr | Pro | Thr | Ala 330 | Arg | Asp | Asn | Thr 335 | Asp | Val |
| Arg | Asp | Phe | Ile 340 | Asn | Gln | Arg | Leu | Lys 345 | Glu | Asn | Asp | Thr | Asp 350 | Pro | Thr |
| Ala | Pro | Pro 355 | Tyr | Asp | Ser | Leu | Ala 360 | Thr | Tyr | Ala | Tyr | Glu 365 | Gly | Thr | Gly |
| Ser | Val 370 | Ala | Asp | Ser | Leu | Ser 375 | Ser | Leu | Glu | Ser | Val 380 | Thr | Thr | Asp | Ala |
| Asp 385 | Gln | Asp | Tyr | Asp | Tyr 390 | Leu | Ser | Asp | Trp | Gly 395 | Pro | Arg | Phe | Lys | Lys 400 |
| Leu | Ala | Asp | Met | Tyr 405 | Gly | Gly | Val | Asp | Ser 410 | Asp | Lys | Asp | Ser |

( 2 ) INFORMATION FOR SEQ ID NO:53:

( i ) SEQUENCE CHARACTERISTICS:
        ( A ) LENGTH: 2550 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:53:

```
CAGGAAATGC TCTTGGATCT CTGGACTCCA TTAATAATAT TATGGATTAC TCTTCCCCCT        60

TGCATTTACA TGGCTCCGAT GAATCAGTCT CAAGTTTTAA TGAGTGGATC CCCTTTGGAA       120
```

```
CTAAACAGTC TGGGTGAAGA ACAGCGAATT TTGAACCGCT CCAAAAGAGG CTGGGTTTGG    180
AATCAAATGT TTGTCCTGGA AGAGTTTTCT GGACCTGAAC CGATTCTTGT TGGCCGGCTA    240
CACACAGACC TGGATCCTGG GAGCAAAAAA ATCAAGTATA TCCTATCAGG TGATGGAGCT    300
GGGACCATAT TTCAAATAAA TGATGTAACT GGAGATATCC ATGCTATAAA AAGACTTGAC    360
CGGGAGGAAA AGGCTGAGTA TACCCTAACA GCTCAAGCAG TGGACTGGGA GACAAGCAAA    420
CCTCTGGAGC CTCCTTCTGA ATTTATTATT AAAGTTCAAG ACATCAATGA CAATGCACCA    480
GAGTTTCTTA ATGGACCCTA TCATGCTACT GTGCCAGAAA TGTCCATTTT GGGTACATCT    540
GTCACTAACG TCACTGCGAC CGACGCTGAT GACCCAGTTT ATGGAAACAG TGCAAAGTTG    600
GTTTATAGTA TATTGGAAGG GCAGCCTTAT TTTTCCATTG AGCCTGAAAC AGCTATTATA    660
AAAACTGCCC TTCCCAACAT GGACAGAGAA GCCAAGGAGG AGTACCTGGT TGTTATCCAA    720
GCCAAGATA TGGGTGGACA CTCTGGTGGC CTGTCTGGGA CCACGACACT TACAGTGACT     780
CTTACTGATG TTAATGACAA TCCTCCAAAA TTTGCACAGA GCCTGTATCA CTTCTCAGTA    840
CCGGAAGATG TGGTTCTTGG CACTGCAATA GGAAGGGTGA AGGCCAATGA TCAGGATATT    900
GGTGAAAATG CACAGTCATC ATATGATATC ATCGATGGAG ATGGAACAGC ACTTTTTGAA    960
ATCACTTCTG ATGCCCAGGC CCAGGATGGC ATTATAAGGC TAAGAAAACC TCTGGACTTT   1020
GAGACCAAAA AATCCTATAC GCTAAAGGAT GAGGCAGCCA ATGTCCATAT TGACCCACGC   1080
TTCAGTGGCA GGGGCCCTT TAAAGACACG GCGACAGTCA AATCGTGGT TGAAGATGCT     1140
GATGAGCCTC CGGTCTTCTC TTCACCGACT TACCTACTTG AAGTTCATGA AATGCTGCT    1200
CTAAACTCCG TGATTGGGCA AGTGACTGCT CGTGACCCTG ATATCACTTC CAGTCCTATA   1260
AGGTTTTCCA TCGACCGGCA CACTGACCTG GAGAGGCAGT TCAACATTAA TGCAGACGAT   1320
GGGAAGATAA CGCTGGCAAC ACCACTTGAC AGAGAATTAA GTGTATGGCA CAACATAACA   1380
ATCATTGCTA CTGAAATTAG GAACCACAGT CAGATATCAC GAGTACCTGT TGCTATTAAA   1440
GTGCTGGATG TCAATGACAA CGCCCCTGAA TTCGCATCCG AATATGAGGC ATTTTTATGT   1500
GAAAATGGAA AACCCGGCCA AGTCATTCAA ACTGTTAGCG CCATGGACAA AGATGATCCC   1560
AAAAACGGAC ATTATTTCTT ATACAGTCTC CTTCCAGAAA TGGTCAACAA TCCGAATTTC   1620
ACCATCAAGA AAAATGAAGA TAATTCCCTC AGTATTTTGG CAAAGCATAA TGGATTCAAC   1680
CGCCAGAAGC AAGAAGTCTA TCTTTTACCA ATCATAATCA GTGATAGTGG AAATCCTCCA   1740
CTGAGCAGCA CTAGCACCTT GACAATCAGG GTCTGTGGCT GCAGCAATGA CGGTGTCGTC   1800
CAGTCTTGCA ATGTCGAAGC TTATGTCCTT CCAATTGGAC TCAGTATGGG CGCCTTAATT   1860
GCCATATTAG CATGCATCAT TTTGCTGTTA GTCATCGTGG TGCTGTTTGT AACTCTACGG   1920
CGGCATCAAA AAAATGAACC ATTAATTATC AAAGATGATG AAGACGTTCG AGAAAACATC   1980
ATTCGCTACG ATGATGAAGG AGGAGGGGAG GAGGACACAG AGGCTTTTGA CATTGCAACT   2040
TTACAAAATC CAGATGGAAT TAATGGATTT TTACCCCGTA AGGATATTAA ACCAGATTTG   2100
CAGTTTATGC CAAGGCAAGG GCTTGCTCCA GTTCCAAATG GTGTTGATGT CGATGAATTT   2160
ATAAATGTAA GGCTGCATGA GGCAGATAAT GATCCCACAG CCCCGCCATA TGACTCCATT   2220
CAAATATATG CTATGAAGG CCGAGGGTCA GTGGCTGGCT CCCTCAGCTC CTTGGAGTCC   2280
ACCACATCAG ACTCAGACCA GAATTTTGAC TACCTCAGTG ACTGGGGTCC CCGCTTTAAG   2340
AGACTGGGCG AACTCTACTC TGTTGGTGAA AGTGACAAAG AAACTTGACA GTGGATTATA   2400
AATAAATCAC TGGAACTGAG CATTCTGTAA TATTCTAGGG TCACTCCCCT TAGATACAAC   2460
CAATGTGGCT ATTTGTTTAG AGGCAAGTTT AGCACCAGTC ATCTATAACT CAACCACATT   2520
```

TAATGTTGAC AAAAAGATAA TAAATAAAAA 2550

( 2 ) INFORMATION FOR SEQ ID NO:54:

( i ) SEQUENCE CHARACTERISTICS:
( A ) LENGTH: 793 amino acids
( B ) TYPE: amino acid
( D ) TOPOLOGY: linear ( i i ) MOLECULE TYPE: protein ( x i ) SEQUENCE DESCRIPTION: SEQ ID NO:54:

```
Met Leu Leu Asp Leu Trp Thr Pro Leu Ile Ile Leu Trp Ile Thr Leu
 1               5                  10                  15
Pro Pro Cys Ile Tyr Met Ala Pro Met Asn Gln Ser Gln Val Leu Met
            20                  25                  30
Ser Gly Ser Pro Leu Gln Leu Asn Ser Leu Gly Glu Glu Gln Arg Ile
        35                  40                  45
Leu Asn Arg Ser Lys Arg Gly Trp Val Trp Asn Gln Met Phe Val Leu
    50                  55                  60
Glu Glu Phe Ser Gly Pro Glu Pro Ile Leu Val Gly Arg Leu His Thr
65                  70                  75                  80
Asp Leu Asp Pro Gly Ser Lys Lys Ile Lys Tyr Ile Leu Ser Gly Asp
                85                  90                  95
Gly Ala Gly Thr Ile Phe Gln Ile Asn Asp Val Thr Gly Asp Ile His
            100                 105                 110
Ala Ile Lys Arg Leu Asp Arg Glu Glu Lys Ala Glu Tyr Thr Leu Thr
        115                 120                 125
Ala Gln Ala Val Asp Trp Glu Thr Ser Lys Pro Leu Glu Pro Pro Ser
    130                 135                 140
Glu Phe Ile Ile Lys Val Gln Asp Ile Asn Asp Asn Ala Pro Glu Phe
145                 150                 155                 160
Leu Asn Gly Pro Tyr His Ala Thr Val Pro Glu Met Ser Ile Leu Gly
                165                 170                 175
Thr Ser Val Thr Asn Val Thr Ala Thr Asp Ala Asp Asp Pro Val Tyr
            180                 185                 190
Gly Asn Ser Ala Lys Leu Val Tyr Ser Ile Leu Glu Gly Gln Pro Tyr
        195                 200                 205
Phe Ser Ile Glu Pro Glu Thr Ala Ile Ile Lys Thr Ala Leu Pro Asn
    210                 215                 220
Met Asp Arg Glu Ala Lys Glu Glu Tyr Leu Val Val Ile Gln Ala Lys
225                 230                 235                 240
Asp Met Gly Gly His Ser Gly Gly Leu Ser Gly Thr Thr Thr Leu Thr
                245                 250                 255
Val Thr Leu Thr Asp Val Asn Asp Asn Pro Pro Lys Phe Ala Gln Ser
            260                 265                 270
Leu Tyr His Phe Ser Val Pro Glu Asp Val Val Leu Gly Thr Ala Ile
        275                 280                 285
Gly Arg Val Lys Ala Asn Asp Gln Asp Ile Gly Glu Asn Ala Gln Ser
    290                 295                 300
Ser Tyr Asp Ile Ile Asp Gly Asp Gly Thr Ala Leu Phe Glu Ile Thr
305                 310                 315                 320
Ser Asp Ala Gln Ala Gln Asp Gly Ile Ile Arg Leu Arg Lys Pro Leu
                325                 330                 335
Asp Phe Glu Thr Lys Lys Ser Tyr Thr Leu Lys Asp Glu Ala Ala Asn
            340                 345                 350
```

```
Val His Ile Asp Pro Arg Phe Ser Gly Arg Gly Pro Phe Lys Asp Thr
        355                 360                 365

Ala Thr Val Lys Ile Val Val Glu Asp Ala Asp Glu Pro Pro Val Phe
    370                 375                 380

Ser Ser Pro Thr Tyr Leu Leu Glu Val His Glu Asn Ala Ala Leu Asn
385                 390                 395                 400

Ser Val Ile Gly Gln Val Thr Ala Arg Asp Pro Asp Ile Thr Ser Ser
                405                 410                 415

Pro Ile Arg Phe Ser Ile Asp Arg His Thr Asp Leu Glu Arg Gln Phe
            420                 425                 430

Asn Ile Asn Ala Asp Asp Gly Lys Ile Thr Leu Ala Thr Pro Leu Asp
        435                 440                 445

Arg Glu Leu Ser Val Trp His Asn Ile Thr Ile Ile Ala Thr Glu Ile
    450                 455                 460

Arg Asn His Ser Gln Ile Ser Arg Val Pro Val Ala Ile Lys Val Leu
465                 470                 475                 480

Asp Val Asn Asp Asn Ala Pro Glu Phe Ala Ser Glu Tyr Glu Ala Phe
                485                 490                 495

Leu Cys Glu Asn Gly Lys Pro Gly Gln Val Ile Gln Thr Val Ser Ala
            500                 505                 510

Met Asp Lys Asp Asp Pro Lys Asn Gly His Tyr Phe Leu Tyr Ser Leu
        515                 520                 525

Leu Pro Glu Met Val Asn Asn Pro Asn Phe Thr Ile Lys Lys Asn Glu
    530                 535                 540

Asp Asn Ser Leu Ser Ile Leu Ala Lys His Asn Gly Phe Asn Arg Gln
545                 550                 555                 560

Lys Gln Glu Val Tyr Leu Leu Pro Ile Ile Ile Ser Asp Ser Gly Asn
                565                 570                 575

Pro Pro Leu Ser Ser Thr Ser Thr Leu Thr Ile Arg Val Cys Gly Cys
            580                 585                 590

Ser Asn Asp Gly Val Val Gln Ser Cys Asn Val Glu Ala Tyr Val Leu
        595                 600                 605

Pro Ile Gly Leu Ser Met Gly Ala Leu Ile Ala Ile Leu Ala Cys Ile
    610                 615                 620

Ile Leu Leu Leu Val Ile Val Val Leu Phe Val Thr Leu Arg Arg His
625                 630                 635                 640

Gln Lys Asn Glu Pro Leu Ile Ile Lys Asp Asp Glu Asp Val Arg Glu
                645                 650                 655

Asn Ile Ile Arg Tyr Asp Asp Glu Gly Gly Gly Glu Glu Asp Thr Glu
            660                 665                 670

Ala Phe Asp Ile Ala Thr Leu Gln Asn Pro Asp Gly Ile Asn Gly Phe
        675                 680                 685

Leu Pro Arg Lys Asp Ile Lys Pro Asp Leu Gln Phe Met Pro Arg Gln
    690                 695                 700

Gly Leu Ala Pro Val Pro Asn Gly Val Asp Val Asp Glu Phe Ile Asn
705                 710                 715                 720

Val Arg Leu His Glu Ala Asp Asn Asp Pro Thr Ala Pro Pro Tyr Asp
                725                 730                 735

Ser Ile Gln Ile Tyr Gly Tyr Glu Gly Arg Gly Ser Val Ala Gly Ser
            740                 745                 750

Leu Ser Ser Leu Glu Ser Thr Thr Ser Asp Ser Asp Gln Asn Phe Asp
        755                 760                 765

Tyr Leu Ser Asp Trp Gly Pro Arg Phe Lys Arg Leu Gly Glu Leu Tyr
```

```
                770                      775                      780
Ser  Val  Gly  Glu  Ser  Asp  Lys  Glu  Thr
785                      790
```

( 2 ) INFORMATION FOR SEQ ID NO:55:

( i ) SEQUENCE CHARACTERISTICS:
        ( A ) LENGTH: 730 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 2..730

( x i ) SEQUENCE DESCRIPTION: SEQ ID NO:55:

```
G  AAT  TCG  AGC  TCG  GTA  CCC  GGG  GAT  CCT  CTA  GAG  TCG  ACC  TGC  AGT          46
   Asn  Ser  Ser  Ser  Val  Pro  Gly  Asp  Pro  Leu  Glu  Ser  Thr  Cys  Ser
   1                   5                        10                       15

GCT  GAA  GCC  CTG  CTC  CTC  CCT  GCC  GGC  CTC  AGC  ACT  GGG  GCC  TTG  ATC        94
Ala  Glu  Ala  Leu  Leu  Leu  Pro  Ala  Gly  Leu  Ser  Thr  Gly  Ala  Leu  Ile
                    20                        25                        30

GCC  ATC  CTC  CTC  TGC  ATC  ATC  ATT  CTA  CTG  GTT  ATA  GTA  GTA  CTG  TTT       142
Ala  Ile  Leu  Leu  Cys  Ile  Ile  Ile  Leu  Leu  Val  Ile  Val  Val  Leu  Phe
               35                        40                        45

GCA  GCT  CTG  AAA  AGA  CAG  CGA  AAA  AAA  GAG  CCT  CTG  ATC  TTG  TCA  AAA       190
Ala  Ala  Leu  Lys  Arg  Gln  Arg  Lys  Lys  Glu  Pro  Leu  Ile  Leu  Ser  Lys
               50                        55                        60

GAA  GAT  ATC  AGA  GAC  AAC  ATT  GTG  AGC  TAT  AAC  GAT  GAG  GGT  GGT  GGA       238
Glu  Asp  Ile  Arg  Asp  Asn  Ile  Val  Ser  Tyr  Asn  Asp  Glu  Gly  Gly  Gly
          65                        70                        75

GAG  GAG  GAC  ACC  CAG  GCC  TTT  GAT  ATC  GGC  ACC  CTG  AGG  AAT  CCT  GCA       286
Glu  Glu  Asp  Thr  Gln  Ala  Phe  Asp  Ile  Gly  Thr  Leu  Arg  Asn  Pro  Ala
80                        85                        90                        95

GCC  ATT  GAG  GAA  AAA  AAG  CTC  CGG  CGA  GAT  ATT  ATT  CCA  GAA  ACG  TTA       334
Ala  Ile  Glu  Glu  Lys  Lys  Leu  Arg  Arg  Asp  Ile  Ile  Pro  Glu  Thr  Leu
                    100                       105                       110

TTT  ATT  CCT  CGG  AGG  ACT  CCT  ACA  GCT  CCA  GAT  AAC  ACG  GAC  GTC  CGG       382
Phe  Ile  Pro  Arg  Arg  Thr  Pro  Thr  Ala  Pro  Asp  Asn  Thr  Asp  Val  Arg
               115                       120                       125

GAT  TTC  ATT  AAT  GAA  AGG  CTA  AAA  GAG  CAT  GAT  CTT  GAC  CCC  ACC  GCA       430
Asp  Phe  Ile  Asn  Glu  Arg  Leu  Lys  Glu  His  Asp  Leu  Asp  Pro  Thr  Ala
          130                       135                       140

CCC  CCC  TAC  GAC  TCA  CTT  GCA  ACC  TAT  GCC  TAT  GAA  GGA  AAT  GAT  TCC       478
Pro  Pro  Tyr  Asp  Ser  Leu  Ala  Thr  Tyr  Ala  Tyr  Glu  Gly  Asn  Asp  Ser
145                       150                       155

ATT  GCT  GAA  TCT  CTG  AGT  TCA  TTA  GAA  TCA  GGT  ACT  ACT  GAA  GGA  GAC       526
Ile  Ala  Glu  Ser  Leu  Ser  Ser  Leu  Glu  Ser  Gly  Thr  Thr  Glu  Gly  Asp
160                       165                       170                       175

CAA  AAC  TAC  GAT  TAC  CTC  CGA  GAA  TGG  GGC  CCT  CGG  TTT  AAT  AAG  CTA       574
Gln  Asn  Tyr  Asp  Tyr  Leu  Arg  Glu  Trp  Gly  Pro  Arg  Phe  Asn  Lys  Leu
               180                       185                       190

GCA  GAA  ATG  TAT  GGT  GGT  GGG  GAA  AGT  GAC  AAA  GAC  TCT  TAA  CGT  AGG       622
Ala  Glu  Met  Tyr  Gly  Gly  Gly  Glu  Ser  Asp  Lys  Asp  Ser   *   Arg  Arg
          195                       200                       205

ATA  TAT  GTT  CTG  TTC  AAA  CAA  GAG  AAA  GTA  ACT  CTA  CCC  ATG  CTG  TCT       670
Ile  Tyr  Val  Leu  Phe  Lys  Gln  Glu  Lys  Val  Thr  Leu  Pro  Met  Leu  Ser
               210                       215                       220

CCA  CTT  CAC  AAT  ATT  TGA  TAT  TCA  GGA  GCA  TTT  CCT  GCA  GTC  AGC  ACA       718
Pro  Leu  His  Asn  Ile   *   Tyr  Ser  Gly  Ala  Phe  Pro  Ala  Val  Ser  Thr
```

-continued

```
              225                       230                       235
ATT  TTT  TTC  TCA                                                                                    730
Ile  Phe  Phe  Ser
240
```

( 2 ) INFORMATION FOR SEQ ID NO:56:

( i ) SEQUENCE CHARACTERISTICS:
        ( A ) LENGTH: 241 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Asn  Ser  Ser  Ser  Val  Pro  Gly  Asp  Pro  Leu  Glu  Ser  Thr  Cys  Ser  Ala
 1                   5                        10                       15

Glu  Ala  Leu  Leu  Leu  Pro  Ala  Gly  Leu  Ser  Thr  Gly  Ala  Leu  Ile  Ala
               20                       25                       30

Ile  Leu  Leu  Cys  Ile  Ile  Ile  Leu  Leu  Val  Ile  Val  Val  Leu  Phe  Ala
               35                       40                       45

Ala  Leu  Lys  Arg  Gln  Arg  Lys  Lys  Glu  Pro  Leu  Ile  Leu  Ser  Lys  Glu
      50                        55                       60

Asp  Ile  Arg  Asp  Asn  Ile  Val  Ser  Tyr  Asn  Asp  Glu  Gly  Gly  Gly  Glu
 65                       70                       75                        80

Glu  Asp  Thr  Gln  Ala  Phe  Asp  Ile  Gly  Thr  Leu  Arg  Asn  Pro  Ala  Ala
                    85                       90                       95

Ile  Glu  Glu  Lys  Lys  Leu  Arg  Arg  Asp  Ile  Ile  Pro  Glu  Thr  Leu  Phe
                   100                      105                     110

Ile  Pro  Arg  Arg  Thr  Pro  Thr  Ala  Pro  Asp  Asn  Thr  Asp  Val  Arg  Asp
               115                      120                      125

Phe  Ile  Asn  Glu  Arg  Leu  Lys  Glu  His  Asp  Leu  Asp  Pro  Thr  Ala  Pro
130                      135                      140

Pro  Tyr  Asp  Ser  Leu  Ala  Thr  Tyr  Ala  Tyr  Glu  Gly  Asn  Asp  Ser  Ile
145                      150                      155                      160

Ala  Glu  Ser  Leu  Ser  Ser  Leu  Glu  Ser  Gly  Thr  Thr  Glu  Gly  Asp  Gln
               165                      170                      175

Asn  Tyr  Asp  Tyr  Leu  Arg  Glu  Trp  Gly  Pro  Arg  Phe  Asn  Lys  Leu  Ala
               180                      185                      190

Glu  Met  Tyr  Gly  Gly  Gly  Glu  Ser  Asp  Lys  Asp  Ser  Arg  Arg  Ile  Tyr
               195                      200                      205

Val  Leu  Phe  Lys  Gln  Glu  Lys  Val  Thr  Leu  Pro  Met  Leu  Ser  Pro  Leu
      210                      215                      220

His  Asn  Ile  Tyr  Ser  Gly  Ala  Phe  Pro  Ala  Val  Ser  Thr  Ile  Phe  Phe
225                      230                      235                      240

Ser
```

( 2 ) INFORMATION FOR SEQ ID NO:57:

( i ) SEQUENCE CHARACTERISTICS:
        ( A ) LENGTH: 2625 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:57:

```
CGGCAGCCCT  GACGTGATGA  GCTCAACCAG  CAGAGACATT  CCATCCCAAG  AGAGGTCTGC    60
```

```
GTGACGCGTC  CGGGAGGCCA  CCCTCAGCAA  GACCACCGTA  CAGTTGGTGG  AAGGGGTGAC   120
AGCTGCATTC  TCCTGTGCCT  ACCACGTAAC  CAAAAATGAA  GGAGAACTAC  TGTTTACAAG   180
CCGCCCTGGT  GTGCCTGGGC  ATGCTGTGCC  ACAGCCATGC  CTTTGCCCCA  GAGCGGCGGG   240
GGCACCTGCG  GCCCTCCTTC  CATGGGCACC  ATGAGAAGGG  CAAGGAGGGG  CAGGTGCTAC   300
AGCGCTCCAA  GCGTGGCTGG  GTCTGGAACC  AGTTCTTCGT  GATAGAGGAG  TACACCGGGC   360
CTGACCCCGT  GCTTGTGGGC  AGGCTTCATT  CAGATATTGA  CTCTGGTGAT  GGGAACATTA   420
AATACATTCT  CTCAGGGGAA  GGAGCTGGAA  CCATTTTTGT  GATTGATGAC  AAATCAGGGA   480
ACATTCATGC  CACCAAGACG  TTGGATCGAG  AAGAGAGAGC  CCAGTACACG  TTGATGGCTC   540
AGGCGGTGGA  CAGGGACACC  AATCGGCCAC  TGGAGCCACC  GTCGGAATTC  ATTGTCAAGG   600
TCCAGGACAT  TAATGACAAC  CCTCCGGAGT  TCCTGCACGA  GACCTATCAT  GCCAACGTGC   660
CTGAGAGGTC  CAATGTGGGA  ACGTCAGTAA  TCCAGGTGAC  AGCTTCAGAT  GCAGATGACC   720
CCACTTATGG  AAATAGCGCC  AAGTTAGTGT  ACAGTATCCT  CGAAGGACAA  CCCTATTTTT   780
CGGTGGAAGC  ACAGACAGGT  ATCATCAGAA  CAGCCCTACC  CAACATGGAC  AGGGAGGCCA   840
AGGAGGAGTA  CCACGTGGTG  ATCCAGGCCA  AGGACATGGG  TGGACATATG  GGCGGACTCT   900
CAGGGACAAC  CAAAGTGACG  ATCACACTGA  CCGATGTCAA  TGACAACCCA  CCAAAGTTTC   960
CGCAGAGGCT  ATACCAGATG  TCTGTGTCAG  AAGCAGCCGT  CCCTGGGGAG  GAAGTAGGAA  1020
GAGTGAAAGC  TAAAGATCCA  GACATTGGAG  AAAATGGCTT  AGTCACATAC  AATATTGTTG  1080
ATGGAGATGG  TATGGAATCG  TTTGAAATCA  CAACGGACTA  TGAAACACAG  GAGGGGGTGA  1140
TAAAGCTGAA  AAAGCCTGTA  GATTTTGAAA  CCGAAGAGC   CTATAGCTTG  AAGGTAGAGG  1200
CAGCCAACGT  GCACATCGAC  CCGAAGTTTA  TCAGCAATGG  CCCTTTCAAG  GACACTGTGA  1260
CCGTCAAGAT  CTCAGTAGAA  GATGCTGATG  AGCCCCTAT   GTTCTTGGCC  CAAGTTACA   1320
TCCACGAAGT  CCAAGAAAAT  GCAGCTGCTG  GCACCGTGGT  TGGGAGAGTG  CATGCCAAAG  1380
ACCCTGATGC  TGCCAACAGC  CCGATAAGGT  ATTCCATCGA  TCGTCACACT  GACCTCGACA  1440
GATTTTTCAC  TATTAATCCA  GAGGATGGTT  TTATTAAAAC  TACAAAACCT  CTGGATAGAG  1500
AGGAAACAGC  CTGGCTCAAC  ATCACTGTCT  TTGCAGCAGA  AATCCACAAT  CGGCATCAGG  1560
AAGCCCAAGT  CCCAGTGGCC  ATTAGGGTCC  TTGATGTCAA  CGATAATGCT  CCCAAGTTTG  1620
CTGCCCCTTA  TGAAGGTTTC  ATCTGTGAGA  GTGATCAGAC  CAAGCCACTT  TCCAACCAGC  1680
CAATTGTTAC  AATTAGTGCA  GATGACAAGG  ATGACACGGC  CAATGGACCA  AGATTTATCT  1740
TCAGCCTACC  CCCTGAAATC  ATTCACAATC  CAAATTTCAC  AGTCAGAGAC  AACCGAGATA  1800
ACACAGCAGG  CGTGTACGCC  CGGCGTGGAG  GGTTCAGTCG  GCAGAAGCAG  GACTTGTACC  1860
TTCTGCCCAT  AGTGATCAGC  GATGGCGGCA  TCCCGCCCAT  GAGTAGCACC  AACACCCTCA  1920
CCATCAAAGT  CTGCGGGTGC  GACGTGAACG  GGCACTGCT   CTCCTGCAAC  GCAGAGGCCT  1980
ACATTCTGAA  CGCCGGCCTG  AGCACAGGCG  CCCTGATCGC  CATCCTCGCC  TGCATCGTCA  2040
TTCTCCTGGT  CATTGTAGTA  TTGTTTGTGA  CCCTGAGAAG  GCAAAAGAAA  GAACCACTCA  2100
TTGTCTTTGA  GGAAGAAGAT  GTCCGTGAGA  ACATCATTAC  TTATGATGAT  GAAGGGGGTG  2160
GGGAAGAAGA  CACAGAAGCC  TTTGATATTG  CCACCCTCCA  GAATCCTGAT  GGTATCAATG  2220
GATTTATCCC  CCGCAAAGAC  ATCAAACCTG  AGTATCAGTA  CATGCCTAGA  CCTGGGCTCC  2280
GGCCAGCGCC  CAACAGCGTG  GATGTCGATG  ACTTCATCAA  CACGAGAATA  CAGGAGGCAG  2340
ACAATGACCC  CACGGCTCCT  CCTTATGACT  CCATTCAAAT  CTACGGTTAT  GAAGGCAGGG  2400
GCTCAGTGGC  CGGGTCCCTG  AGCTCCCTAG  AGTCGGCCAC  CACAGATTCA  GACTTGGACT  2460
```

```
ATGATTATCT ACAGAACTGG GGACCTCGTT TTAAGAAACT AGCAGATTTG TATGGTTCCA    2520

AAGACACTTT TGATGACGAT TCTTAACAAT AACGATACAA ATTTGGCCTT AAGAACTGTG    2580

TCTGGCGTTC TCAAGAATCT AGAAGATGTG TAACAGGTAT TTTTT                    2625
```

( 2 ) INFORMATION FOR SEQ ID NO:58:

( i ) SEQUENCE CHARACTERISTICS:
        ( A ) LENGTH: 796 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Met Lys Glu Asn Tyr Cys Leu Gln Ala Ala Leu Val Cys Leu Gly Met
 1               5                  10                  15

Leu Cys His Ser His Ala Phe Ala Pro Glu Arg Arg Gly His Leu Arg
            20                  25                  30

Pro Ser Phe His Gly His His Glu Lys Gly Lys Glu Gly Gln Val Leu
        35                  40                  45

Gln Arg Ser Lys Arg Gly Trp Val Trp Asn Gln Phe Phe Val Ile Glu
    50                  55                  60

Glu Tyr Thr Gly Pro Asp Pro Val Leu Val Gly Arg Leu His Ser Asp
65                  70                  75                  80

Ile Asp Ser Gly Asp Gly Asn Ile Lys Tyr Ile Leu Ser Gly Glu Gly
                85                  90                  95

Ala Gly Thr Ile Phe Val Ile Asp Asp Lys Ser Gly Asn Ile His Ala
               100                 105                 110

Thr Lys Thr Leu Asp Arg Glu Glu Arg Ala Gln Tyr Thr Leu Met Ala
           115                 120                 125

Gln Ala Val Asp Arg Asp Thr Asn Arg Pro Leu Glu Pro Pro Ser Glu
    130                 135                 140

Phe Ile Val Lys Val Gln Asp Ile Asn Asp Asn Pro Pro Glu Phe Leu
145                 150                 155                 160

His Glu Thr Tyr His Ala Asn Val Pro Glu Arg Ser Asn Val Gly Thr
                165                 170                 175

Ser Val Ile Gln Val Thr Ala Ser Asp Ala Asp Asp Pro Thr Tyr Gly
           180                 185                 190

Asn Ser Ala Lys Leu Val Tyr Ser Ile Leu Glu Gly Gln Pro Tyr Phe
    195                 200                 205

Ser Val Glu Ala Gln Thr Gly Ile Ile Arg Thr Ala Leu Pro Asn Met
210                 215                 220

Asp Arg Glu Ala Lys Glu Glu Tyr His Val Val Ile Gln Ala Lys Asp
225                 230                 235                 240

Met Gly Gly His Met Gly Gly Leu Ser Gly Thr Thr Lys Val Thr Ile
                245                 250                 255

Thr Leu Thr Asp Val Asn Asp Asn Pro Pro Lys Phe Pro Gln Arg Leu
           260                 265                 270

Tyr Gln Met Ser Val Ser Glu Ala Ala Val Pro Gly Glu Glu Val Gly
    275                 280                 285

Arg Val Lys Ala Lys Asp Pro Asp Ile Gly Glu Asn Gly Leu Val Thr
290                 295                 300

Tyr Asn Ile Val Asp Gly Asp Gly Met Glu Ser Phe Glu Ile Thr Thr
305                 310                 315                 320

Asp Tyr Glu Thr Gln Glu Gly Val Ile Lys Leu Lys Lys Pro Val Asp
            325                 330                 335
```

```
Phe Glu Thr Glu Arg Ala Tyr Ser Leu Lys Val Glu Ala Ala Asn Val
            340                 345                 350
His Ile Asp Pro Lys Phe Ile Ser Asn Gly Pro Phe Lys Asp Thr Val
        355                 360                 365
Thr Val Lys Ile Ser Val Glu Asp Ala Asp Glu Pro Pro Met Phe Leu
        370                 375                 380
Ala Pro Ser Tyr Ile His Glu Val Gln Glu Asn Ala Ala Ala Gly Thr
385                     390                 395                 400
Val Val Gly Arg Val His Ala Lys Asp Pro Asp Ala Ala Asn Ser Pro
                405                 410                 415
Ile Arg Tyr Ser Ile Asp Arg His Thr Asp Leu Asp Arg Phe Phe Thr
            420                 425                 430
Ile Asn Pro Glu Asp Gly Phe Ile Lys Thr Thr Lys Pro Leu Asp Arg
        435                 440                 445
Glu Glu Thr Ala Trp Leu Asn Ile Thr Val Phe Ala Ala Glu Ile His
    450                 455                 460
Asn Arg His Gln Glu Ala Gln Val Pro Val Ala Ile Arg Val Leu Asp
465                     470                 475                 480
Val Asn Asp Asn Ala Pro Lys Phe Ala Ala Pro Tyr Glu Gly Phe Ile
                485                 490                 495
Cys Glu Ser Asp Gln Thr Lys Pro Leu Ser Asn Gln Pro Ile Val Thr
            500                 505                 510
Ile Ser Ala Asp Asp Lys Asp Asp Thr Ala Asn Gly Pro Arg Phe Ile
        515                 520                 525
Phe Ser Leu Pro Pro Glu Ile Ile His Asn Pro Asn Phe Thr Val Arg
    530                 535                 540
Asp Asn Arg Asp Asn Thr Ala Gly Val Tyr Ala Arg Arg Gly Gly Phe
545                     550                 555                 560
Ser Arg Gln Lys Gln Asp Leu Tyr Leu Leu Pro Ile Val Ile Ser Asp
                565                 570                 575
Gly Gly Ile Pro Pro Met Ser Ser Thr Asn Thr Leu Thr Ile Lys Val
            580                 585                 590
Cys Gly Cys Asp Val Asn Gly Ala Leu Leu Ser Cys Asn Ala Glu Ala
        595                 600                 605
Tyr Ile Leu Asn Ala Gly Leu Ser Thr Gly Ala Leu Ile Ala Ile Leu
    610                 615                 620
Ala Cys Ile Val Ile Leu Leu Val Ile Val Val Leu Phe Val Thr Leu
625                     630                 635                 640
Arg Arg Gln Lys Lys Glu Pro Leu Ile Val Phe Glu Glu Glu Asp Val
                645                 650                 655
Arg Glu Asn Ile Ile Thr Tyr Asp Asp Glu Gly Gly Gly Glu Glu Asp
            660                 665                 670
Thr Glu Ala Phe Asp Ile Ala Thr Leu Gln Asn Pro Asp Gly Ile Asn
        675                 680                 685
Gly Phe Ile Pro Arg Lys Asp Ile Lys Pro Glu Tyr Gln Tyr Met Pro
    690                 695                 700
Arg Pro Gly Leu Arg Pro Ala Pro Asn Ser Val Asp Val Asp Asp Phe
705                     710                 715                 720
Ile Asn Thr Arg Ile Gln Glu Ala Asp Asn Asp Pro Thr Ala Pro Pro
                725                 730                 735
Tyr Asp Ser Ile Gln Ile Tyr Gly Tyr Glu Gly Arg Gly Ser Val Ala
            740                 745                 750
Gly Ser Leu Ser Ser Leu Glu Ser Ala Thr Thr Asp Ser Asp Leu Asp
```

|  |  |  | 755 |  |  |  |  | 760 |  |  |  |  | 765 |  |  |  |
|---|---|---|---|---|---|---|---|---|---|---|---|---|---|---|---|---|
| Tyr | Asp | Tyr | Leu | Gln | Asn | Trp | Gly | Pro | Arg | Phe | Lys | Lys | Leu | Ala | Asp |
|  | 770 |  |  |  |  | 775 |  |  |  |  | 780 |  |  |  |  |
| Leu | Tyr | Gly | Ser | Lys | Asp | Thr | Phe | Asp | Asp | Asp | Ser |  |  |  |  |
| 785 |  |  |  |  | 790 |  |  |  |  | 795 |  |  |  |  |  |

( 2 ) INFORMATION FOR SEQ ID NO:59:

( i ) SEQUENCE CHARACTERISTICS:
        ( A ) LENGTH: 2521 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:59:

| | | | | | |
|---|---|---|---|---|---|
| CGGTGGAGGC | CACAGACACC | TCAAACCTGG | ATTCCACAAT | TCTACGTTAA | GTGTTGGAGT | 60 |
| TTTTATTACT | CTGCTGTAGG | AAAGCCTTTG | CCAATGCTTA | CAAGGAACTG | TTTATCCCTG | 120 |
| CTTCTCTGGG | TTCTGTTTGA | TGGAGGTCTC | CTAACACCAC | TACAACCACA | GCCACAGCAG | 180 |
| ACTTTAGCCA | CAGAGCCAAG | AGAAAATGTT | ATCCATCTGC | CAGGACAACG | GTCACATTTC | 240 |
| CAACGTGTTA | AACGTGGCTG | GGTATGGAAT | CAATTTTTG | TGCTGGAAGA | ATACGTGGGC | 300 |
| TCCGAGCCTC | AGTATGTGGG | AAAGCTCCAT | TCCGACTTAG | ACAAGGGAGA | GGGCACTGTG | 360 |
| AAATACACCC | TCTCAGGAGA | TGGCGCTGGC | ACCGTTTTA | CCATTGATGA | AACCACAGGG | 420 |
| GACATTCATG | CAATAAGGAG | CCTAGATAGA | GAAGAGAAAC | CTTTCTACAC | TCTTCGTGCT | 480 |
| CAGGCTGTGG | ACATAGAAAC | CAGAAAGCCC | CTGGAGCCTG | AATCAGAATT | CATCATCAAA | 540 |
| GTGCAGGATA | TTAATGATAA | TGAGCCAAAG | TTTTGGATG | GACCTTATGT | TGCTACTGTT | 600 |
| CCAGAAATGT | CTCCTGTGGG | TGCATATGTA | CTCCAGGTCA | AGGCCACAGA | TGCAGATGAC | 660 |
| CCGACCTATG | GAAACAGTGC | CAGAGTCGTT | TACAGCATTC | TTCAGGGACA | ACCTTATTTC | 720 |
| TCTATTGATC | CCAAGACAGG | TGTTATTAGA | ACAGCTTTGC | CAAACATGGA | CAGAGAAGTC | 780 |
| AAAGAACAAT | ATCAAGTACT | CATCCAAGCC | AAGGATATGG | GAGGACAGCT | TGGAGGATTA | 840 |
| GCCGGAACAA | CAATAGTCAA | CATCACTCTC | ACCGATGTCA | ATGACAATCC | ACCTCGATTC | 900 |
| CCCAAAAGCA | TCTTCCACTT | GAAAGTTCCT | GAGTCTTCCC | CTATTGGTTC | AGCTATTGGA | 960 |
| AGAATAAGAG | CTGTGGATCC | TGATTTTGGA | CAAAATGCAG | AAATTGAATA | CAATATTGTT | 1020 |
| CCAGGAGATG | GGGGAAATTT | GTTTGACATC | GTCACAGATG | AGGATACACA | AGAGGGAGTC | 1080 |
| ATCAAATTGA | AAAAGCCTTT | AGATTTTGAA | ACAAAGAAGG | CATACACTTT | CAAAGTTGAG | 1140 |
| GCTTCCAACC | TTCACCTTGA | CCACCGGTTT | CACTCGGCGG | GCCCTTTCAA | AGACACAGCT | 1200 |
| ACGGTGAAGA | TCAGCGTGCT | GGACGTAGAT | GAGCCACCGG | TTTTCAGCAA | GCCGCTCTAC | 1260 |
| ACCATGGAGG | TTTATGAAGA | CACTCCGGTA | GGGACCATCA | TTGGCGCTGT | CACTGCTCAA | 1320 |
| GACCTGGATG | TAGGCAGCGG | TGCTGTTAGG | TACTTCATAG | ATTGGAAGAG | TGATGGGGAC | 1380 |
| AGCTACTTTA | CAATAGATGG | AAATGAAGGA | ACCATCGCCA | CTAATGAATT | ACTAGACAGA | 1440 |
| GAAAGCACTG | CGCAGTATAA | TTTCTCCATA | ATTGCGAGTA | AAGTTAGTAA | CCCTTTATTG | 1500 |
| ACCAGCAAAG | TCAATATACT | GATTAATGTC | TTAGATGTAA | ATGAATTTCC | TCCAGAAATA | 1560 |
| TCTGTGCCAT | ATGAGACAGC | CGTGTGTGAA | AATGCCAAGC | CAGGACAGAT | AATTCAGATA | 1620 |
| GTCAGTGCTG | CAGACCGAGA | TCTTTCACCT | GCTGGGCAAC | AATTCTCCTT | TAGATTATCA | 1680 |
| CCTGAGGCTG | CTATCAAACC | AAATTTACA | GTTCGTGACT | TCAGAACAA | CACAGCGGGG | 1740 |
| ATTGAAACCC | GAAGAAATGG | ATACAGCCGC | AGGCAGCAAG | AGTTGTATTT | CCTCCCTGTT | 1800 |

-continued

```
GTAATAGAAG ACAGCAGCTA CCCTGTCCAG AGCAGCACAA ACACAATGAC TATTCGAGTC  1860
TGTAGATGTG ACTCTGATGG CACCATCCTG TCTTGTAATG TGGAAGCAAT TTTTCTACCT  1920
GTAGGACTTA GCACTGGGGC GTTGATTGCA ATTCTACTAT GCATTGTTAT ACTCTTAGCC  1980
ATAGTTGTAC TGTATGTAGC ACTGCGAAGG CAGAAGAAAA AGCACACCCT GATGACCTCT  2040
AAAGAAGACA TCAGAGACAA CGTCATCCAT TACGATGATG AAGGAGGTGG GGAGGAAGAT  2100
ACCCAGGCTT TCGACATCGG GGCTCTGAGA AACCCAAAAG TGATTGAGGA GAACAAAATT  2160
CGCAGGGATA TAAAACCAGA CTCTCTCTGT TTACCTCGTC AGAGACCACC CATGGAAGAT  2220
AACACAGACA TAAGGGATTT CATTCATCAA AGGCTACAGG AAAATGATGT AGATCCAACT  2280
GCCCCACCAA TCGATTCACT GGCCACATAT GCCTACGAAG GGAGTGGGTC CGTGGCAGAG  2340
TCCCTCAGCT CTATAGACTC TCTCACCACA GAAGCCGACC AGGACTATGA CTATCTGACA  2400
GACTGGGGAC CCCGCTTTAA AGTCTTGGCA GACATGTTTG GCGAAGAAGA GAGTTATAAC  2460
CCTGATAAAG TCACTTAAGG GAGTCGTGGA GGCTAAAATA CAACCGAGAG GGAGATTTT   2520
T                                                                  2521
```

( 2 ) INFORMATION FOR SEQ ID NO:60:

( i ) SEQUENCE CHARACTERISTICS:
        ( A ) LENGTH: 794 amino acids
        ( B ) TYPE: amino acid
        ( D ) TOPOLOGY: linear ( i i ) MOLECULE TYPE: protein ( x i ) SEQUENCE DESCRIPTION: SEQ ID NO:60:

```
Met Leu Thr Arg Asn Cys Leu Ser Leu Leu Leu Trp Val Leu Phe Asp
 1               5                  10                  15
Gly Gly Leu Leu Thr Pro Leu Gln Pro Gln Pro Gln Gln Thr Leu Ala
            20                  25                  30
Thr Glu Pro Arg Glu Asn Val Ile His Leu Pro Gly Gln Arg Ser His
        35                  40                  45
Phe Gln Arg Val Lys Arg Gly Trp Val Trp Asn Gln Phe Phe Val Leu
    50                  55                  60
Glu Glu Tyr Val Gly Ser Glu Pro Gln Tyr Val Gly Lys Leu His Ser
65                  70                  75                  80
Asp Leu Asp Lys Gly Glu Gly Thr Val Lys Tyr Thr Leu Ser Gly Asp
                85                  90                  95
Gly Ala Gly Thr Val Phe Thr Ile Asp Glu Thr Thr Gly Asp Ile His
            100                 105                 110
Ala Ile Arg Ser Leu Asp Arg Glu Glu Lys Pro Phe Tyr Thr Leu Arg
        115                 120                 125
Ala Gln Ala Val Asp Ile Glu Thr Arg Lys Pro Leu Glu Pro Glu Ser
    130                 135                 140
Glu Phe Ile Ile Lys Val Gln Asp Ile Asn Asp Asn Glu Pro Lys Phe
145                 150                 155                 160
Leu Asp Gly Pro Tyr Val Ala Thr Val Pro Glu Met Ser Pro Val Gly
                165                 170                 175
Ala Tyr Val Leu Gln Val Lys Ala Thr Asp Ala Asp Asp Pro Thr Tyr
            180                 185                 190
Gly Asn Ser Ala Arg Val Val Tyr Ser Ile Leu Gln Gly Gln Pro Tyr
        195                 200                 205
Phe Ser Ile Asp Pro Lys Thr Gly Val Ile Arg Thr Ala Leu Pro Asn
    210                 215                 220
```

| | | | | | | | | | | | | | | |
|---|---|---|---|---|---|---|---|---|---|---|---|---|---|---|
| Met | Asp | Arg | Glu | Val | Lys | Glu | Gln | Tyr | Gln | Val | Leu | Ile | Gln | Ala | Lys |
| 225 | | | | 230 | | | | 235 | | | | | | 240 |
| Asp | Met | Gly | Gly | Gln | Leu | Gly | Gly | Leu | Ala | Gly | Thr | Thr | Ile | Val | Asn |
| | | | | 245 | | | | 250 | | | | | 255 | | |
| Ile | Thr | Leu | Thr | Asp | Val | Asn | Asp | Asn | Pro | Pro | Arg | Phe | Pro | Lys | Ser |
| | | | 260 | | | | 265 | | | | | 270 | | | |
| Ile | Phe | His | Leu | Lys | Val | Pro | Glu | Ser | Ser | Pro | Ile | Gly | Ser | Gly | Ile |
| | | 275 | | | | 280 | | | | | 285 | | | | |
| Gly | Arg | Ile | Arg | Ala | Val | Asp | Pro | Asp | Phe | Gly | Gln | Asn | Ala | Glu | Ile |
| | 290 | | | | 295 | | | | | 300 | | | | | |
| Glu | Tyr | Asn | Ile | Val | Pro | Gly | Asp | Gly | Asn | Leu | Phe | Asp | Ile | Val |
| 305 | | | | 310 | | | | 315 | | | | | 320 | |
| Thr | Asp | Glu | Asp | Thr | Gln | Glu | Gly | Val | Ile | Lys | Leu | Lys | Lys | Pro | Leu |
| | | | | 325 | | | | 330 | | | | | 335 | | |
| Asp | Phe | Glu | Thr | Lys | Lys | Ala | Tyr | Thr | Phe | Lys | Val | Glu | Ala | Ser | Asn |
| | | | 340 | | | | 345 | | | | 350 | | | | |
| Leu | His | Leu | Asp | His | Arg | Phe | His | Ser | Ala | Gly | Pro | Phe | Lys | Asp | Thr |
| | | 355 | | | | 360 | | | | | 365 | | | | |
| Ala | Thr | Val | Lys | Ile | Ser | Val | Leu | Asp | Val | Asp | Glu | Pro | Pro | Val | Phe |
| | 370 | | | | 375 | | | | 380 | | | | | | |
| Ser | Lys | Pro | Leu | Tyr | Thr | Met | Glu | Val | Tyr | Glu | Asp | Thr | Pro | Val | Gly |
| 385 | | | | | 390 | | | | 395 | | | | | 400 |
| Thr | Ile | Ile | Gly | Ala | Val | Thr | Ala | Gln | Asp | Leu | Asp | Val | Gly | Ser | Gly |
| | | | | 405 | | | | 410 | | | | | 415 | | |
| Ala | Val | Arg | Tyr | Phe | Ile | Asp | Trp | Lys | Ser | Asp | Gly | Asp | Ser | Tyr | Phe |
| | | | 420 | | | | 425 | | | | 430 | | | | |
| Thr | Ile | Asp | Gly | Asn | Glu | Gly | Thr | Ile | Ala | Thr | Asn | Glu | Leu | Leu | Asp |
| | | 435 | | | | 440 | | | | | 445 | | | | |
| Arg | Glu | Ser | Thr | Ala | Gln | Tyr | Asn | Phe | Ser | Ile | Ile | Ala | Ser | Lys | Val |
| | 450 | | | | 455 | | | | 460 | | | | | | |
| Ser | Asn | Pro | Leu | Leu | Thr | Ser | Lys | Val | Asn | Ile | Leu | Ile | Asn | Val | Leu |
| 465 | | | | | 470 | | | | 475 | | | | | 480 |
| Asp | Val | Asn | Glu | Phe | Pro | Pro | Glu | Ile | Ser | Val | Pro | Tyr | Glu | Thr | Ala |
| | | | | 485 | | | | 490 | | | | | 495 | | |
| Val | Cys | Glu | Asn | Ala | Lys | Pro | Gly | Gln | Ile | Ile | Gln | Ile | Val | Ser | Ala |
| | | | 500 | | | | 505 | | | | 510 | | | | |
| Ala | Asp | Arg | Asp | Leu | Ser | Pro | Ala | Gly | Gln | Gln | Phe | Ser | Phe | Arg | Leu |
| | | 515 | | | | 520 | | | | | 525 | | | | |
| Ser | Pro | Glu | Ala | Ala | Ile | Lys | Pro | Asn | Phe | Thr | Val | Arg | Asp | Phe | Arg |
| | 530 | | | | 535 | | | | 540 | | | | | | |
| Asn | Asn | Thr | Ala | Gly | Ile | Glu | Thr | Arg | Arg | Asn | Gly | Tyr | Ser | Arg | Arg |
| 545 | | | | | 550 | | | | 555 | | | | | 560 |
| Gln | Gln | Glu | Leu | Tyr | Phe | Leu | Pro | Val | Val | Ile | Glu | Asp | Ser | Ser | Tyr |
| | | | | 565 | | | | 570 | | | | | 575 | | |
| Pro | Val | Gln | Ser | Ser | Thr | Asn | Thr | Met | Thr | Ile | Arg | Val | Cys | Arg | Cys |
| | | | 580 | | | | 585 | | | | | 590 | | | |
| Asp | Ser | Asp | Gly | Thr | Ile | Leu | Ser | Cys | Asn | Val | Glu | Ala | Ile | Phe | Leu |
| | | 595 | | | | 600 | | | | | 605 | | | | |
| Pro | Val | Gly | Leu | Ser | Thr | Gly | Ala | Leu | Ile | Ala | Ile | Leu | Leu | Cys | Ile |
| | | 610 | | | | 615 | | | | 620 | | | | | |
| Val | Ile | Leu | Leu | Ala | Ile | Val | Val | Leu | Tyr | Val | Ala | Leu | Arg | Arg | Gln |
| 625 | | | | | 630 | | | | 635 | | | | | 640 |
| Lys | Lys | Lys | His | Thr | Leu | Met | Thr | Ser | Lys | Glu | Asp | Ile | Arg | Asp | Asn |

|       |       |       |       |       |       | 645   |       |       |       |       |       | 650   |       |       |       |       |       | 655   |       |
|-------|-------|-------|-------|-------|-------|-------|-------|-------|-------|-------|-------|-------|-------|-------|-------|-------|-------|-------|-------|

Val Ile His Tyr Asp Asp Glu Gly Gly Gly Glu Glu Asp Thr Gln Ala
           660                     665                 670

Phe Asp Ile Gly Ala Leu Arg Asn Pro Lys Val Ile Glu Glu Asn Lys
       675                 680                     685

Ile Arg Arg Asp Ile Lys Pro Asp Ser Leu Cys Leu Pro Arg Gln Arg
   690                 695                 700

Pro Pro Met Glu Asp Asn Thr Asp Ile Arg Asp Phe Ile His Gln Arg
705                 710                 715                     720

Leu Gln Glu Asn Asp Val Asp Pro Thr Ala Pro Pro Ile Asp Ser Leu
               725                 730                 735

Ala Thr Tyr Ala Tyr Glu Gly Ser Gly Ser Val Ala Glu Ser Leu Ser
           740                 745                 750

Ser Ile Asp Ser Leu Thr Thr Glu Ala Asp Gln Asp Tyr Asp Tyr Leu
       755                 760                 765

Thr Asp Trp Gly Pro Arg Phe Lys Val Val Ala Asp Met Phe Gly Glu
   770                 775                 780

Glu Glu Ser Tyr Asn Pro Asp Lys Val Thr
785                 790

( 2 ) INFORMATION FOR SEQ ID NO:61:

( i ) SEQUENCE CHARACTERISTICS:
        ( A ) LENGTH: 2690 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

| | | | | | |
|---|---|---|---|---|---|
| CTTCAAGGTT | TTGCTGACTC | AGTCTGGTAG | TCAGAGTCTG | CAGGAGAAGA | CAGTTCAAGG | 60 |
| CAGGGCCTGG | AGGATTGGAT | CAGTTTAGGG | ACAGGTCAAA | GGCTGGCTTA | GAGACCTTAG | 120 |
| AGGCAGGTTG | CTTGGGTCGT | TGAATGCTAG | TCTGGTCCTG | AGAGCCCTTT | TCTCTGGCAA | 180 |
| CTGTGGACTC | AGAGCTAACC | AATTGTAGTT | GGCAGTGGGG | GTGAAGGGTG | ATCCAGAGGC | 240 |
| CTGAGCTGCA | GAGGGCACAA | GAGAGAAAAG | ATGTCTTAGA | AAGAGCTTTG | AGAACATGCC | 300 |
| TTGGCTGCTG | GCAGGGACCT | TGGATGGGGT | AGTCTACACC | GGAAGTGCC | TGCCTGCCAT | 360 |
| CCTCTAGTGG | CTGCCTTGCA | AAATATGCTC | AGTGCAGCCG | CGTGCATGAA | TGAAAACGCC | 420 |
| GCCGGGCGCT | TCTAGTCGGA | CAAAATGCAG | CCGAGAACTC | CGCTCGTTCT | GTGCGTTCTC | 480 |
| CTGTCCCAGG | TGCTGCTGCT | AACATCTGCA | GAAGATTTGG | ACTGCACTCC | TGGATTTCAG | 540 |
| CAGAAAGTGT | TCCATATCAA | TCAGCCAGCT | GAATTCATTG | AGGACCAGTC | AATTCTAAAC | 600 |
| TTGACCTTCA | GTGACTGTAA | GGGAAACGAC | AAGCTACGCT | ATGAGGTCTC | GAGCCCATAC | 660 |
| TTCAAGGTGA | ACAGCGATGG | CGGCTTAGTT | GCTCTGAGAA | ACATAACTGC | AGTGGGCAAA | 720 |
| ACTCTGTTCG | TCCATGCACG | GACCCCCCAT | GCGGAAGATA | TGGCAGAACT | CGTGATTGTC | 780 |
| GGGGGGAAAG | ACATCCAGGG | CTCCTTGCAG | GATATATTTA | AATTTGCAAG | AACTTCTCCT | 840 |
| GTCCCAAGAC | AAAAGAGGTC | CATTGTGGTA | TCTCCCATTT | TAATTCCAGA | GAATCAGAGA | 900 |
| CAGCCTTTCC | CAAGAGATGT | TGGCAAGGTA | GTCGATAGTG | ACAGGCCAGA | AAGGTCCAAG | 960 |
| TTCCGGCTCA | CTGGAAAGGG | AGTGGATCAA | GAGCCTAAAG | GAATTTTCAG | AATCAATGAG | 1020 |
| AACACAGGGA | GCGTCTCCGT | GACACGGACC | TTGGACAGAG | AAGTAATCGC | TGTTTATCAA | 1080 |
| CTATTTGTGG | AGACCACTGA | TGTCAATGGC | AAAACTCTCG | AGGGGCCGGT | GCCTCTGGAA | 1140 |

```
GTCATTGTGA TTGATCAGAA TGACAACCGA CCGATCTTTC GGGAAGGCCC CTACATCGGC    1200
CACGTCATGG AAGGGTCACC CACAGGCACC ACAGTGATGC GGATGACAGC CTTTGATGCA    1260
GATGACCCAG CCACCGATAA TGCCCTCCTG CGGTATAATA TCCGTCAACA GACGCCTGAC    1320
AAGCCATCTC CCAACATGTT CTACATCGAT CCTGAGAAAG GAGACATTGT CACTGTTGTG    1380
TCACCTGCGC TGCTGGACCG AGAGACTCTG GAAAATCCCA AGTATGAACT GATCATCGAG    1440
GCTCAAGATA TGGCTGGACT GGATGTTGGA TTAACAGGCA CGGCCACAGC CACGATCATG    1500
ATCGATGACA AAATGATCA CTCACCAAAA TTCACCAAGA AAGAGTTTCA AGCCACAGTC    1560
GAGGAAGGAG CTGTGGGAGT TATTGTCAAT TTGACAGTTG AAGATAAGGA TGACCCCACC    1620
ACAGGTGCAT GGAGGGCTGC CTACACCATC ATCAACGGAA ACCCCGGGCA GAGCTTTGAA    1680
ATCCACACCA ACCCTCAAAC CAACGAAGGG ATGCTTTCTG TTGTCAAACC ATTGGACTAT    1740
GAAATTTCTG CCTTCCACAC CCTGCTGATC AAAGTGGAAA ATGAAGACCC ACTCGTACCC    1800
GACGTCTCCT ACGGCCCCAG CTCCACAGCC ACCGTCCACA TCACTGTCCT GGATGTCAAC    1860
GAGGGCCCAG TCTTCTACCC AGACCCCATG ATGGTGACCA GGCAGGAGGA CCTCTCTGTG    1920
GGCAGCGTGC TGCTGACAGT GAATGCCACG GACCCCGACT CCCTGCAGCA TCAAACCATC    1980
AGGTATTCTG TTTACAAGGA CCCAGCAGGT TGGCTGAATA TTAACCCCAT CAATGGGACT    2040
GTTGACACCA CAGCTGTGCT GGACCGTGAG TCCCCATTTG TCGACAACAG CGTGTACACT    2100
GCTCTCTTCC TGGCAATTGA CAGTGGCAAC CCTCCCGCTA CGGGCACTGG GACTTTGCTG    2160
ATAACCCTGG AGGACGTGAA TGACAATGCC CCGTTCATTT ACCCCACAGT AGCTGAAGTC    2220
TGTGATGATG CCAAAAACCT CAGTGTAGTC ATTTTGGGAG CATCAGATAA GGATCTTCAC    2280
CCGAATACAG ATCCTTTCAA ATTTGAAATC CACAAACAAG CTGTTCCTGA TAAAGTCTGG    2340
AAGATCTCCA AGATCAACAA TACACACGCC CTGGTAAGCC TTCTTCAAAA TCTGAACAAA    2400
GCAAACTACA ACCTGCCCAT CATGGTGACA GATTCAGGGA ACCACCCAT GACGAATATC    2460
ACAGATCTCA GGGTACAAGT GTGCTCCTGC AGGAATTCCA AAGTGGACTG CAACGCGGCG    2520
GGGGCCCTGC GCTTCAGCCT GCCCTCAGTC CTGCTCCTCA GCCTCTTCAG CTTAGCTTGT    2580
CTGTGAGAAC TCCTGACGTC TGAAGCTTGA CTCCCAAGTT TCCATAGCAA CAGGAAAAAA    2640
AAAAAATCTA TCCAAATCTG AAGATTGCGG TTTACAGCTA TCGAACTTCG               2690
```

( 2 ) INFORMATION FOR SEQ ID NO:62:

( i ) SEQUENCE CHARACTERISTICS:
        ( A ) LENGTH: 713 amino acids
        ( B ) TYPE: amino acid
        ( D ) TOPOLOGY: linear ( i i ) MOLECULE TYPE: protein ( x i ) SEQUENCE DESCRIPTION: SEQ ID NO:62:

```
Met Gln Pro Arg Thr Pro Leu Val Leu Cys Val Leu Leu Ser Gln Val
 1               5                  10                  15
Leu Leu Leu Thr Ser Ala Glu Asp Leu Asp Cys Thr Pro Gly Phe Gln
                20                  25                  30
Gln Lys Val Phe His Ile Asn Gln Pro Ala Glu Phe Ile Glu Asp Gln
                35                  40                  45
Ser Ile Leu Asn Leu Thr Phe Ser Asp Cys Lys Gly Asn Asp Lys Leu
        50                  55                  60
Arg Tyr Glu Val Ser Ser Pro Tyr Phe Lys Val Asn Ser Asp Gly Gly
65                  70                  75                  80
Leu Val Ala Leu Arg Asn Ile Thr Ala Val Gly Lys Thr Leu Phe Val
```

|     |     |     |     |     | 85  |     |     |     |     | 90  |     |     |     |     | 95  |     |
|-----|-----|-----|-----|-----|-----|-----|-----|-----|-----|-----|-----|-----|-----|-----|-----|-----|

His Ala Arg Thr Pro His Ala Glu Asp Met Ala Glu Leu Val Ile Val
            100             105                 110

Gly Gly Lys Asp Ile Gln Gly Ser Leu Gln Asp Ile Phe Lys Phe Ala
        115             120             125

Arg Thr Ser Pro Val Pro Arg Gln Lys Arg Ser Ile Val Val Ser Pro
    130             135             140

Ile Leu Ile Pro Glu Asn Gln Arg Gln Pro Phe Pro Arg Asp Val Gly
145             150             155                 160

Lys Val Val Asp Ser Asp Arg Pro Glu Arg Ser Lys Phe Arg Leu Thr
                165             170             175

Gly Lys Gly Val Asp Gln Glu Pro Lys Gly Ile Phe Arg Ile Asn Glu
            180             185                 190

Asn Thr Gly Ser Val Ser Val Thr Arg Thr Leu Asp Arg Glu Val Ile
        195             200             205

Ala Val Tyr Gln Leu Phe Val Glu Thr Thr Asp Val Asn Gly Lys Thr
    210             215             220

Leu Glu Gly Pro Val Pro Leu Glu Val Ile Val Ile Asp Gln Asn Asp
225             230             235                 240

Asn Arg Pro Ile Phe Arg Glu Gly Pro Tyr Ile Gly His Val Met Glu
                245             250             255

Gly Ser Pro Thr Gly Thr Thr Val Met Arg Met Thr Ala Phe Asp Ala
            260             265                 270

Asp Asp Pro Ala Thr Asp Asn Ala Leu Leu Arg Tyr Asn Ile Arg Gln
    275             280             285

Gln Thr Pro Asp Lys Pro Ser Pro Asn Met Phe Tyr Ile Asp Pro Glu
    290             295             300

Lys Gly Asp Ile Val Thr Val Val Ser Pro Ala Leu Leu Asp Arg Glu
305             310             315                 320

Thr Leu Glu Asn Pro Lys Tyr Glu Leu Ile Ile Glu Ala Gln Asp Met
                325             330             335

Ala Gly Leu Asp Val Gly Leu Thr Gly Thr Ala Thr Ala Thr Ile Met
            340             345                 350

Ile Asp Asp Lys Asn Asp His Ser Pro Lys Phe Thr Lys Lys Glu Phe
    355             360             365

Gln Ala Thr Val Glu Glu Gly Ala Val Gly Val Ile Val Asn Leu Thr
    370             375             380

Val Glu Asp Lys Asp Asp Pro Thr Thr Gly Ala Trp Arg Ala Ala Tyr
385             390             395                 400

Thr Ile Ile Asn Gly Asn Pro Gly Gln Ser Phe Glu Ile His Thr Asn
                405             410             415

Pro Gln Thr Asn Glu Gly Met Leu Ser Val Val Lys Pro Leu Asp Tyr
            420             425                 430

Glu Ile Ser Ala Phe His Thr Leu Leu Ile Lys Val Glu Asn Glu Asp
        435             440             445

Pro Leu Val Pro Asp Val Ser Tyr Gly Pro Ser Ser Thr Ala Thr Val
    450             455             460

His Ile Thr Val Leu Asp Val Asn Glu Gly Pro Val Phe Tyr Pro Asp
465             470             475                 480

Pro Met Met Val Thr Arg Gln Glu Asp Leu Ser Val Gly Ser Val Leu
                485             490             495

Leu Thr Val Asn Ala Thr Asp Pro Asp Ser Leu Gln His Gln Thr Ile
            500             505             510

| | | | | | | | | | | | | | |
|---|---|---|---|---|---|---|---|---|---|---|---|---|---|
| Arg | Tyr | Ser 515 | Val | Tyr | Lys | Asp | Pro 520 | Ala | Gly | Trp | Leu | Asn 525 | Ile | Asn | Pro |
| Ile | Asn 530 | Gly | Thr | Val | Asp | Thr 535 | Thr | Ala | Val | Leu | Asp 540 | Arg | Glu | Ser | Pro |
| Phe 545 | Val | Asp | Asn | Ser | Val 550 | Tyr | Thr | Ala | Leu | Phe 555 | Leu | Ala | Ile | Asp | Ser 560 |
| Gly | Asn | Pro | Pro | Ala 565 | Thr | Gly | Thr | Gly | Thr 570 | Leu | Leu | Ile | Thr | Leu 575 | Glu |
| Asp | Val | Asn | Asp 580 | Asn | Ala | Pro | Phe | Ile 585 | Tyr | Pro | Thr | Val | Ala 590 | Glu | Val |
| Cys | Asp | Asp 595 | Ala | Lys | Asn | Leu | Ser 600 | Val | Val | Ile | Leu | Gly 605 | Ala | Ser | Asp |
| Lys | Asp 610 | Leu | His | Pro | Asn | Thr 615 | Asp | Pro | Phe | Lys | Phe 620 | Glu | Ile | His | Lys |
| Gln 625 | Ala | Val | Pro | Asp | Lys 630 | Val | Trp | Lys | Ile | Ser 635 | Lys | Ile | Asn | Asn | Thr 640 |
| His | Ala | Leu | Val | Ser 645 | Leu | Leu | Gln | Asn | Leu 650 | Asn | Lys | Ala | Asn | Tyr 655 | Asn |
| Leu | Pro | Ile | Met 660 | Val | Thr | Asp | Ser | Gly 665 | Lys | Pro | Pro | Met | Thr 670 | Asn | Ile |
| Thr | Asp | Leu 675 | Arg | Val | Gln | Val | Cys 680 | Ser | Cys | Arg | Asn | Ser 685 | Lys | Val | Asp |
| Cys | Asn 690 | Ala | Ala | Gly | Ala | Leu 695 | Arg | Phe | Ser | Leu | Pro 700 | Ser | Val | Ile | Leu |
| Leu 705 | Ser | Leu | Phe | Ser | Leu 710 | Ala | Cys | Leu | | | | | | | |

CADHERIN-SPECIFIC ANTIBODIES AND HYBRIDOMA CELL LINES

FEDERAL FUNDING

This invention was made with government support under grant No. EY08106 awarded by the National Institutes of Health. The government has certain rights in the invention.

This application is a continuation-in-part of U.S. patent application Ser. No. 08/049,460 filed on Apr. 19, 1993, now abandoned which is in turn a continuation-in-part of U.S. patent application Ser. No. 07/872,643 filed on Apr. 17, 1992 now abandoned.

FIELD OF THE INVENTION

The present invention relates, in general, to materials and methods relevant to cell-cell adhesion. More particularly, the invention relates to novel $Ca^{2+}$-dependent cell adhesion proteins, referred to as cadherins, and to polynucleotide sequences encoding the cadherins. The invention also relates to methods for inhibiting binding of the cadherins to their natural ligands/antiligands.

BACKGROUND

In vivo, cell-cell adhesion plays an important role in a wide range of events including morphogenesis and organ formation, leukocyte extravasion, tumor metastasis and invasion, and the formation of cell junctions. Additionally, cell-cell adhesion is crucial for the maintenance of tissue integrity, e.g., of the intestinal epithelial barrier, of the blood brain barrier and of cardiac muscle.

Intercellular adhesion is mediated by specific cell adhesion molecules. Cell adhesion molecules have been classified into at least three superfamilies including the immunoglobulin (Ig) superfamily, the integrin superfamily and the cadherin superfamily. All cell types that form solid tissues express some members of the cadherin superfamily suggesting that cadherins are involved in selective adhesion of most cell types.

Cadherins have been generally described as glycosylated integral membrane proteins that have an N-terminal extracellular domain that determines binding specificity (the N-terminal 113 amino acids appear to be directly involved in binding), a hydrophobic membrane-spanning domain and a C-terminal cytoplasmic domain (highly conserved among the members of the superfamily) that interacts with the cytoskeleton through catenins and other cytoskeleton-associated proteins. Some cadherins lack a cytoplasmic domain, however, and appear to function in cell-cell adhesion by a different mechanism than cadherins that do have a cytoplasmic domain. The cytoplasmic domain is required for the binding function of the extracellular domain in cadherins that do have a cytoplasmic domain. Binding between members of the cadherin family expressed on different cells is mainly homophilic (i.e., a member of the cadherin family binds to cadherins of its own or a closely related subclass) and $Ca^{2+}$-dependent. For recent reviews on cadherins, see Takeichi, *Annu. Rev. Biochem.*, 59:237–252 (1990) and Takeichi, *Science*, 251, 1451–1455 (1991).

The first cadherins to be described (E-cadherin in mouse epithelial cells, L-CAM in avian liver, uvomorulin in the mouse blastocyst, and CAM 120/80 in human epithelial cells) were identified by their involvment in $Ca^{2+}$-dependent cell adhesion and by their unique immunological characteristics and tissue localization. With the later immunological identification of N-cadherin, which was found to have a different tissue distribution from E-cadherin, it became apparent that a new family of $Ca^{2+}$-dependent cell-cell adhesion molecules had been discovered.

The molecular cloning of the genes encoding mouse E-[see Nagafuchi et al., *Nature*, 329: 341–343 (1987)], chicken N- [Hatta et al., *J. Cell Biol.*, 106: 873–881 (1988)], and mouse P-[Nose et al., EMBO J. 6: 3655–3661 (1987)] cadherins provided structural evidence that the cadherins comprised a family of cell adhesion molecules. Cloning of chicken L-CAM [Gallin et al., *Proc. Natl. Acad. Sci.* USA, 84: 2808–2812 (1987)] and mouse uvomorulin [Ringwald et al., EMBO J., 6: 3647–3653 (1987)] revealed that they were identical to E-cadherin. Comparisons of the amino acid sequences of E-, N-, and P-cadherins showed a level of amino acid similarity of about 45%–58% among the three subclasses. Liaw et al., EMBO J., 9: 2701–2708 (1990) describes the use of PCR with degenerate oligonucleotides based on one conserved region of E-, N- and P-cadherins to isolate N- and P-cadherin from a bovine microvascular endothelial cell cDNA. The Liaw et al., supra, results implied that there were only E-, N-, and P-cadherins because no new cadherins were identified. Also in 1990, it was reported in Heimark et al., *J. Cell Biol.*, 110: 1745–1756 (1990) that an antibody generated to bovine aortic endothelial cells recognized an intercellular junctional molecule designated V-cadherin which had a similar molecular weight to known cadherins and was able to inhibit $Ca^{2+}$-dependent cell endothelial cell adhesion. The article did not disclose any sequence information for the protein recognized by the antibody.

No further cadherin genes were described until the identification of eight of the novel cadherins claimed herein was reported in Suzuki et al., *Cell Regulation*, 2: 261–270 (1991). Subsequently, several other cadherins were described including chicken R-cadherin [Inuzuka et al., *Neuron*, 7: 69–79 (1991)], mouse M-cadherin [Donalies et al., *Proc. Natl. Acad. Sci.* USA, 88: 8024–8028 (1991)], chicken B-cadherin [Napolitano et al., *J. Cell. Biol.*, 113: 893–905 (1991)], and T-cadherin [chicken in Ranscht et al., *Neuron*, 7: 391–402 (1991) and chicken and human in Patent Cooperation Treaty (PCT) International Publication No. WO 92/08731 published on May 29, 1992].

The determination of the tissue expression of the various cadherins reveals that each subclass of cadherins has a unique tissue distribution pattern. For example, E-cadherin is found in epithelial tissues while N-cadherin is found in nonepithelial tissues such as neural and muscle tissue. The unique expression pattern of the different cadherins is particularly significant when the role each subclass of cadherins may play in vivo in normal events (e.g., the maintenance of the intestinal epithelial barrier) and in abnormal events (e.g., tumor metastasis or inflammation) is considered. Supression of cadherin function has been implicated in the progression of various cancers. See Shimoyama et al., *Cancer Res.*, 52: 5770–5774 (1992). Different subclasses or combinations of subclasses of cadherins are likely to be responsible for different cell-cell adhesion events in which therapeutic detection and/or intervention may be desirable. Studies have also suggested that cadherins may have some regulatory activity in addition to adhesive activity. Matsunaga et al., *Nature*, 334, 62–64 (1988) reports that N-cadherin has neurite outgrowth promoting activity and Mahoney et at., *Cell*, 67, 853–868 (1991) reports that the Drosophila fat tumor supressor gene, another member of the cadherin superfamily, appear to regulate cell growth. Expression of the cytoplasmic domain of N-cadherin without its extracellular domain has been shown in Kintner et al., *Cell*, 69: 229–236 (1992) to disrupt embryonic cell adhesion and in Fugimori et al., *Mol. Biol. Cell*, 4: 37–47 (1993) to disrupt epithial cell adhesion. Thus, therapeutic intervention in the regulatory activities of cadherins expressed in specific tissues may also be desirable.

There thus continues to exist a need in the art for the identification and characterization of additional cadherins participating in cell-cell adhesion and/or regulatory events. Moreover, to the extent that cadherins might form the basis for the development of therapeutic and diagnostic agents, it is essential that the genes encoding the proteins be cloned. Information about the DNA sequences and amino acid sequences encoding the cadherins would provide for the large scale production of the proteins and for the identification of the cells/tissues naturally producing the proteins, and would permit the preparation of antibody substances or other novel binding molecules specifically reactive with the cadherins that may be useful in modulating the natural ligand/antiligand binding reactions in which the cadherins are involved.

SUMMARY OF THE INVENTION

The present invention provides materials and methods that are relevant to cell-cell adhesion. In one of its aspects, the present invention provides purified and isolated polynucleotide sequences (e.g., DNA and RNA, both sense and antisense strands) encoding novel cadherins, cadherin-4 through -12. Preferred polynucleotide sequences of the invention include genomic and cDNA sequences as well as wholly or partially synthesized DNA sequences, and biological replicas thereof (i.e., copies of purified and isolated DNA sequences made in vivo or in vitro using biological reagents). Biologically active vectors comprising the polynucleotide sequences are also contemplated.

The scientific value of the information contributed through the disclosures of the DNA and amino acid sequences of the present invention is manifest. For example, knowledge of the sequence of a cDNA encoding a cadherin makes possible the isolation by DNA/DNA hybridization of genomic DNA sequences that encode the protein and that specify cadherin-specific expression regulating sequences such as promoters, enhancers and the like. DNA/DNA hybridization procedures utilizing the DNA sequences of the present invention also allow the isolation of DNAs encoding heterologous species proteins homologous to the rat and human cadherins specifically illustrated herein.

According to another aspect of the invention, host cells, especially eucaryotic and procaryotic cells, are stably transformed or transfected with the polynucleotide sequences of the invention in a manner allowing the expression of cadherin polypeptides in the cells. Host cells expressing cadherin polypeptide products, when grown in a suitable culture medium, are particularly useful for the large scale production of cadherin polypeptides, fragments and variants; thereby enabling the isolation of the desired polypeptide products from the cells or from the medium in which the cells are grown.

The novel cadherin proteins, fragments and variants of the invention may be obtained as isolates from natural tissue sources, but are preferably produced by recombinant procedures involving the host cells of the invention. The products may be obtained in fully or partially glycosylated, partially or wholly de-glycosylated or non-glycosylated forms, depending on the host cell selected or recombinant production and/or post-isolation processing.

Cadherin variants according to the invention may comprise polypeptide analogs wherein one or more of the specified (i.e., naturally encoded) amino acids is deleted or replaced or wherein one or more nonspecified amino acids are added: (1) without loss, and preferably with enhancement, of one or more of the biological activities or immunological characteristics specific for a cadherin; or (2) with specific disablement of a particular ligand/antiligand binding function of a cadherin.

Also contemplated by the present invention are antibody substances [e.g., monoclonal and polyclonal antibodies, chimeric and humanized antibodies, and antibody domains including Fab, Fab' and F(ab')$_2$, single chain antibodies, and Fv or single variable domains] and other binding proteins or peptides specifically react with cadherins of the invention. Antibody substances can be developed using isolated natural, recombinant or synthetic cadherin polypeptide products or host cells expressing such products on their surfaces. The antibody substances may be utilized for purifying polypeptides of the invention, for determining the tissue expression of the polypeptides and as antagonists of the ligand/antiligand binding activities of the cadherins. Specifically illustrating antibody substances of the invention are the monoclonal antibodies produced by the hybridomas designated 30Q8A, 30Q4H, 45A5G, 30S2F and 45C6A which were all deposited with the American Type Culture Collection (ATCC), 12301 Parklawn Drive, Rockville, Md. 20852 on Apr. 6, 1993 and were respectively assigned ATCC Deposit Nos. HB11316, HB11317, HB11318, HB11319 and HB11320. Also illustrating antibody substances of the invention are the monoclonal antibody produced by the hybridoma designated 30T 11G which was deposited with the ATCC on Apr. 8, 1993 and was assigned ATCC Deposit No. HB11324 and the monoclonal antibody produced by the hybridoma designated 64G11F which was deposited with the ATCC on Jan. 20, 1994 and was assigned ATCC Deposit No. HB11527.

The DNA and amino acid sequence information provided by the present invention makes possible the systematic analysis of the structure and function of the cadherins described herein and definition of those molecules with which the cadherins will interact on extracellular and intracellular levels. The idiotypes of anti-cadherin monoclonal antibodies of the invention are representative of such molecules and may mimic natural binding proteins (peptides and polypeptides) through which the intercellular and intracellular activities of cadherins are modulated. Alternately, they may represent new classes of modulators of cadherin activities. Anti-idiotypic antibodies, in turn, may represent new classes of biologically active cadherin equivalents.

Methods for modulating cadherin activity may involve contacting a cadherin with an antibody (or antibody fragment), another polypeptide or peptide ligand (including peptides derived from cadherins or other proteins, or a novel peptide), or a small molecule ligand that specifically binds to a portion (extracellular or cytoplasmic) of the cadherin.

BRIEF DESCRIPTION OF THE DRAWING

Numerous aspects and advantages of the present invention will be apparent upon consideration of the following detailed description thereof, reference being made to the drawing wherein.

DETAILED DESCRIPTION

Figure 1:
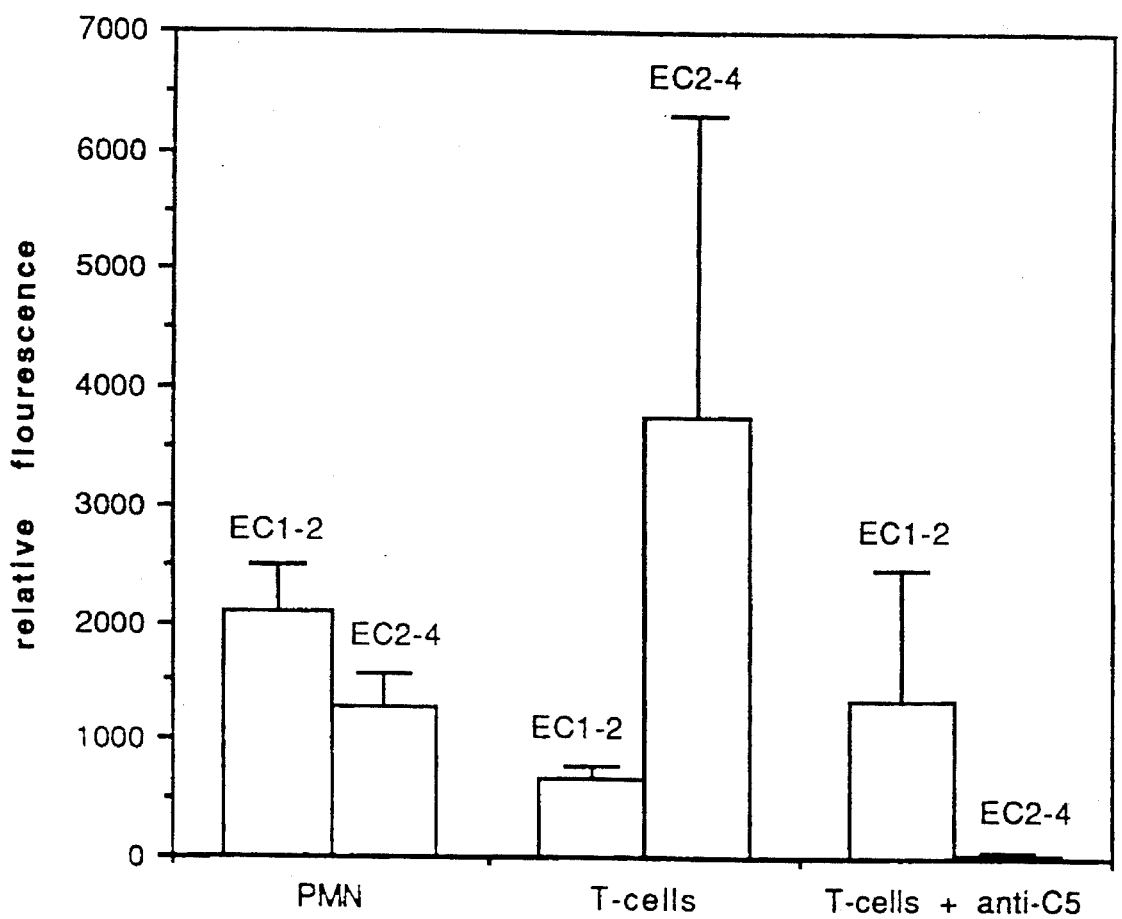
FIG. 1 is a bar graph illustrating the binding of polymorphonuclear neutrophils and T cells to fusion proteins comprising extracellular subdomains of cadherin-5.

The present invention is illustrated by the following examples wherein Example 1 describes the isolation of cDNA sequences encoding rat cadherins-4 through -11 and -13; Example 2 describes the isolation of cDNA sequences encoding the human homologs of rat cadherins-4, -5, -6, -8, -10, -11 and -13 and the isolation of a human cadherin not identified in rat, cadherin-12, as well as chromosome localization results for cadherin genes of the invention. Example 3 characterizes the relationship of cadherins of the invention to previously identified cadherins in terms of amino acid sequence and structure. The generation of polyclonal and monoclonal antibodies specific for cadherins of the invention and mapping of epitopes recognized by antibodies of the invention are described in Example 4. Example 5 describes the construction of expression constructs comprising cadherin-4, -5 and -8 sequences, transfection of mammalian cells with the constructs and results of cell-cell adhesion assays performed with the transfected cells. Example 6 presents the results of assays for cadherin mRNA and protein expression in various mammalian tissues, cells and cell lines. The results of in vitro transendothelial migration assays involving cadherin-5 and assays of neutrophil and T-cell binding to cadherin-5 fusion protein are described in Example 7. Example 8 describes expression of cadherin-5 in the blood-brain barrier and Example 9 describes cadherin-5 peptides that are capable of increasing endothelim permeability. Example 10 describes the association of the cytoplasmic domain of cadherin-5 with plakoglobin. Example 11 describes the preparation of chimeric cadherin-4/-5 molecules and cell-cell adhesion assays performed with L cells expressing the chimeric molecules. The disclosures of Suzuki et al., *Cell Regulation*, supra; Suzuki et al., *J. Cell. Biol.*, 115, Abstract 72a (1991); Suzuki et al., Cell. Struc. Funct., 16, 605 (1991); and Tanihara et al., *Invest. Ophthalmol.* Vis. Sci., 32, 1013 (1991) are incorporated by reference herein for purposes of illustrating the background of the invention.

EXAMPLE 1

Partial cDNA clones encoding nine novel cadherins were isolated from rat brain and retina by PCR. Eight of the novel rat cadherin cDNAs were isolated using degenerate PCR primers based on highly conserved regions of the cytoplasmic domain of known cadherins and one was isolated using degenerate PCR primers based on moderately conserved regions of the extracellular domain of known cadherins.

A. Preparation of Rat cDNA

Total RNAs were prepared from rat brain by the guanidium isothiocyanate/cesium chloride method described in Maniatis et al., pp. 196 in *Molecular Cloning: A Laboratory Manual*, Cold Spring Harbor, N.Y.: Cold Spring Harbor Laboratory (1982). Brain poly(A)$^+$ RNAs were then isolated using an Invitrogen (San Diego, Calif.) FastTrack kit. Rat retina poly(A)$^+$ RNA was purchased from Clonetech (Palo Alto, Calif.). cDNA was synthesized from the poly(A)$^+$ RNA of both rat brain and retina using a cDNA synthesis kit (Boehringer Mannheim Corporation, Indianopolis, Ind.).

B. Design, and Synthesis of PCR Primers Corresponding to Cadherin Cytoplasmic Domain A first pair of degenerate oligonucleotide primers, listed below in IUPAC nomenclature, was designed to correspond to highly conserved sequences in the cytoplasmic domain of mouse N-, E-, and P-cadherins. Underlined sequences at the end of each oligonucleotide indicate an EcoR1 site added to the primers to facilitate cloning of the fragments generated by PCR.

Degenerate Primer 1
TAPPYD (SEQ ID NO: 1)
5' GAATTCACNGCNCCNCCNTAYGA 3' (SEQ ID NO: 2)

Degenerate Primer 2
FKKLAD (SEQ ID NO: 3)
3' AARTTYTTYRANCGNCTCTTAAG 5' (SEQ ID NO: 4)

The degenerate oligonucleotides were synthesized using the Applied Biosystems model 380B DNA synthesizer (Foster City, Calif.).

C. Design and Synthesis of PCR Primers Corresponding to Cadherin Extracellular Domain A second pair of degenerate oligonucleotide primers, listed below in IUPAC nomenclature, was designed to correspond to moderately conserved sequences in the third subdomain of the extracellular domain of mouse N-, E-, and P-cadherins. The extracellular domains of the mouse N-, E- and P-cadherins have been characterized as having five internal subdomains, some of which may be involved in cadherin interaction with $Ca^{2+}$. Underlined sequences at the end of each oligonucleotide indicate an EcoR1 site added to the primers to facilitate cloning of the fragments generated by PCR.

Degenerate Primer 3
K(P/G)(L/I/V)D(F/Y)E (SEQ ID NO: 5)
5' GAATTCAARSSNNTNGAYTWYGA 3' (SEQ ID NO: 6)

Degerenate Primer 4
(N/D)E(A/P)PXF (SEQ ID NO: 7)
3' TRCTYSGNGGNNNNAARCTTAAG 5' (SEQ ID NO: 8)

D. Cloning of cDNA Encoding Eight Novel Rat Cadherins

PCR amplification reactions of rat brain and retina cDNA were carried out either with degenerate primers 1 and 2 or with degenerate primers 3 and 4 under conditions essentially the same as those described in Saiki et al., *Science*, 239, 487–491 (1988). Briefly, 100 ng of brain or retina first strand cDNA was used as template for amplification by Taq DNA polymerase (International Bioltechnology, New Haven, Conn.) using 10 µg of each primer set per reaction. PCR reactions were initiated by adding 2 units of Taq DNA polymerase to the reaction solution, after which 35 PCR reaction cycles were carried out. Reaction cycles consisted of denaturation performed at 94° C. for 1.5 minutes, oligonucleotide annealing at 45° C. for 2 minutes, and elongation at 72° C. for 3 minutes. The resulting PCR fragments were separated by agarose gel electrophoresis, and DNA bands of the expected size were extracted from the gel and digested with EcoR1. The fragments were then cloned into the M13 vector (Boehringer Mannheim) and *E. coli* JM101 cells were transformed with the resulting constructs. Individual clones were then isolated and sequenced. Sequencing of the DNAs was carried out using a sequenase kit (United States Biochemicals, Cleveland, Ohio) and the resulting DNA and deduced amino acid sequences of the clones were compared to sequences of known cadherins using the Microgenie program (Beckman, Fullerton, Calif.).

Ten representative cDNA clones encoding cadherins were identified from the PCR reaction based on degenerate primers 1 and 2. Two clones corresponded to rat N-, and E-cadherins, but eight clones encoded previously undescribed cadherins, and were designated cadherins-4 through -11. The DNA and deduced amino acid sequences of the eight rat cytoplasmic domain cDNA clones are respectively set out in SEQ ID NOs: 9 and 10 (cadherin-4), SEQ ID NOs: 11 and 12 (cadherin-5), SEQ ID NOs: 13 and 14 (cadherin-6), SEQ ID NOs: 15 and 16 (cadherin-7), SEQ ID NOs: 17 and 18 (cadherin-8), SEQ ID NOs: 19 and 20 (cadherin-9), SEQ ID NOs: 21 and 22 (cadherin-10) and SEQ ID NOs: 23 and 24 (cadherin-11).

An additional novel cadherin was identified from the PCR reaction based on degenerate primers 3 and 4, and it was designated cadherin-13. The DNA and deduced amino acid sequences of the rat cadherin-13 fragment are respectively set out in SEQ ID NOs: 25 and 26.

The PCR reaction based on degenerate primers 3 and 4 also amplified sequences which were later determined to be fragments of the extracellular domains of rat cadherins-4, -5, -6, -8, -9, -10 and -11. The DNA and amino acid sequences of these extracellular fragments are respectively set out in SEQ ID NOs: 27 and 28 (cadherin-4), SEQ ID NOs: 29 and 30 (cadherin-5), SEQ ID NOs: 31 and 32 (cadherin-6), SEQ ID NOs: 33 and 34 (cadherin-8), SEQ ID NOs: 35 and 36 (cadherin-9), SEQ ID NOs: 37 and 38 (cadherin-10), SEQ ID NOs: 39 and 40 (cadherin-11 ).

Larger cadherin-8 and -10 cDNAs were isolated from a rat brain cDNA library made in Uni-ZAP vector (Stratagene, La Jolla, Calif.) using labelled cadherin-8 extracellular domain PCR fragment (SEQ ID NO: 17) or cadherin-10 extracellular domain fragment (SEQ ID NO: 21) as probes. Two types of cadherin-8 cDNA clones were isolated. The first type encodes a full length cadherin, but the second type encodes a truncated protein the sequence of which diverges from the first type of cadherin-8 clone near the N-terminus of the fifth extracellular subdomain (EC5). The truncated clone contains a short stretch of unique sequence in the N-terminus of EC5 but lacks the remainder of EC5, the transmembrane domain and the cytoplasmic domain. DNA and deduced amino acid sequences of the full length cadherin-8 clone are respectively set out in SEQ ID NOs: 41 and 42 and the DNA and deduced amino acid sequences of the truncated cadherin-8 clone are set out in SEQ ID NOs: 43 and 44. The cadherin-10 cDNA clone that was isolated has an open reading frame which begins at a region corresponding to the middle of the first-extracellular domain (EC1) of previously identified cadherins. The DNA and deduced amino acid sequences of the cadherin-10 clone are set out in SEQ ID NOs: 45 and 46.

EXAMPLE 2

A. Isolation of Full Length cDNAs

Full length cDNAs encoding human homologs of rat cadherins-4, -8, -11 and -13 and partial cDNAs encoding human homologs of rat cadherins-6 and -10 were isolated from a human fetal brain cDNA library (λZapII vector, Stratagene). A full length cDNA encoding a human homolog of rat cadherin-5 was isolated from a human placental cDNA library (λgt11 vector, Dr. Millan, La Jolla Cancer Research Foundation, La Jolla, Calif.).

Probes for screening the human fetal brain and placental cDNA libraries were amplified by PCR from human brain cDNA (Dr. Taketani, Kansain Medical University, Moriguchi, Osaka, Japan) using the primers described in Example 1B–C. Probes consisting of human cadherin-4, -5, -6, -8, -10 and -11 sequences were generated using degenerate primers 1 and 2 and probes consisting of human cadherin-13 sequence were generated using degenerate primers 3 and 4. Amplification of the human fetal brain cDNA with degenerate primers 3 and 4 also generated a PCR fragment encoding a cadherin not isolated from rat, designated cadherin-12.

PCR fragments encoding human cadherins-4, -5, -6, -8, -10, -11, -12 and -13 were labelled with $^{32}$p and used to probe the human fetal brain and placental cDNA libraries according to the plaque hybridization method described in Ausubel et at., Eds., Current Protocols in Molecular Biology, Sections 6.1.1 to 6.1.4 and 6.2.1 to 6.2.3, John Wiley & Sons, New York (1987). Positives were plaque-purified and inserts were cut out using an in vivo excision method yielding Bluescript clones. The inserts were then subcloned into the M13 vector (Boehringer Mannheim) for sequencing.

Inserts consisting of full length cDNAs encoding human homologs of rat cadherins-4, -8, -11, -12 (putative) and -13 and partial cDNAs encoding human homologs of rat cadherins-6 and -10 were identified in clones from the human fetal brain cDNA library and a full length cDNA encoding a human homolog of rat cadherin-5 was identified in a clone from the human placental cDNA library. The DNA and deduced amino acid sequences of the human homologs are respectively set out in SEQ ID NOs: 47 and 48 (cadherin-4), SEQ ID NOs: 49 and 50 (cadherin-5), SEQ ID NOs: 51 and 52 (cadherin-6), SEQ ID NOs: 53 and 54 (cadherin-8), SEQ ID NOs: 55 and 56 (cadherin-10), SEQ ID NOs: 57 and 58 (cadherin-11), SEQ ID NOs: 59 and 60 (cadherin-12), and SEQ ID NOs: 61 and 62 (cadherin-13).

Chromosome Localization

The chromosomal location of the cadherin-8, -10, -11 and -13 genes was determined by conventional methods.

Briefly, C3H/HeJ-gld and Mus spretus (Spain) mice and [(C3H/HeJ-gld x Mus spretus) F$_1$×C3H/HeJ-gld] interspecies backcross mice were bred and maintained as previously described in Seldin, et al., J. Exp. Med., 167: 688–693 (1988). Mus spretus was chosen as the second parent in the cross because of the relative ease of detection of informative restriction fragment length variants (RFLVs) in comparison with crosses using conventional inbred laboratory strains. Gene linkage was determined by segregation analysis.

Genomic DNA isolated from mouse organs by standard techniques was digested with restriction endonucleases and 10 μg samples were electrophoresed in 0.9% agarose gels. DNA was transferred to Nytran membranes (Schleicher & Schull, Inc., Keene, N.H.), hybridized with the appropriate probe at 65° C. and washed under stringent conditions, all as previously described in Maniatis et al., supra). To localize the cadherin-8 gene, a probe corresponding to nucleotides 1999 to 2340 of SEQ ID NO: 41 was used. To localize the cadherin-10 gene, a probe corresponding to nucleotides 1034 to 1368 of SEQ ID NO: 45 was used. To localize the cadherin-11 gene, a probe corresponding to nucleotides 1590 to 1945 of SEQ ID NO: 57 was used. To localize the cadherin-13 gene a probe corresponding to nucleotides 1726 to 2195 of SEQ ID NO: 61 was used. Other clones used as probes in the current study and RFLVs used to detect anonymous DNA loci were all previously described [Chromosome 7, DNA segment, Washington 12 (D7Was12); the parathyroid hormone (Pth); calcitonin (Calc); hemoglobin, β chain (Hbb); metallothionein-I (Mt-1); adenine phosphoribosyltransferase (Aprt); growth hormone receptor (Ghr); prostaglandin E receptor EP2 subtype (Ptgerep2); dihydrofolate reductase-2 (Dhfr2); fibroblast growth factor a (Fgfa); and glucocorticoid receptor-1 (Grl-1)].

Comparison of the haplotype distribution of protocadherin genes with those determined for loci throughout the mouse genome allowed each to be mapped to specific regions of mouse chromosomes. The probability for linkage was >99% and indicated assignment of. The assignment of the cadherin-8, -11 and -13 genes was to mouse chromosome 8 and the assignment of the cadherin-10 gene was to mouse chromosome 15.

EXAMPLE 3

Comparison of the full-length sequences of the novel human cadherins described in Examples 1 and 2 with sequences of previously described cadherins and cadherin-related proteins provides support for the proposal that cadherins can be divided into at least three subgroups based on amino acid sequence identity and/or domain structure. Identity values for one possible alignment of the sequences of the extracellular domains of selected human cadherins are presented in Table 1 below.

TABLE 1

|    | N   | E   | P   | 4   | 5   | 8   | 11  | 12  | 13  |
|----|-----|-----|-----|-----|-----|-----|-----|-----|-----|
| N  | 100 | 45  | 45  | 68  | 30  | 34  | 35  | 33  | 46  |
| E  | 45  | 100 | 53  | 41  | 29  | 30  | 29  | 31  | 37  |
| P  | 45  | 53  | 100 | 29  | 30  | 29  | 31  | 31  | 38  |
| 4  | 68  | 41  | 41  | 100 | 29  | 33  | 34  | 33  | 44  |
| 5  | 30  | 29  | 30  | 29  | 100 | 40  | 41  | 39  | 32  |
| 8  | 34  | 30  | 29  | 33  | 40  | 100 | 66  | 58  | 32  |
| 11 | 35  | 29  | 31  | 34  | 41  | 66  | 100 | 58  | 31  |
| 12 | 33  | 31  | 31  | 33  | 39  | 58  | 58  | 100 | 33  |
| 13 | 46  | 37  | 38  | 44  | 32  | 32  | 31  | 33  | 100 |

Based on such sequence alignments and on the fact that certain combinations of cadherin sequences seem to have conserved stretches of amino acids when aligned, one subgroup of cadherins may include E-cadherin, N-cadherin, P-cadherin and cadherin-4, while a second subgroup may include cadherin-5, cadherin-8, cadherin-11 and cadherin-12. Cadherins-6, -7, -9 and -10 may also be included with the second subgroup based on their partial amino acid sequences disclosed herein. The amino acid sequence of cadherin-4 exhibits especially high amino acid sequence identity with that of R-cadherin (92%), indicating that cadherin-4 may be the human homolog of chicken R-cadherin. All cadherins in these two subgroups have a similar structure. Following an initiation codon, each has a signal sequence, prosequence, proteolytic cleavage site of precursor protein, an extracellular domain (which comprises five subdomains EC1-5), a transmembrane sequence and a cytoplasmic domain. For cadherin-5, these sequences/domains appear to correspond to about the following amino acid positions of SEQ ID NO: 50: 1–24 (signal sequence), 25–43 (prosequence), 44–147 (EC1), 148–254 (EC2), 255–368 (EC3), 369–475 (EC4), 476–589 (EC5), 590–616 (transmembrane sequence) and 617–780 (cytoplasmic domain).

Cadherin-13, T-cadherin and V-cadherin may be representative of a third subgroup of cadherins. Cadherin-13 consists of a cadherin-like extracellular domain, but has no domains that would correspond to the typical transmembrane or cytoplasmic domains of other cadherins. Even though about 10% of the clones obtained by PCR using degenerate primers 3 and 4 were cadherin-13 clones, none of the clones included sequences corresponding to a cytoplasmic domain. An attempt to isolate a cDNA that contained this region by PCR using a primer corresponding to the most C-terminal region of cadherin-13 available and a mixed oligonucleotide primer corresponding to a well-conserved amino acid sequence of the cytoplasmic domain of cadherins failed to generate any product with the anticipated molecular weight. A similar protein, T-cadherin, has been identified in chicken which aim lacks the typical cadherin cytoplasmic domain. The amino acid sequence identity between the two molecules is about 80%. Cadherin-13 may be the human homologue of chicken T-cadherin or may be a closely related molecule. Human cadherin-13 and avian T-cadherin may also both be closely related to V-cadherin. A 29-amino acid amino terminal sequence of bovine V-cadherin is similar to the start of the precursor region of cadherin-13 (93%) and T-cadherin (79%). V-cadherin is a 135 KD protein which appears to be restricted in tissue distribution to endothelium. In constrast, mature T-cadherin (has a molecular weight of 95 KD and shows a wide tissue distribution. Both V-cadherin and T-cadherin are linked to the cell membrane through phosphoinositiol.

EXAMPLE 4

Polyclonal and/or monoclonal antibodies specific for cadherins of the invention were generated.

A. Generation of Polyclonal Antibodies

Bacterial fusion proteins consisting of maltose binding protein fused to portions of cadherin extracellular subdomains (either human cadherin-4, -5 or -11, or rat cadherin-8) were generated and subsequently used for the generation of polyclonal antibodies.

A cDNA fragment corresponding to a 40 KD portion of the extracellular domain of human cadherin-5 (nucleotides 535 to 1527 of SEQ ID NO: 49) was synthesized by PCR from the full-length human cadherin-5 cDNA described in Example 2. The fragment was subcloned into the multicloning site (EcoR1-XbaI) of the pMAL-RI plasmid vector [New England Biolabs Inc. (NEB), Beverly, Mass.]. The resulting construct encodes maltose binding protein fused to the extracellular domain of cadherin-5. Constructs encoding maltose binding protein fused to the three N-terminal subdomains of human cadherin-4, rat cadherin-8 and human cadherin-11 were generated by similar methods.

E. coli NM522 cells (Stratagene) were then transformed with one of the fusion protein constructs and grown in quantity. After disruption of E. coli cells, the individual fusion proteins were purified by affinity column chromatography using amylose resin (NEB) according to the instructions of the manufacturer. When subjected to SDS-PAGE, the purified fusion proteins each showed essentially one band of the expected size.

A total of five hundred μg of a fusion protein in Freund's complete adjuvant was injected into rabbits at four subcutaneous sites. Subsequent injections were carried out at three week intervals using 100 μg of the fusion protein in Freund's incomplete adjuvant also at four subcutaneous sites. The resulting polyclonal sera generated from immunization of rabbits with cadherin-4, -5 or -8 fusion protein were collected and tested for specificity on L cells transfected with the appropriate cadherin sequence (see Example 5). Polyclonal serum generated from immunization of rabbits with cadherin-11 was also collected.

Immunoblotting of various cell types showed that the The anti-cadherin-4 polyclonal serum reacts with protein of about 130 KD in L cells transfected with full length cadherin-4 cDNA and in rat brain. Cadherin-5-specific serum reacts with a protein of about 135 KD in L cells transfected with a full length cadherin-5 DNA and with a protein of about 135 KD in human umbilical vein endothelial cells (HUVEcs). The serum does not react with MDCK cells that expressed high levels of E-cadherin. In bovine aortic endothelial cells, the anti-cadherin-5 serum reacts with a protein of about 120 KD. Additionally, the anti-cadherin-5 serum reacts with a protein which has the same molecular weight in rat brain endothelial cells in culture. The cadherin-8 polyclonal antibody detected a strong band of about 90 KD and a weak band of about 130 KD in rat brain.

B. Generation of Monoclonal Antibodies Specific for Human Cadherin-5

Monoclonal antibodies to cadherin-5 were prepared using bacterial fusion proteins containing subdomains of the extracellular domain of human cadherin-5 as immunogens. The fusion proteins prepared included maltose binding protein and the extracellular subdomains 1-2 (EC1-2) or extracellular subdomains 2–4 (EC2-4) of cadherin-5 in the bacterial expression vector pMAL (NEB). The two fusion proteins were expressed in bacteria and purified on amylose-sepharose as described in foregoing section on generation of polyclonal antibodies. The purified fusion proteins were used separately to immunize mice at two subcutaneous sites (100 µg of fusion protein per mouse in Freund's complete adjuvant). The mice then were subcutaneously immunized with Freund's incomplete adjuvant.

The spleen from each mouse was removed by sterile methods and treated in the same manner. Briefly, a single-cell suspension was formed by grinding the spleen between the frosted ends of two glass microscope slides submerged in serum free RPMI 1640 supplemented with 2 mM L-glutamine, 1 mM sodium pyruvate, 100 units/ml penicillin and 100 mg/ml streptomycin (RPMI) (Gibco, Canada). The cell suspension was filtered through a sterile 70-mesh cell strainer, and washed twice by centrifuging at 200 g for 5 minutes and resuspending the pellet in 20 ml serum free RPMI. Thymocytes taken from 3 naive Balb/c mice were prepared in a similar manner. NS-1 myeloma cells, kept in log phase in RPMI with 11% fetal bovine serum (FBS) (Hyclone Laboratories, Inc., Logan, Utah) for three days prior to fusion, were centrifuged at 200 g for 5 minutes, and the pellet was washed twice as described for the mouse spleen cells.

After washing, the spleen cells and myeloma cells were brought to a final volume of 10 ml in serum free RPMI, and 10 µl of that final volume was diluted 1:100 in serum free RPMI. Twenty µl of each dilution was removed, mixed with 20 µl 0.4% trypan blue stain in 0.85% saline, loaded onto a hemacytometer and counted. Two×10$^8$ spleen cells were combined with 4×10$^7$ NS-1 cells, centrifuged and the supernatant was aspirated. The cell pellets were dislodged by tapping the tube and 2 ml of 37° C. PEG 1500 (50% in 75 mM Hepes, pH 8.0) (Boehringer Mannheim) was added with stirring over the course of 1 minute, followed by adding 14 ml of serum free RPMI over 7 minutes. An additional 16 ml RPMI was added and the cells were centrifuged at 200 g for 10 minutes. After discarding the supernatant, the pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×10$^6$ thymocytes/ml (plating medium). The suspension was dispensed into ten 96-well flat bottom tissue culture plates at 200 ml/well. Cells in plates were fed on days 2, 4, and 6 days post-fusion by aspirating approximately 100 ml from each well with an 18 G needle, and adding 100 ml/well plating medium described above except containing 10 units/ml IL-6 and lacking thymocytes.

Fusions 30 (from a mouse immunized with EC2-4) and 45 (from a mouse immunized with EC1-2) were screened initially by antibody capture ELISA, testing for presence of mouse IgG. Secondary screening of fusions 30 and 45 consisted of assays using plates coated with a monolayer of fixed endothelial cells for ELISAs. HUVEcs, Lewis rat brain endothelial cells (LeBCE), and bovine aortic endothelial cells (BAE) were allowed to grow in 96-well flat bottom tissue culture microtiter plates until the bottom of well was completely covered with a monolayer of cells. Plates were washed twice with 100 µl/well of $Ca^{2+}/Mg^{2+}$ free PBS (CMF-PBS) and aspirated completely. Cells were then fixed with 100 µl/well of 3% p-Formaldehyde, 1% Sucrose in CMF-PBS at room temperature for 30 minutes. Cells were then permeablized with approximately 250 µl/well of CSK buffer (0.5% Triton 100, 100 mM NaCl, 10 mM PIPES, 2 mm MgCl) and incubated at room temperature for 30 minutes. Plates were blocked with 250 µl/well of 2% BSA in 1× CMF-PBS (blocking solution) and incubated at 37° C. for 60 minutes. Blocking solution was aspirated and 50 to 100 µl/well of supernatant from fusion plates was added. Plates were incubated at room temperature for 60 minutes and then were washed one time with 250 µl/well of 0.5% BSA in CMF-PBS (wash solution 1) and two times with 250 µl/well of CMF-PBS (wash solution 2). One hundred fifty µl of horseradish peroxidase conjugated goat anti-mouse IgG(fc) (Jackson ImmunoResearch, West Grove, Pa.) diluted 1:3500 in PBST was added and plates were incubated at room temperature for 60 minutes. Plates were washed as before and 150 µl substrate consisting of 1 mg/ml o-phenylene diamine (Sigma Chemical Co., St. Louis, Mo.) and 0.1 ml/ml 30% $H_2O_2$ in 100 mM Citrate, pH 4.5 was added. The color reaction was stopped after 30 minutes with the addition of 50 µl of 15% $H_2SO_4$. $A_{490}$ was read on a plate reader (Dynatech). About 20 positive wells were identified for each fusion and were subsequently cloned.

Hybridomas were screened in cloning steps in an ELISA assay by testing for reactivity of monoclonals to the cadherin-5 EC2-4 fusion protein and excluding maltose binding protein reactive monoclonals. Immulon 4 plates (Dynatech) were coated at 4° C. with 50 µl/well fusion protein diluted to 0.1 µg/well (for fusion protein) and to 0.2 µg/well (for maltose binding protein alone) in 50 mM carbonate buffer, pH 9.6. Plates were washed 3 times with PBS, 0.05% Tween 20 (PBST) and 50 µl hybridoma culture supernatant was added. After incubation at 37° C. for 30 minutes, and washing as above, 50 µl of horseradish peroxidase conjugated goat anti-mouse IgG(fc) (Jackson Immunoresearch) diluted 1:3500 in PBST was added. Plates were incubated at 37° C. for 30 minutes and washed 4 times with PBST. One hundred µl substrate consisting of 1 mg/ml o-phenylene diamine (Sigma) and 0.1 µl 30% $H_2O_2$ in 100 mM citrate, pH 4.5 was added. The color reaction was stopped after 5 minutes with the addition of 50 µl of 15% $H_2SO_4$. Absorbance at 490 nm was determined using a plate reader.

Fusion 64 (from a mouse immunized with EC1-2) was initially screened by antibody capture ELISA, testing for the presence of mouse IgG. Secondary screens of fusion 64 consisted of ELISAs testing for the presence of mouse IgG preferentially binding to cadherin-5 EC1-2 fusion protein over cadherin-5 EC2-4 fusion protein. Immulon 4 plates (Dynatech) were coated overnight at 4° C. with 100 ng/well EC1-2 or EC2-4 diluted in 50 mM carbonate buffer, pH 9.6. Plates were washed three times with PBS containing 0.05% Tween 20 (PBST) and 50 µl hybridoma culture supernatant was added. After incubation at 37° C. for 30 minutes, and washing as above, 50 µl of horseradish peroxidase conjugated goat anti-mouse IgG(fc) (Jackson ImmunoResearch) diluted 1:3500 in PBST was added. Plates were incubated as above, washed 4× with PBST and 100 µl substrate consisting of 1 mg/ml o-phenylene diamine (Sigma), and 0.1 µl/ml 30% $H_2O_2$ in 100 mM Citrate, pH 4.5, was added. The color reaction was stopped in 5 minutes with the addition of 50 μl of 15% $H_2SO_4$. $A_{490}$ was read on a plate reader (Dynatech).

Wells containing antibody that tested positive on EC1-2 but negative on EC2-4, were also tested for their activity on HUVEC cell lysates by Western blotting. Those monoclonal antibodies that strongly reacted with cadherin-5 by Western blotting were pursued further.

The hybridomas designated 30Q8A (ATCC HB11316), 30Q4H (ATCC HB11317), 45A5G (ATCC HB11318), 30S2F (ATCC HB11319), 45C6A (ATCC HB11320), 30T11G (ATCC HB11324), 30M8G, 30O6E, 30R1A and 30Q6F were identified as reactive with endothelial cells and with the cadherin-5 EC2-4 fusion protein. The hybridoma designated 64G11F (ATCC HB11527) was identified as reactive with endothelial cell lysates, reactive with cadherin-5 EC 1-2 fusion protein and not reactive with cadherin-5 EC2-4 fusion protein. All hybridomas were cloned twice by limiting dilution and grown in ascites. The monoclonal antibodies produced by the hybridomas were isotyped in an ELISA assay. The results of the assay are presented in Table 2 in Section C below.

C. Subdomain Specificity Of C5 Specific Monoclonal Antibodies

To determine if the hybridomas produced monoclonal antibodies reactive with unique epitopes of the extracellular domain of C5, the monoclonal antibodies were purified, biotinylated, and tested in a cross competition ELISA. Immulon IV 96-well plates were coated with either EC1-2 or EC2-4 cadherin-5 fusion protein at 0.2 μg/ml in 50 μl 50 mM $NaCO_3$, pH 9.6 overnight at 4° C. The wells were aspirated and washed three times with PBS/0.05% Tween 20. The plate was then blocked with 50 μl/well PBS, 2% BSA (Sigma) for 30 minutes at 37° C. Monoclonal antibodies were purified from hybridoma supernatants over a protein A-Sepharose column and the eluted antibody was dialyzed against 0.1M $NaCO_3$ pH 8.2. One mg/ml of antibody was reacted with 60 μl of a 1 mg/ml stock solution in DMSO of NHS-biotin (Pierce Chemical Co., Rockford, Ill.) for 1 hour at room temperature and the reaction was stopped by dialysis overnight at 4° C. against CMF/PBS. The biotinylated antibodies in PBS/0.05% Tween 20 were then added as primary antibody (50 μl/well) to a plate coated with fusion protein and incubated for 30 minutes at 37° C. The plate was then aspirated and washed three times with PBS/0.05% Tween 20. Peroxidase-conjugated strepavidin in PBS/Tween was added 50 μl/well and incubated for 30 minutes at 37° C. The plate was aspirated and washed three times in PBS/ 0.05% Tween 20, and o-phenylenediamine in 100 mM citrate buffer and hydrogen peroxide was added at 100 μl/well. The plate was developed at room temperature for 5–15 minutes. The reaction was stopped with 50 μl/well 15% sulfuric acid and the plate was read on a plate reader. To confirm subdomain specificity, the cadherin-5 fusion proteins EC1-2 and EC2-4 were run on SDS-PAGE (10%) and immunoblotted with the cadherin-5 specific monoclonal antibodies.

Table 2 below set outs the domain specificity and isotype of the cadherin-5 specific monoclonal antibodies.

TABLE 2

| Monoclonal Antibody | C5 Subdomain | Isotype |
| --- | --- | --- |
| 64G11F | 1 | $IgG_1$ |
| 30M8G | 2 | $IgG_{2b}$ |
| 30O6E | 2 | $IgG_{2b}$ |
| 30R1A | 2 | $IgG_{2a}$ |
| 30Q6F | 2 | $IgG_1$ |
| 30Q4H | 2 | $IgG_{2b}$ |
| 45A5G | 2 | $IgG_1$ |
| 45C6A | 2 | $IgG_1$ |
| 30S2F | 3–4 | $IgG_1$ |
| 30Q8A | 3–4 | $IgG_{2b}$ |
| 30T11G | 3–4 | $IgG_1$ |

Competition assays were carried out as described above for assays for binding to cadherin-5 EC2-4 fusion protein except that unlabelled primary cadherin-5 specific monoclonal antibodies (or mouse IgG) were added 30 minutes prior to addition of biotinylated cadherin-5 specific monoclonal antibodies. Monoclonal antibodies produced by the hybridomas 30M8G, 30O6E and 30R1A compete for a site that is near or identical to the binding site of the antibody produced by hybridoma 30Q4H.

D. Epitope Mapping Of Cadherin-5 Specific Monoclonal Antibodies

To determine the specific amino acids encoding the unique epitopes which the cadherin-5 extracellular domain-specific monoclonal antibodies recognized, the Novatope Library Construction System (Novagen Inc., Madison, Wis.) was utilized according to the instructions of the manufacturer. This system allows localization of monoclonal antibody epitopes to within 10–20 amino acids. Libraries of bacterial clones were constructed, each clone of which express a small peptide derived from the extracellular domain of human cadherin-5. The libraries were screened by standard colony lift methods using the cadherin-5 specific monoclonal antibodies as probes. Positive clones were analyzed by DNA sequencing to determine the precise amino acid sequence of the target epitope.

Two human cadherin-5 extracellular domain epitope libraries were constructed, one specific for domains 1-2 (EC1-2) and the other for domains 2-4 (EC2-4). DNA encoding either cadherin-5 EC1-2 or 2-4 was obtained by restriction enzyme digestion and gel purification of the appropriate insert from pMAL bacterial expression clones (described in Example 4B). DNase I was used to randomly cleave the insert DNA into fragments averaging 50 to 150 bp in size. The resulting fragments were first treated with T4 DNA polymerase to form blunt DNA ends and then with Tth DNA polymerase which adds a single dA residue to the 3' end. The prepared DNA fragments were ligated into the kit plasmid vector (pTOPE-1) which is designed for single stranded DNA sequencing. The resulting constructs were transformed into the kit NovaBlue DE3 competent cells, plated on LB agar plates containing 50 ug/ml carbenicillin and 15 ug/ml tetracycline, and grown overnight at 37° C. The EC1-2 library contained 75% recombinants and the EC2-4 library contained 40% recombinants.

Each cadherin-5 epitope library was plated to yield approximately 10,000 colonies with inserts. Standard colony lifts were performed using nitrocellulose filters. The bacterial colonies transferred onto the nitrocellulose filters were lysed and the protein was denatured using standard protocols. Immunoscreening of the bacterial colonies was performed using a monoclonal antibody of the invention as a probe. Monoclonal antibodies domain-mapped to cadherin-5 EC3 or EC4 were screened on the EC2-4 epitope library. Monoclonal antibodies domain-mapped to cadherin-5 EC2 were screened on both the EC 1-2 and EC2-4 epitope libraries. Positive colonies were selected, replated and rescreened to verify positive isolates. Single-stranded DNA sequencing was performed on all positive clones.

The DNA sequences of the positive clones resulting from the screening with one monoclonal antibody, were analyzed in a group. The translated DNA sequence of all clones was analyzed to determine the smallest region of homology shared among clones. Putative epitopes were identified as regions of 5–10 amino acids common in multiple clones. See Table 3 below for results.

TABLE 3

| Monoclonal Antibody | Cadherin-5 Subdomain | Epitope |
|---|---|---|
| 30Q8A | 4 | DREVYPWNL (Amino acids 430 to 439 of SEQ ID NO: 50) |
| 45C6A | 2 | FTHRLFN (Amino acids 147 to 153 of SEQ ID NO: 50) |
| 30Q6F | 2 | VTLQDINDNFP (Amino acids 242 to 252 of SEQ ID NO: 50) |
| 30S2F | 3 | GSLFVEDP (Amino acids 274 to 281 of SEQ ID NO: 50) |

To confirm the identified epitopes, epitope peptides were used in a competitive ELISA assay. Peptides were ordered from Macromolecular Resources at Colorado State University in Fort Collins, Colo. Putative epitope peptides were tested for their ability to block the appropriate monoclonal antibody from binding to either cadherin-5 fusion protein or HUVECs. Competitive ELISA assays were performed on 96-well flat bottom tissue culture microtiter plates coated with a monolayer of fixed and permeabilize HUVECs. The plates were blocked using 250 μl/well of 2% BSA (Gibco, fraction 5), in 1× CMF-PBS for one hour at room temperature. The plates were then washed twice with 0.5% BSA (Gibco) in 1× CMF-PBS. Before adding the hybridoma supernatants to the plates, the various cadherin-5 monoclonal antibody supernatants were preincubated for 1 hour at room temperature with either the appropriate peptide or an irrelevant peptide as a negative control. Dilutions of all peptides were made to place 10000, 3000, 1000, 300, 100, 30, 10, 3, and 1 ng of competing peptide per well. After the preincubation, 50 μl of the supernatant/peptide mixture was transferred to the coated plates and allowed to incubate for one hour at room temperature. The plates were washed as described and then 150 μl/well of a 1/3500 dilution of horseradish peroxidase conjugated goat-anti-mouse IgG (Fc specific) (Jackson, West Grove Pa.) was added and allowed to incubate for one hour at room temperature. The plates were washed as described and 150/d/well of substrate (1 mg/ml o-phenylenediamine (Sigma,) and 0.1 μl/ml 30% $H_2O_2$ in 100 mM citrate, pH 4.5) was added and allowed to develop for 8 minutes at room temperature. The reaction was stopped by the addition of 100 μl/well of 15% $H_2SO_4$. The plates were read at $A_{490}$ nm using a Dynatech MR5000 plate reader.

The results were tabulated as percent inhibition of signal caused by the competing peptide. For the 30Q8A supernatant the results were as follows: the inhibition was 90% or greater from 10000 ng/well to 100 ng/well. At 30 ng/well the inhibition was 82%; at 10 ng/well, 73%; at 3 ng/well, 34%; and at 1 ng/well, 22%. The irrelevant peptide control showed no significant inhibition of signal. For the 45C6A supernatant the results were as follows: the inhibition was 90% or greater at 10000 ng/well through 100 ng/well. At 30 ng/well the inhibition was 82%; at 10 ng/well it was 57%; at 3 ng/well it was 19%; and at 1 ng/well it was 2%. The irrelevant control peptide showed no significant pattern of inhibition of signal.

EXAMPLE 5

Human cadherins-4 and -5 and rat cadherin-8 were expressed in mouse fibroblast L cells (ATCC CCL1.3) which do not normally express cadherins.

A. Construction of Expression Vectors

The cDNA sequences encoding human cadherins-4 and -5 which are described in Example 2 and the cDNA sequence encoding rat cadherin-8 which is described in Example 1 were subcloned into the multicloning site of expression vector pRC/RSV (Invitrogen).

Cadherin-4 DNA sequences were isolated by an in vivo excision procedure from the λZapII clone (described in Example 2) containing the entire coding sequence of cadherin-4. Using a helper virus, the sequences were excised from λZapII in the form of Bluescript plasmid. The plasmid was then cut with HindIII and blunt-ended with T4 polymerase. The resulting DNA fragment was redigested with SpeI to generate a cadherin-4 cDNA fragment having a blunt end and a SpeI sticky end. The fragment was purified by agarose gel electrophoresis and subcloned into the pRC/RSV expression vector that had been previously digested with SpeI and XbaI (the XbaI end was blunt-ended with T4 polymerase).

The λgt11 clone containing the entire coding sequence of cadherin-5 (described in Example 2) was cut with EcoRI and the resulting fragment containing the cadherin-5 sequences was purified by agarose gel electrophoresis. The purified fragment was then subcloned into the EcoRI site of the Bluescript plasmid. Cadherin-5 sequences were cut from the resulting construct with HincII and XbaI and subcloned into the NotI-XbaI site of the pRC/RSV vector.

The full length cDNA encoding rat cadherin-8 was excised from the Uni-ZAP clone described in Example 1 by digestion with KpnI, followed by blunt-ending and re-digestion with SpeI. The cadherin-8 encoding fragment was purified by agarose gel electrophoresis and was subcloned into the pRC/RSV vector which had been digested with XbaI, blunt-ended and redigested with SpeI.

B. Transfection of L Cells

Mouse fibroblast L cells were transfected with the human cadherin-4 and -5 and rat cadherin-8 expression constructs by a $Ca^{2+}$ phosphate precipitation method and stable transfectants were obtained by G418 selection. Cadherin-4 and -8 transfectant cells showed a morphology similar to that of parental L cells (fibroblastic), but cadherin-5 transfectant cells exhibited a flattened morphology. Neuro 2a cells (ATCC CCL131) were also transfected by a $Ca^{2+}$ phosphate precipitation procedure with the cadherin-4 and cadherin-8 expression constructs. Cadherin-4 transfectants showed epithelial structure, suggesting that cadherin-4 has activity in epithelial structure formation and may be involved in the neural tissue development.

C. Northern and Western Blot Assays of Cadherin mRNA and Protein Expression in Transfected Cells Both cadherin-4, -5 and -8 transfectants showed mRNA of the expected size of 3.5 kb, 3.2 kb and 3 kb, respectively, in Northern blot analysis using the appropriate full length human cDNAs as a probe. (See Example 6A for a description of the Northern blot assay.)

For Western blots, cadherin-4, -5 and -8 transfectants were washed with PBS and SDS-PAGE sample buffer was added directly to the cells. SDS-PAGE (Laemmli) was carried out and gels were blotted electrophoretically onto PVDF membrane. The membranes were incubated in TBS containing 5% skim milk for 2 hours at room temperature and then were incubated with the appropriate polyclonal antibody in TBS containing 0.05% Tween 20 for 1 hour at room temperature. After four washes (of 5 minutes each) with TBS containing 0.05% Tween 20, the membranes were incubated with alkaline phosphatase conjugated anti-rabbit IgG antibody (Promega Corp., Madison, Wis.) in TBS containing 0.05% Tween 20 for 1 hour at room temperature. The membranes were then washed again four times with TBS containing 0.05% Tween 20 at room temperature and developed by using Promega Western blue. Cadherin-4, -5 and -8 polyclonal antibodies each reacted with a band of about 130 KD.

D. Calcium Protection from Trypsin Digestion

Since cadherins have been shown to be protected from trypsin digestion by $Ca^{2+}$, the effect of $Ca^{2+}$ on trypsin treatment (0.01% soybean trypsin for 30 minutes at 37° C.) of human cadherin-4 and -5 and rat cadherin-8 expressed on the surface of transfected L cells was examined. Two mM $Ca^{2+}$ protected the cadherin-4 from the trypsin digestion, but cadherin-5 and cadherin-8 were digested easily even in the presence of 1–5 mM of $Ca^{2+}$.

E. Cell-Cell Adhesion Assay

The cell-cell adhesion activity of the transfected cells was assayed by a re-aggregation assay as described in Yoshida-Noro et al., *Devel. Biol.*, 101, 19–27 (1984). Briefly, transfectants were grown to near confluency and then dispersed into single cells with mild trypsin treatment (0.01% for 15 minutes) in the presence of 2 mM $Ca^{2+}$. After washing, the trypsinized cells were incubated in Hepes buffered saline (HBS) containing 2 mM $CaCl_2$, 1% BSA and 20 µg/ml deoxynuclease on a rotary shaker at 50 rpm for 30 to 60 minutes and then cell aggregation was monitored. Cadherin-4 transfectant cells aggregated within 30 minutes and formed relatively large aggregates, whereas cadherin-5 transfectant cells did not aggregate under the same conditions. However, cadherin-5 transfectants gradually re-aggregated and formed relatively small aggregate after prolonged incubation (4–5 hours or more). Similarly, cadherin-8 transfectants did not show significant cell adhesion activity. Parental L cells did not show cell adhesion under the same conditions. The sensitivity of cadherin-5 and cadherin-8 to trypsin digestion may account for the reduced cell adhesion seen in the reaggregation assay because the transfected L cells are initially dispersed with trypsin in the assay.

EXAMPLE 6

The expression of mRNAs encoding cadherins of the invention was examined in rat brain, kidney, liver, lung and skin and in various human cells by Northern blot analysis. The expression of cadherin protein was also examined in endothelial cells and leukocytes by immunofluorescence or immunoblotting.

A. Northern Blot Assays of Rat Tissue and Human Cells

Poly(A)$^+$ RNA from rat brain, kidney, liver, lung and skin was prepared as described in Example 1 for rat brain. The RNA preparations were then electrophoresed in an 0.8% agarose gel under denaturing conditions and transferred onto a nitrocellulose filter. Northern blot analyses were carried out according to a method described in Thomas, *Proc. Natl. Acad. Sci. USA*, 77, 5201–5202 (1980). Filters were hybridized with rat cadherin PCR fragments (described in Example 1) labeled with $^{32}P$, including fragments corresponding to cadherins-4 through -11. The final hybridization wash was in 0.2× standard saline citrate containing 0.1% sodium dodecyl sulfate at 65° C. for 10 minutes.

Cadherin-4 and cadherin-8 through -10 mRNAs were detected only in rat brain. The cadherin-8 PCR fragment hybridized to a major band of about 3.5 kb and a minor band of about 4.5 kb in rat brain. The mRNAs detected may be alternative splicing products and may correspond to the truncated and full length cadherin-8 clones described in Example 1. Cadherin-6 and -7 probes gave weak signals on rat brain mRNA even after prolonged exposure. Cadherin-5, -6 and -11 mRNAs were detected in rat brain and other rat tissues including cadherin-5 mRNA in lung and kidney, cadherin-6 mRNA in kidney, and cadherin-11 mRNA in liver.

The expression of cadherin-8 and -11 in cultured human SK-N-SH neuroblastoma cells (ATCC HTB11), U251MG glioma cells and Y79 retinoblastoma cells (ATCC HTB 18) was also assayed by Northern blot. Human cDNAs encoding cadherins-8 and -11 (described in Example 2) were labelled with 32P and used as probes of poly(A)$^+$ RNA prepared from the cells using an Invitrogen FastTrack kit.

The Northern blot procedure detected cadherin-8 RNA in the neuroblastoma and retinoblastoma cell lines, while cadherin-11 RNA was detected only in neuroblastoma cells. These results indicate that at least some of the cadherins of the invention are expressed in neurons and glial cells and/or their precursor cells.

Cadherin-5 RNA was detected by Northern blot assay of HUVECs (Clonetics), but was not detected in A431 human epidermoid carcinoma cells (ATCC CRL1555) or IMR90 human fibroblast cells (ATCC CCL186).

B. Immunoflourescence of Endothelial Cells and Immunoblotting of Leukocytes

Cultured endothelial cells isolated from bovine aorta, bovine brain microvasculature and human umbilical vein were subjected to immunofluorescence microscopy using anti-cadherin-5 polyclonal antibodies. Cadherin-5 protein at the cell junctions which was in close association with the peripheral actin microfilaments was labelled.

In contrast, when freshly isolated leukocytes (human PMN, lymphocytes and monocytes) or the monocyte-like cell line U937 were analyzed for the expression of cadherin-5 by immunoblotting using polyclonal antibodies and a monoclonal antibody (3006E) to cadherin-5, no cadherin-5 was detected. Furthermore, using a pan-cadherin antibody [Geiger et al., *J. Cell Science*, 97: 607–614 (1990)] specific for the cytoplasmic tail, no other cadherins were detected in these cell populations.

C. Expression of Cadherin-4 in Osteoblasts

The expression of cadherin-4 has been studied in a human model of osteoblast precursors [model described in Civitelli et al., *J. Clin Invest.* 91: 1888–1896 (1993)]. These cells, isolated from the bone marrow of ribs from adult donors, differentiate into more mature osteoblasts in the presence of $10^{-7}M$ dexamthasone (dex) as demonstrated by increased alkaline phosphatase activity at 1 week, expression of matrix proteins at 1–4 weeks, and induction of calcification at 4 weeks. The developing osteoblasts express cadherin-4 as assessed by Northern analysis and immunocytochemistry. By immunocytochemistry, cadherin-4 was found to be distributed to both the cell surface and the cell cytoplasm. Northern analysis confirms that cadherin-4 is expressed by these cells and also shows that steady state levels of cadherin-4 mRNA increase significantly within the first week of dex treatment.

Two human osteogenic sarcoma cell lines, SaOS (ATCC HTB 85) and MG-63 (ATCC CRL 1427) also express cadherin-4 as assessed by Northern analysis and immunocytochemistry.

EXAMPLE 7

Three in vitro transendothelial migration assays were utilized to show that cadherin-5 may participate in the movement of leukocytes across the intercellular junctions of endothelium.

A. Transmigration Assays

The migration of leukocytes (either human polymorphonuclear neutrophils or rat T cells) was followed for specific periods of time (15 minutes for PMNs and 2 hours for T cells). Immunofluorescent labeling of leukocytes using antibodies to specific cellular markers was used distinguish between leukocytes and endothelium. The polyclonal antibodies described in Example 4 were used to measure changes in the distribution of cadherin-5. An antibody (Novocastra Laboratories Ltd., United Kingdom) to PE-CAM1 (CD31) which is an intercellular junction molecule in endothelium was used as a control.

The role of cadherin-5 in the transmigration of polymorphonuclear neutrophils (PMNs) across HUVEcs was analyzed. The system utilized, which is described in Furie et al., *J. Immunol.*, 143: 3309–3317 (1989), has been characterized with regard to electrical resistance of the endothelium and the adhesion molecules used in transmigration. HUVEcs were isolated in the absence of growth factor and cultured on human amniotic connective tissue in a two-chamber system. PMN migration on IL1β-treated HUVEcs has previously been shown to involve E-selectin and $\beta_2$ integrins (CD11/CD18). See Furie et al., *J. Immunol.*, 148: 2395–2484 (1992).

In the first assay, transmigration of PMNs was followed as an 11 minute time course on HUVEcs pretreated for four hours with IL1β (1.5 U/ml) (Collaborative Research Inc., Beford, Mass.). Prior to addition of neutrophils, antibodies to cadherin-5 heavily labelled the cell junctions of the HUVEcs in a continuous pattern. Pretreatment of the endothelial monolayer with IL1β appears to increase the distribution of cadherin-5 in the HUVEc monolayer compared to a control untreated culture. In the second assay, chemotaxis of PMNs across HUVEcs was stimulated by leukotriene $B_4$ ($LTB_4$) (Sigma) which was placed in the bottom chamber at $10^{-7}M$ while neutrophils were added to the upper chamber. Chemotaxis of PMNs to $LTB_4$ across the endothelial monolayer was previously shown to be blocked by antibodies to CD11a, CD11b and ICAM-1. [See Furie et al., *Blood*, 78: 2089–2097 (1991)] In both assays, PMNs were identified with anti-CD45 antibody (Becton Dickinson, San Jose, Calif.).

In both assays during the 11-minute time course, the majority of the PMNs that adhered also transmigrated. Addition of neutrophils caused a rapid redistribution and regional loss of cadherin-5 even at the earliest time point (3 minutes). CD31 was also lost at sites of disruption of the monolayer, but in general appeared to be more stable during the transmigration process. The loss of cadherin-5 may be due to, for example, proteases released from the neutrophils during transmigration or to loss of cell surface expression of cadherin-5 as a result of loss of cell contact.

In a third assay, CD4 antigen activated rat T cells were utilized instead of PMNs (for a two-hour time course). Rat brain microvascular endothelium was grown on Transwell 5 micron polycarbonate membranes (Costar, Cambridge, Mass.). T cells were identified using an anti-CD4 antibody (Serotee, Indianapolis, Ind.). In this assay, the loss of cadherin-5 immunolabeling did not occur during transendothelial migration even though 10% of the T cells had crossed the endothelium after two hours. These results demonstrate differential effects of PMN versus T cells on intercellular junctions during tranendothelial migration. Analysis by con focal microscopy suggests that CD4 antigen-activated T cells and PMNs have a ligand that is able to interact with cadherin-5 on the endothelium during transmigration. Photomicrographs from confocal analysis show that during leukocyte transendothelial migration leukocytes can be found spanning the intercellular junction. The leukocyte separates the cell junction and cadherin-5 remains on adjacent cells even though the endothelial cells are not in contact.

B. Adhesion of PMNs and T Cells to Cadherin-5

To quantitate the binding of PMNs and activated T-cells to cadherin-5, a cell-substrate adhesion assay was developed. This assay utilized plate-bound fusion proteins containing various extracellular subdomains of cadherin-5 (EC1-2 or EC2-4, see Example 4) and measured the binding of dye-labelled leukocytes to cadherin-5 protein using a cytofluor 2300 (Millipore, Bedford, Mass.).

The purified fusion proteins were absorbed to styrene plates and the binding of dye-labeled leukocytes to the fusion proteins was compared to binding to maltose binding protein and heat denatured bovine serum albumin (BSA) which was used to block nonspecific binding. The fusion proteins were dissolved in PBS $Ca^{2+}$ and $Mg^{2+}$, diluted into coating buffer and incubated overnight at 4° C. The plates were blocked with heat denatured BSA and then incubated with calcien (Molecular Probes, Eugene, Oreg.)-labelled cells for 1 hour at 37° C. Results of the assay are presented in FIG. 1 wherein the relative fluorescence values reported are the mean value of three samples.

PMNs bound to fusion proteins comprising the EC2-4 of cadherin-5, but preferentially bound to fusion proteins comprising EC1-2. These results are consistent with presence of cadherin subdomain 2 sequences in both fusion proteins. CD4 antigen activated T cells bound EC2-4 fusion protein. All these results, which indicate that PMNs interact with a more terminal or exposed subdomain of cadherin-5, are consistent with the rate that these cell types cross the endothelium, PMNs transmigrate in a few minutes and T cells require 30–60 minutes. The binding of U937 cells could be blocked in a dose dependent manner by polyclonal antisera made to the cadherin-5 EC2-4 subdomains.

The results presented in the foregoing paragraph in combination with the results presented in Example 6B that leukocytes do not express cadherins suggests that the counter ligand to which cadherin-5 binds on leukocytes is a distantly related cadherin or is not a cadherin. Cadherin binding has previously been thought to be homotypic.

EXAMPLE 8

Expression of cadherin-5 in the blood-brain barrier in the endothelium of the cerebral cortex was assayed by Western blot and immunocytochemistry.

A SDS lysate was prepared by boiling bovine or macaque capillaries in SDS sample buffer for 2 minutes and then drawing the extract through a 25 G syringe needle. The extract was centrifuged in a microfuge for 15 minutes at 4° C. Protein concentration in the supernatant was determined by the BCA method (Pierce) using bovine serum albumin as a standard. Samples of the supernatent (75 μg) were separated by SDS-PAGE (Laemmli) and electrophoretically transferred to nitrocellulose. The nitrocellulose was blocked with 5% milk and 10% FBS in Tris-buffered saline, pH 8.0, containing 0.05% Tween 20. Cadherin-5 specific monoclonal antibodies (30Q4H and 45C6A) were added. After washing to remove unbound antibody, the filters were incubated with alkaline phosphatase-conjugated anti-mouse IgG (Promega, Madison, Wis.). Reactive bands were visualized by addition of NBT/BCIP (Sigma, St. Louis, Mo.). Expression of cadherin-5 was detected in the freshly isolated bovine and macaque capillaries.

The Western blot results were confirmed by immunocytochemistry using the cadherin-5 antibodies 30Q4H and 45C6A. Macaque cerebral cortex was incubated in 15% sucrose in PBS for 30 minutes at 4° C. and embedded in OCT compound (Tissue-Tek, Elkhart, Ind.) in cryomolds and quickly frozen. Six micron sections were cut and placed on glass slides. The slides were washed with PBS and fixed in 3% p-formaldehyde for 5 minutes. To permeabilize the tissue sections the slides were immersed in −20° C. acetone for 10 minutes and air dried. The sections were blocked with 2% goat serum and 1% BSA in PBS for 30 minutes and then incubated with the primary antisera for 1 hour at room temperature. The sections were rinsed 3 times in PBS containing 0.1% BSA and incubated with biotinylated anti-rabbit or anti-mouse IgG (Vector Laboratories, Burlingame, Calif.) in 1% BSA in PBS for 30 minutes. After rinsing 3 times, strepavidin-conjugated with horseradish peroxidase (Vector Laboratories) was added for 30 minutes and washed 3 times. Immunolabeling was detected by reaction with diaminobenzoic acid in the presence of $NiCl_2$. The monoclonal antibody 45C6A only appeared to label larger vessels and the monoclonal antibody 30Q4H labeled both large and microvessels. The cell junctions of cerebral capillaries were labelled with the anti-cadherin-5 antibodies in a localized site.

These results and the results presented in Example 7 suggest cadherin-5 is involved in maintenance of the blood-brain barrier and that cadherin-5 peptides or cadherin-5 specific monoclonal antibodies may be able to open the blood-brain barrier.

EXAMPLE 9

Patent Cooperation Treaty (PCT) International Publication No. WO 91/04745 discusses fragments of cell adhesion molecules and antibodies to cell adhesion molecules which are purported to disrupt microvascular and endothelial cell tight junctions.

Three cadherin-5 peptides corresponding to the cell binding domain [HAV region, Blaschuk et al., *Devel. Biol.*, 139: 227–229 (1990)], the calcium binding region A1 and the calcium binding region B1 of E-cadherin [Ringwald et al., *EMBO J.*, 6: 3647–3653 (1987)] were tested for the ability to affect the permeability of brain endothelium. The peptides utilized had the following sequences:

Peptide 1 (Amino acids 114 to 128 of SEQ ID NO: 50) LTAVIVDKDTGENLE,

Peptide 2 (Amino acids 132 to 145 of SEQ ID NO: 50) SFTIKVHDVNDNWP, and

Peptide 3 (Amino acids 168 to 178 of SEQ ID NO: 50) SVTAVDADDPT, respectively.

Permeability was measured using a two-chamber culture system (Costar). Rat brain microvascular endothelium was grown on 12 mm Transwell filters with 3 micron pores (Costar) in the culture system. When the monolayers were confluent, two weeks after plating, $^3$H-inulin (201 mCi/g) (New England Nuclear, Boston, Mass.) was added to the upper chamber. Cadherin-5 peptide at 100 µg/ml was added to both the upper and lower chambers. Radioactivity appearing in the bottom chamber was measured at 15 minute intervals over a two hour time course carried out at 37° C. and was compared to the radioactivity appearing in the bottom chamber of cultures where no peptide was added or where no endothelial cells were present.

Both peptides 1 and 3 increased endothelium permeability in comparison to control cultures. The increase in permeability obtained with peptide 3 was 2.5-fold and the increase with peptide 1 was 1.5-fold over the controls. Peptide 2 had no effect on permeability.

EXAMPLE 10

The functional properties of cadherins involve not only specific intercellular interactions, but also involve intracellular interactions with the cytoskeleton. Immunoprecipitation experiments utilizing the cadherin-5-specific rabbit polyclonal antibodies and the monoclonal antibody 30Q8A (see Example 4) were performed to determine with which proteins cadherin-5 interacts on an intracellular level.

Endothelial cells were metabolically labeled overnight with 50 µCi/ml of [$^{35}$S]-methionine and were then extracted with 0.5% Triton X-100 in 10mM HEPES pH 7.4, 0.15M NaCl, 2 mM EDTA, 2 mM EGTA, 1 mM phenanthroline and protease inhibitors. The inhibitors included 1 mM PMSF, 10 µg/ml aprotinin, leupeptin, pepstatin A, antipain, soybean trypsin inhibitor, 100 µg/ml chymostatin and TPCK, 40 µg/ml of TPCK and bestatin, 50 µg/ml of benzamidine, 1 mM o-vanidate and 20 mM NaF. After 20 minutes on ice, the cells were scraped and centrifuged in a microfuge for 30 minutes at 4° C. The supernatant was precleared and either polyclonal anti-cadherin-5 or normal rabbit serum was added and incubated overnight at 4° C. Protein A-sepharose (Pharmacia, Piscataway, N.J.) was added for 2 hours at 4° C. and centrifuged. A first low stringency wash with 10 mM HEPES pH 7.4, 0.15M NaCl, 2 mM EDTA and 2 mM EGTA containing 1% Triton X-100, 0.5% DOC and 0.2% SDS was performed. A second high stringency wash was performed with the same buffer containing 2% SDS. A final wash was then performed with Tris-buffered saline, and the samples were boiled and analyzed on SDS/PAGE (7%). Three bands with molecular weights of 104 KD, 95 KD, and 82 KD were identified as associated with cadherin-5.

Three intracellular proteins, termed catenins, have previously been identified by their ability to bind to the cytoplasmic domain of E-cadherin. These proteins have been designated α, β, and γ catenins and have molecular weights of 102 KD, 88 KD and 80 KD, respectively [Ozawa et al., *EMBO J.* 8: 1711–1717 (1989)]. The association of catenins with E-cadherin seem to be required for E-cadherin function because deletion of the cytoplasmic domain of E-cadherin results in loss of cell adhesion function and catenin binding. The molecular cloning of α-catenin has shown it to be a vinculin-like protein [Nagafuki et al., *Cell*, 65: 849-857 (1991); Herrenkenecht et al., *Proc. Natl. Acad. Sci.* USA, 88: 9156–9160 (1991)]. The amino acid sequence of the Xenopus β-catenin [McCrea et al., *Science*, 254: 1359–1361 (1991)] exhibits 63% similarity to the human protein plakoglobin [Franke et al., *Proc. Natl. Acad. Sci.* USA, 86: 4027–4031 (1989)]. Plakoglobin has been localized to both the cytoplasmic region of desmosome and adherens junctions in epithelial cells. The desmonsomal component desmoglein I interacts with plakoglobin and is a member of the cadherin superfamily [Koch et al., *Eur. J. Cell. Biol.*, 53: 1–12 (1990)]. Plakoglobin has a molecular weight of 82 KD and may be the γ-catenin [Peifer et al., *J. Cell Biol.*, 118: 681–691 (1992)]. Even though endothelial cells lack desmosome, they have been shown to contain plakoglobin-associated with intercellular junctions [Franke et al., *Biol. of the Cell*, 59: 205–218 (1987)]. Other cytoskeletal elements associated with cadherins are ankyrin and fodrin [Nelson et al., *J. Cell Biol.*, 110: 349–357 (1990)].

A. Association of Cadherin-5 with Plakoglobin

To identify whether plakoglobin was one of the proteins complexed to cadherin-5, an unlabeled lysate of bovine aortic endothelial cells was made and immunoprecipitation was carried out as described above using anti-cadherin-5 antibody. The unlabelled immunoprecipitates were separated by SDS/PAGE and then electrophoretically transferred to nitrocellulose. The membrane was blocked with 5% milk in Tris-buffered saline, pH 8.0, containing 0.05% Tween 20 (TBST) and then was incubated with the murine monoclonal antibody PG5.1 (IBI Research Products, Cambridge, Mass.) to plakoglobin in blocking solution (1:20) for 1 hour at room temperature. The membrane was washed with TBST and then incubated with goat anti-mouse IgG conjugated to alkaline phosphatase. An 82 KD protein was identified using NBT/BCIP under both low and high stringency wash conditions. These results demonstrate that plakoglobin is associated with the cytoplasmic domain of cadherin-5 in endothelium. Immunofluorescence studies of regenerated endothelium show that cadherin-5 and plakoglobin are localized to the cell junctions and are coordinately regulated.

B. Association of Cadherins-4 and -5 with Catenins

Immunoprecipitations of cadherins-4 and -5 from transfected cells (Example 5) were performed. Metabolically labelled cadherin-4 and 5 transfectants were solubilized with Triton X-100 and NP40 and immunoprecipitated with the appropriate anti-cadherin-4 polyclonal antibody or anti-cadherin-5 polyclonal (or 30Q8A monoclonal) antibody. Under stringent washing conditions, cadherin-4 co-precipitated with 105 KD and 95 KD bands, whereas cadherin-5 co-precipitated with only a 95 KD band. Similar results were obtained when immunoprecipitations from HUVEcs were performed. In immunoblot analysis of the immunoprecipitated sample of cadherin-5 transfectants and HUVECS, anti-cadherin-5 antibody stained an approximately 130 KD band, anti-α-catenin antibody (IG5) stained an approximately 105 KD band, and anti-β-catenin antibody (12F7) stained an approximately 95 KD band, and antiplakoglobin antibody (PG5.1, IBL Research Product Corporation, Boston, Mass.) stained an 85 KD band. The anti-catenin antibodies are described in Johnson et al., *Exp. Cell. Reg.* 207: 252–260 (1993). In similar immunoblot analyses of the immunoprecipitated sample of cadherin-4 transfectants, anti-cadherin-4 antibody stained an approximately 130 KD band, anti-α-catenin antibody stained a 105 KD band, and anti-β-catenin antibody and anti-plakoglobin antibody stained 95 KD and 85 KD bands, respectively.

Furthermore, the levels of α-catenin, β-catenin and plakoglobin protein were significantly increased in caderin-4 and -5 transfectants when compared to levels in parental L cells.

The interaction of cadherins-4 and -5 with plakoglobin and the interactions of cadherins-4 and -5 with α- and β-catenin may therefore be targets for modulation of the activity of the cadherins.

EXAMPLE 11

As is described in Example 5, cadherin-4 transfectants exhibit a significant level of cell aggregation activity while cadherin-5 transfectants do not exhibit a significant level of cell aggregation activity under the same conditions. Therefore, the chimeric cadherin molecules comprising the extracellular and transmembrane domains of one of the two cadherins and the cytoplasmic domain of the other cadherin were constructed to investigate the role of the cadherin extracellular and cytoplasmic domains in cell-cell aggregation.

A. Construction of the Cadherin-4/-5 Chimeric Molecules

A chimeric molecule including the extracellular and transmembrane domains of cadherin-4 (amino acids 1 to 759 of SEQ ID NO: 48) and the cytoplasmic domain of cadherin-5 (amino acids 621 to 780 of SEQ ID NO: 50) was constructed and designated "chimeric cadherin-4." A chimeric molecule including the extracellular and transmembrane domains of cadherin-5 (amino acids 1 to 621 of SEQ ID NO: 50) and the cytoplasmic domain of cadherin-4 (amino acids 763 to 916 of SEQ ID NO: 48) was also constructed and was designated "chimeric cadherin-5."

The cDNAs containing the entire coding sequences of cadherin-4 (SEQ ID NO: 47) and cadherin-5 (SEQ ID NO: 49) were cut out from Bluescript clones described in Example 2A by HindIII digestion, followed by blunting and SpeI digestion, or by EcoRV and XbaI digestion. The cDNAs were then subcloned into the plasmid pRc/RSV digested with SpeI and XbaI or with HindIII and XbaI.

Chimeric cadherin-4 and chimeric cadherin-5 were prepared as follows. A MroI sequence was introduced near the N-terminus of the cadherin-4 cytoplasmic domain that corresponds to the MroI site of the cadherin-5 cytoplasmic domain by PCR using an upstream primer corresponding to 5' noncoding region of the cadherin-4 DNA and a mutagenic downstream primer corresponding to a region near the N-terminus of the cadherin-4 cytoplasmic domain and containing a MroI sequence at its 5' end. The PCR product was subcloned into the SinaI site of Bluescript SK. Next, the DNA corresponding to the cytoplasmic domain of cadherin-5 was cut from the pRc/RSV plasmid by SpeI digestion followed by blunting and MroI digestion. The resulting cadherin-5 DNA fragment was subcloned into the cadherin-4 Bluescript construct which had been digested with MroI and EcoRV downstream of cadherin-4 sequences to generate an insert encoding chimeric cadherin-4. The entire Bluescript insert encoding chimeric cadherin-4 was then subcloned into the multicloning site of the pRc/RSV vector.

To generate a DNA insert encoding chimeric cadherin-5, the cadherin-5 pRc/RSV plasmid was cut with MroI and XbaI and the DNA fragment including vector sequences and encoding the extracellular and transmembrane domains of cadherin-5 was purified by agarose gel electrophoresis. DNA sequences encoding the cadherin-4 cytoplasmic domain were amplified from the cadherin-4 pRc/RSV plasmid by PCR using an upstream mutagenic primer containing a MroI site at its 5' end and a downstream mutagenic primer containing XbaI site at its 3' end. The amplified product was disgested with MroI and XbaI and was subcloned into the agarose electrophoresis-purified cadherin-5 pRC/RSV plasmid fragment immediately downstream of the cadherin-5 extracellular and transmembrane domain sequences.

The resulting chimeric cadherin-4 and chimeric cadherin-5 constructs were then transformed into *E. coli* NM522 cells, and the vectors were isolated from the *E. coli* cells using the Quiagen plasmid purification kit (Chatsworth, Calif.).

L cells were then transfected with the vectors by the calcium phosphate method using a Pharmacia CellPhect transfection kit. The transfectant cells were isolated by the combination of G418 selection and fluorescence activated cell sorting (FACS) as described by Ozawa et al., supra. The chimeric cadherin-4 transfectants resembled wild type cadherin-5 transfectants in exhibiting flattened morphology while chimeric cadherin-5 transfectants were similar to cadherin-4 transfectants, suggesting a unique effect of the cadherin-5 cytoplasmic domain on cell shape. The expressed chimeric proteins were about 130 kDa in molecular weight and were localized at the cell periphery.

B. Cell aggregation Assay

Aggregation of the L cell transfectants was assayed. Briefly, single cell suspensions were prepared from monolayers by treatment with 0.01% trypsin in the presence 1 mM EGTA for 25 minutes, followed by pipetting. The resultant cells were collected by centrifugation and washed with $Ca^{2+}$-free Hepes-buffered saline (HBS). The collected cells were suspended in HBS containing 0.5% BSA. The cells were then incubated in HBS containing 0.5% BSA, 2 mM $CaCl_2$ and 20 µg/ml of DNase for 20–60 minutes, or in a 1:1 mixture of HBS and DMEM for incubation for longer periods of time on a rotary shaker at 37° C. Parental L cells did not show significant cell aggregation for at least 3 hours under these conditions.

Cadherin-4 transfectants aggregated within 30 minutes in the assay (Example 5), but cadherin-5 transfectants did not aggregate under the same conditions, suggesting that the cadherin extracellular domain plays an important role domain in cell-cell aggregation activity because the cadherin-5 extracellular domain does not exhibit strong aggregation activity even when linked to the cadherin-4 cytoplasmic domain. These results indicate that cadherin-5 is functionally as well as structurally distinct from cadherin-4.

C. Immunoprecipitation and Immunoblot Using Cadherin-Specific Antibodies

Chimeric cadherin-4 co-precipitated with proteins of the same molecular weight as wild-type cadherin-5 and chimeric cadherin-5 co-precipitated with proteins of the same molecular weight as wild-type cadherin-4. See Examples 10A and 10B.

While the present invention has been described in terms of preferred embodiments, it is understood that variations and improvements will occur to those skilled in the art. Thus, only such limitations as appear in the appended claims should be placed on the scope of the invention.

What is claimed is:

1. A hybridoma cell line producing a monoclonal antibody capable of specifically binding to a cadherin selected from the group consisting of cadherin-4 (SEQ. ID. NO.: 48), cadherin-5, cadherin-6, cadherin-7, cadherin-8, cadherin-9, cadherin-10, cadherin-11 and cadherin-12.

2. A hybridoma cell line producing a monoclonal antibody capable of specifically binding to cadherin-5 selected from the group consisting of 30Q8A (ATCC HB11316), 30Q4H (ATCC HB11317), 45A5G (ATCC HB11318), 30S2F (ATCC HB11319), 45C6A (ATCC HB11320), 30T11G (ATCC 11324) and 64G11F (ATCC HB11527).

3. A monoclonal antibody produced by the hybridoma cell line of claim 2.

4. An antibody or antibody binding fragment capable of specifically binding to a cadherin selected from the group consisting of cadherin-4 (SEQ. ID. NO.: 48), cadherin-5, cadherin-6, cadherin-7, cadherin-8, cadherin-9, cadherin-10, cadherin-11 and cadherin-12.

5. An antibody or antibody binding fragment characterized by the ability to specifically bind to cadherin-5 and by the ability to separately bind to a synthetic peptide having an amino acid sequence selected from the group consisting of:

| | |
|---|---|
| DREVYPWNL | (Amino acids 430 to 439 of SEQ ID NO: 50); |
| FTHRLFN | (Amino acids 146 to 153 of SEQ ID NO: 50); |
| VTLQDINDNFP | (Amino acids 242 to 252 of SEQ ID NO: 50); and |
| GSLFVEDP | (Amino acids 274 to 281 of SEQ ID NO: 50). |

6. A chimeric or humanized antibody capable of specifically binding to a cadherin selected from the group consisting of cadherin-4 (SEO. ID. NO.: 48), cadherin-5, cadherin-6, cadherin-7, cadherin-8, cadherin-9, cadherin-10, cadherin-11 and cadherin-12.

* * * * *

UNITED STATES PATENT AND TRADEMARK OFFICE
CERTIFICATE OF CORRECTION

PATENT NO. : 5,597,725

DATED : Jan. 28, 1997

INVENTOR(S) : Shintaro Suzuki

Page 1 of 3

It is certified that error appears in the above-identified patent and that said Letters Patent is hereby corrected as shown below:

Column 4, line 32 replace "30T 11G" with --30T11G--;

Column 5, line 62 replace "Design, and" with --Design and--;

Column 6, line 7 replace "5' GAATTCACNGCNCCNCCNTAYGA" with -- 5' GAATTCACNGCNCCNCCNTAYGA--;

Column 6, line 11 replace "3' AARTTYTTYRANCGNCTCTTAAG" with --3' AARTTYTTYRANCGNCTCTTAAG--;

Column 6, line 32 replace "5' GAATTCAARSSNNTNGAYTWYGA" with --5' GAATTCAARSSNNTNGAYTWYGA--;

Column 6, line 37 replace "3' TRCTYSGNGGNNNNAARCTTAAG" with --3' TRCTYSGNGGNNNNAARCTTAAG--;

Column 8, line 8 replace "$^{32}$p" with --$^{32}$P--;

Col. 8, line 11, "Ausubel et at.," with --Ausubel et al.,--;

Column 10, line 3 replace "aim" with --also--;

Col. 10, line 13 replace "(has" with --has--;

Column 10, line 33 replace "(EcoR1-XbaI)" with --(EcoR1-XbaI--;

Column 12, line 13 replace "mm" with --mM--;

Column 13, line 12 replace "3006E" with --3O6E--;

Column 13, line 17 replace "EC 1-2" with --EC1-2--;

UNITED STATES PATENT AND TRADEMARK OFFICE
CERTIFICATE OF CORRECTION

PATENT NO. : 5,597,725
DATED : Jan. 28, 1997
INVENTOR(S) : Shintaro Suzuki

It is certified that error appears in the above-identified patent and that said Letters Patent is hereby corrected as shown below:

Column 13, line 49 replace "100 mM" with --100mM--;

Column 14, line 18 replace "3006E" with --30O6E--;

Column 14, line 44 replace "150 bp" with --150bp--;

Column 14, line 66 replace "EC 1-2" with --EC1-2--;

Column 15, line 51 replace "150/d/well" with 150 $\mu$l/well--;

Column 17, line 31 replace "2 mM" with --2mM--;

Column 17, line 33 replace "2 mM" with --2mM--;

Column 18, line 17 replace "(ATCC HTB 18)" with --(ATCC HTB18)--;

Column 18, line 20 replace "32P" with --$^{32}$P--;

Column 18, line 44 replace "3006E" with --(30O6E)--;

Column 19, line 67 replace "Serotee" with --Serotec--;

UNITED STATES PATENT AND TRADEMARK OFFICE
CERTIFICATE OF CORRECTION

PATENT NO. : 5,597,725

DATED : January 28, 1997

INVENTOR(S) : Shintaro Suzuki

It is certified that error appears in the above-identified patent and that said Letters Patent is hereby corrected as shown below:

Column 24, line 36 replace "Sinai" with -Smal--;

Line 49,
Claim 6 replace "SEO. ID. NO." with --SEQ. ID. NO.--;

Signed and Sealed this

Twenty-third Day of March, 1999

Attest:

Q. TODD DICKINSON

Attesting Officer

Acting Commissioner of Patents and Trademarks